United States Patent [19]
Takagaki et al.

[11] Patent Number: 6,136,822
[45] Date of Patent: Oct. 24, 2000

[54] QUINOLINONE DERIVATIVE, METHOD FOR PREPARING THE SAME, AND ANTI-ALLERGIC AGENT

[75] Inventors: Hidetsugu Takagaki, Sakura; Shinobu Yamaguchi, Tokyo; Masayoshi Abe, Chiba; Mitsuru Sakai; Osamu Misumi, both of Sakura, all of Japan

[73] Assignee: Dainippon Ink and Chemicals, Inc., Tokyo, Japan

[21] Appl. No.: 09/201,662

[22] Filed: Dec. 1, 1998

[30] Foreign Application Priority Data

Dec. 3, 1997 [JP] Japan ................................. 9-332894

[51] Int. Cl.$^7$ .................. A61K 31/47; C07D 215/16; C07D 215/20; C07D 215/36
[52] U.S. Cl. ............................. 514/312; 546/157
[58] Field of Search ............................. 514/312; 546/157

[56] References Cited

U.S. PATENT DOCUMENTS

| | | | |
|---|---|---|---|
| 4,124,587 | 11/1978 | Hardtmann | 546/90 |
| 4,127,574 | 11/1978 | Hardtmann et al. | 546/90 |
| 5,179,107 | 1/1993 | Afonso | 514/312 |
| 5,190,956 | 3/1993 | Afonso | 514/312 |

FOREIGN PATENT DOCUMENTS

| | | |
|---|---|---|
| 9338227 | 4/1992 | Australia . |
| 91 70939 | 7/1993 | Australia . |
| 0 785 190 A2 | 1/1997 | European Pat. Off. . |

OTHER PUBLICATIONS

Patent Abstracts of Japan—Dainippon Ink and Chem. Inc. (XP002095770) (JP9100267), 1997.
Chemical Abstracts, USA, vol. 105, No. 11 (XP002095768), Sep. 15, 1986.
Chemical Abstracts, USA, vol. 100, No. 23 (XP002095769), Jun. 4, 1984.
Chemical Abstracts 126:154814, Tsien, 1996.
Chemical Abstracts 127:326572, Oshiro, 1997.
Chemical Abstracts 110:154319, Tamada, 1988.
Chemical Abstracts 120:298482, Tabusa, 1993.
Chemical Abstracts 121:L82723, Wingert, 1993.
*Tsien*WO 96/41166, PCT International Application No. PCT/US96/09652, published Dec. 19, 1996.

*Primary Examiner*—D. Margaret Seaman
*Attorney, Agent, or Firm*—Armstrong, Westerman, Hattori, McLeland & Naughton

[57] ABSTRACT

The present invention relates to a simple method for preparing a quinolinone derivative, which is effective as a medicine, e.g., as an agent for treating allergic diseases and the like; novel amide derivatives effective as an intermediate in the method; novel quinolinone derivatives obtained according to the method; and an anti-allergic agent containing a quinolinone derivative and/or physiological salt of the same as the active ingredients. The quinolinone derivative is expressed by the following general formula (II); and the method is characterized in that an amide derivative, expressed by the following formula (I), is reacted with a basic agent, followed by intramolecular ring formation:

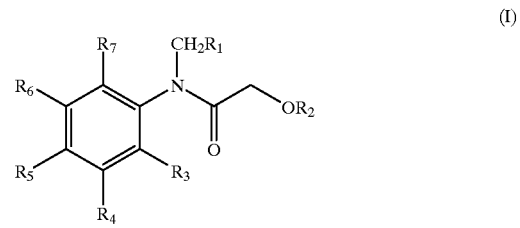

wherein $R_1$ represents a hydrogen atom, an alkyl group, an alkyl group containing a hydroxyl group an alkenyl group, or an aryl group; $R_2$ represents an alkyl group, an alkenyl group, an aryl group, or an aralkyl group; $R_3$ represents a reactive carboxyl group; and $R_4$ to $R_7$ represent, respectively and independently, a hydrogen atom; a hydroxyl group; an alkyl group; an alkoxy group; an alkenyl group; an alkenyloxy group; an aryl group; an aryloxy group; an aralkyloxy group; a $R_8R_9N$ group wherein $R_8$ and $R_9$ represent, respectively and independently, a hydrogen atom, an alkyl group, an alkenyl group an aralkyl group, or an acyl group; a nitro group; or a $R_{10}OOC$ group wherein $R_{10}$ represents a hydrogen atom, an alkyl group, an alkenyl group, an aryl group, or an aralkyl group;

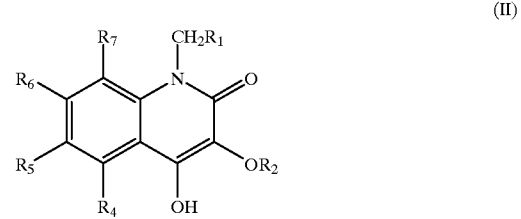

wherein $R_1$, $R_2$ and $R_4$ to $R_7$ represent, respectively, the same constituents as described in formula (I).

15 Claims, No Drawings

QUINOLINONE DERIVATIVE, METHOD FOR PREPARING THE SAME, AND ANTI-ALLERGIC AGENT

BACKGROUND OF THE INVENTION

1. Field of the Invention

The present invention relates to a simple method for preparing a quinolinone derivative, which is effective as a medicine, e.g., as an agent for treating allergic diseases and the like; novel amide derivatives effective as an intermediate in said method; novel quinolinone derivatives obtained by means of said method; and an anti-allergic agent containing a quinolinone derivative and/or physiological salt of the same as the active ingredients.

2. Background Art

The inventors of the present invention have found that a quinolinone derivative having a substituent group at the 7-position and physiological salts thereof are effective against both immediate-type hypersensitivity reactions and delayed-type hypersensitivity reactions, being extremely useful as a drug with few side effects, as disclosed in Japanese Patent Application, First Application No. Hei 09-100267 and Japanese Patent Application, First Application No. Hei 09-255659. A method for preparing such a quinolinone derivative was disclosed in both Japanese Patent Application, First Application No. Hei 09-100267 and Japanese Patent Application, First Application No. Hei 09-255659, as shown below.

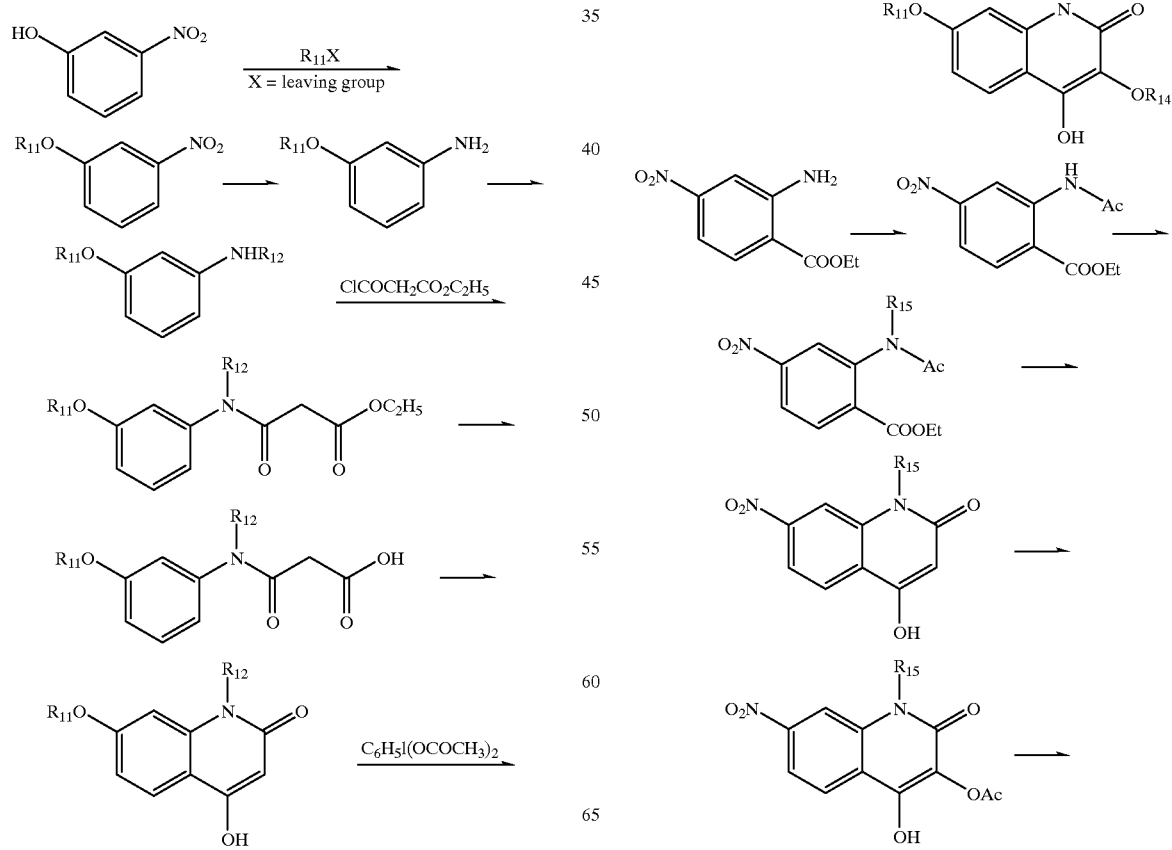

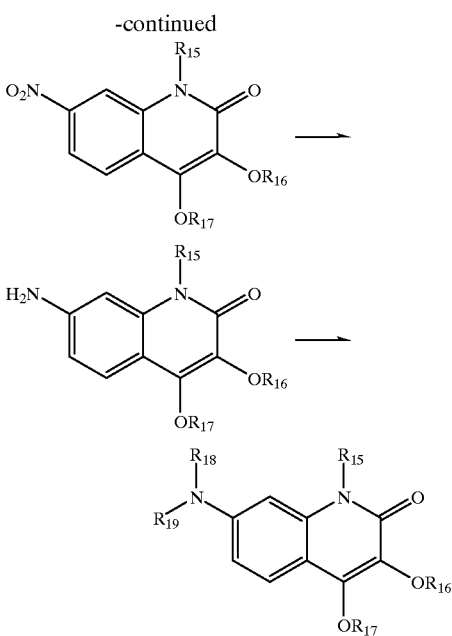

However, in the preparation method disclosed in these documents, in particular, when preparing a compound having a substituent group at the 3-position, it was necessary to proceed along a complex reaction pathway involving the steps of introducing a protecting group, de-protecting, introducing a substituent group, and then de-protecting again. Thus, the method was not necessarily satisfactory for industrial application.

Examples of other quinolinone derivatives and methods for preparing the same, include *Monatsh.Chem.*, 98(1), pp. 100–104, 1967, which discloses infrared absorption spectrum data for 3-methoxy-4-hydroxy-2(1H)-quinolinone, 3-ethoxy-4-hydroxy-2(1H)-quinolinone, and 3,4-dimethoxy-2(1H)-quinolinone, as quinolinone compounds having substituent groups at the 3- and 4-positions of the nitrogen-containing ring of quinolinone, while lacking substituent groups on the aromatic group ring.

*Monatsh.Chem.*, 99(6), pp. 2157–2166, 1968, also discloses a method for preparing 3,4-dihydroxy-2(1H)-quinolinone and 3,4-dihydroxy-1-phenyl-2(1H)-quinolinone.

Additionally, *Liebigs Ann. Chem.*, 9, pp. 1545–1551, 1973, discloses a method for preparing 3,4-dihydroxy-1-phenyl-2(1H)-quinolinone and 3,4-diacetoxy-1-phenyl-2(1H)-quinolinone.

Furthermore, *Chem. Ber.* 106, pp. 1537–1548, 1973, discloses a method for preparing 3,4-dihydroxy-1-methyl-2(1H)-quinolinone, and *Z. Naturforsh., B; Anorg. Chem., Org. Chem.*, 33B(4) pp.429–432, 1978, discloses a method for preparing 3,4-dihydroxy-1-phenyl-2(1H)-quinolinone.

*Monatsh. Chem.*, 115(2), pp. 231–242, 1984, discloses a method for preparing 3,4-dihydroxy-2(1H)-quinolinone, 3-methoxy-4-hydroxy-2(1H)-quinolinone, 3-ethoxy-4-hydroxy-2(1H)-quinolinone, 3-propoxy-4-hydroxy-2(1H)-quinolinone, 3-trifluoroacetoxy-4-hydroxy-2(1H)-quinolinone, 3-acetoxy-4-hydroxy-2(1H)-quinolinone, 3-acetoxy-4-hydroxy-1-methyl-2(1H)-quinolinone, and 3-methoxy-4-hydroxy-1-methyl-2(1H)-quinolinone.

*Phosphorus and Sulfur*, 21(1), pp. 47–52, 1984, discloses 3,4-dihydroxy-2(1H)-quinolinone 3-dimethylphosphate, 3-hydroxy-4-methoxy-2(1H)-quinolinone 3-dimethylphosphate, 3,4-dihydroxy-2(1H)-quinolinone 3-diethylphosphate, 3,4-dihydroxy-2(1H)-quinolinone 3-diisopropylphosphate, and N-methyls of these compounds.

*FEBS Lett.*, 246(1–2), pp. 113–116, 1989, discloses a method for preparing 3,4-dihydroxy-2(1H)-quinolinone. *Phytochemistry*, 28(5), pp. 1517–1519, 1989, discloses 3,4-dimethoxy-2(1H)-quinolinone and 3,4-dimethoxy-1-methyl-2(1H)-quinolinone as extracts of *Clausena anisata*.

As compounds having substituent groups on the aromatic ring of a quinolinone, *Indian J. Chem., Sect. B*, 15B(5), pp. 440–444, 1977, discloses 3,4-dimethoxy-2(1H)-quinolinone, 8-methoxy-3-methoxy-4-hydroxy-1-methyl-2(1H)-quinolinone, and a methyl ether thereof, 8-methoxy-3,4-dimethoxy-1-methyl-2(1H)-quinolinone as compounds obtained from the bark of *Chloroxylon swietenia* DC.

Additionally, *Indian J. Chem., Sect. B*, 22B(12), pp. 1254–1256, 1983, discloses a method for preparing 8-methoxy-3-methoxy-4-hydroxy-2(1H)-quinolinone and 8-methoxy-3,4-dimethoxy-1-methyl-2(1H)-quinolinone.

Additionally, *J. Heterocyclic Chem.*, 22, pp. 1087–1088, 1985, discloses a method for preparing 3-methoxy-4-hydroxy-1-methyl-2(1H)-quinolinone and 8-methoxy-3-methoxy-4-hydroxy-1-methyl-2(1H)-quinolinone.

*Journal of Natural Products*, 58(4), pp. 574–576, 1995, discloses 8-methoxy-3,4-dihydroxy-2(1H)-quinolinone as a component obtained from *Eriostemon gardneri*. However, as described above, only methoxy groups are known as substituent groups for the aromatic group rings of quinolinone derivatives.

In addition, U.S. Pat. No. 5,378,694 (corresponding to WO 92/04328 and Japanese Patent Application, Second Publication No. Hei 6-502845) describes quinolinone derivatives having a carbonyl group as the 3-position substituent group, and a hydroxyl group or an alkoxy group as the 4-position substituent group; the anti-viral activities and anti-hypertensive activities of these compounds are also described therein.

Moreover, U.S. Pat. No. 5,412,104 (corresponding to WO 92/04327 and Japanese Patent Application, Second Publication No. Hei 7-110853) describes quinolinone derivatives having a substituent group containing a carbonyl group as the 3-position substituent group, and an alkoxy group, a carbonyloxy group or an amino group as the 4-position substituent group, along with the anti-viral activities of these compounds; European Patent No. 0459561 A2 discloses 2,4-dioxotetrahydroquinoline derivatives, wherein the 3-position substituent group is a substituent group containing a carbonyl group and the 4-position group is a 4-ketone tautomer.

European Patent Application, Publication No. 0481676 A1 discloses a quinolinone derivative having an aromatic group with a substituent group as the 3-position substituent group and a hydroxyl group as the 4-position substituent group; U.S. Pat. No. 4,124,587 discloses a quinolinone derivative having a sulfinyl group as the 3-position substituent group and a hydroxyl group as the 4-position substituent group; and U.S. Pat. No. 4,127,574 discloses a quinolinone derivative having a sulfonyl group as the 3-position substituent group and a hydroxyl group as the 4-position substituent group.

WO 96/04288 discloses 5,7-dimethyl-4-hydroxy-2(1H)-quinolinone and 5,7-dichloro-4-hydroxy-2(1H)-quinolinone; Furthermore, U.S. Pat. No. 5,179,107 and U.S. Pat. No. 5,190,956 abstractly describe an extremely wide range of quinolinone derivatives having substituent groups on the aromatic group ring and having oxygens directly bonded to the 3- and 4-positions.

These US patent publications disclose quinolinone derivatives having the characteristic that the substituent groups at the 3- and 4-positions are identical substituent groups, and disclose that these derivatives have anti-viral activity.

SUMMARY OF THE INVENTION

In consideration of the aforementioned, the present invention provides a simple method for preparing a quinolinone derivative which is effective as a medicine, e.g., as an anti-allergic agent; novel amide derivatives effective as an intermediate in said method; novel quinolinone derivatives obtained according to said method; and an anti-allergic agent containing a quinolinone derivative and/or physiological salt thereof as the active ingredients. The inventors of the present invention have found that various desirable quinolinone derivatives are efficiently obtained by means of using an amide derivative, expressed by general formula (I), as an intermediate, and promoting the intramolecular ring formation of the amide derivative using an alkali compound. Furthermore, these aforementioned quinolinone derivatives are extremely useful as anti-allergic agents.

In other words, the present invention comprises:

(1) A method for preparing a quinolinone derivative, expressed by the following general formula (II), characterized in that an amide derivative, expressed by the following general formula (I), is reacted with a basic agent, followed by intramolecular ring formation;

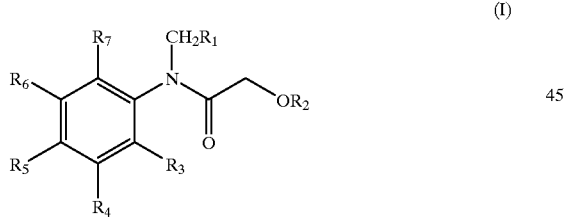

(I)

[wherein, $R_1$ represents a hydrogen atom, an alkyl group, an alkyl group containing a hydroxyl group, an alkenyl group, or an aryl group; $R_2$ represents an alkyl group, an alkenyl group, an aryl group, or an aralkyl group; $R_3$ represents a reactive carboxyl group; and $R_4$ to $R_7$ represent, respectively and independently, a hydrogen atom, a hydroxyl group, an alkyl group, an alkoxy group, an alkenyl group, an alkenyloxy group, an aryl group, an aryloxy group, an aralkyloxy group, a $R_8R_9N$ group (wherein, $R_8$ and $R_9$ represent, respectively and independently, a hydrogen atom, an alkyl group, an alkenyl group, an aralkyl group, or an acyl group), a nitro group, or a $R_{10}OOC$ group (wherein, $R_{10}$ represents a hydrogen atom, an alkyl group, an alkenyl group, an aryl group, or an aralkyl group)].

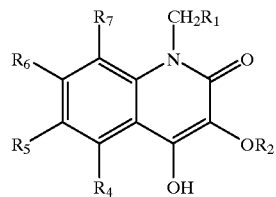

(II)

[wherein, $R_1$, $R_2$ and $R_4$ to $R_7$ represent, respectively, the same constituents as described in general formula (I)].

(2) A method for preparing a quinolinone derivative according to (1), wherein $R_1$ represents a hydrogen atom, a straight-chain or branched-chain alkyl group having 1 to 9 carbon atoms, a straight-chain or branched-chain alkyl group containing a hydroxyl group and having 1 to 5 carbon atoms, a straight-chain or branched-chain alkenyl group having 2 to 9 carbon atoms, or an aryl group having 5 to 8 carbon atoms; $R_2$ represents a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; $R_4$, $R_5$ and $R_7$ each represents a hydrogen atom; and $R_6$ represents a $R_8R_9N$ group (wherein, $R_8$ and $R_9$ represent, respectively and independently, a hydrogen atom, an alkyl group having 1 to 10 carbon atoms, an alkenyl group having 2 to 10 carbon atoms, an aralkyl group having 7 to 9 carbon atoms, or an acyl group having 2 to 12 carbon atoms);

(3) A method for preparing a quinolinone derivative according to (1), wherein $R_1$ represents a hydrogen atom; $R_2$ represents a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; $R_4$, $R_5$ and $R_7$ each represents a hydrogen atom; and $R_6$ represents a $R_8R_9N$ group (wherein, $R_8$ and $R_9$ represent, respectively and independently, a hydrogen atom, an alkyl group having 1 to 10 carbon atoms, an alkenyl group having 2 to 10 carbon atoms, an aralkyl group having 7 to 9 carbon atoms, or an acyl group having 2 to 12 carbon atoms);

(4) A method for preparing a quinolinone derivative according to (1), wherein $R_1$ represents a hydrogen atom, a straight-chain or branched-chain alkyl group having 1 to 9 carbon atoms, a straight-chain or branched-chain alkyl group containing a hydroxyl group and having 1 to 5 carbon atoms, a straight-chain or branched-chain alkenyl group having 2 to 9 carbon atoms, or an aryl group having 5 to 8 carbon atoms; $R_2$ represents a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; $R_4$, $R_5$ and $R_7$ each represents a hydrogen atom; and $R_6$ represents a nitro group;

(5) A method for preparing a quinolinone derivative according to (1), wherein $R_1$ represents a hydrogen atom; $R_2$ represents a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; $R_4$, $R_5$ and $R_7$ each represents a hydrogen atom; and $R_6$ represents a nitro group;

(6) A method for preparing a quinolinone derivative according to (1), wherein $R_1$ represents a hydrogen atom, a straight-chain or branched-chain alkyl group having 1 to 9 carbon atoms, a straight-chain or branched-chain alkyl group containing a hydroxyl group and having 1 to 5 carbon atoms, a straight-chain or branched-chain alkenyl group having 2 to 9 carbon atoms, or an aryl group having 5 to 8 carbon atoms; $R_2$ represents a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; $R_4$, $R_5$ and $R_7$ each represents a hydrogen atom; and $R_6$ represents a hydroxyl group, a straight-chain or branched-chain alkyloxy group having 1 to 10 carbon atoms, a straight-chain or branched-chain alkenyloxy group having 2 to 10 carbon atoms, or an aralkyloxy group having 7 to 9 carbon atoms.

(7) A method for preparing a quinolinone derivative according to one of (1) to (6), characterized in that said basic agent is an alkali metal alkoxide;

(8) A method for preparing a quinolinone derivative according to one of (1) to (6), characterized in that said basic agent is an alkali metal amide;

(9) An amide derivative expressed by the following general formula (I);

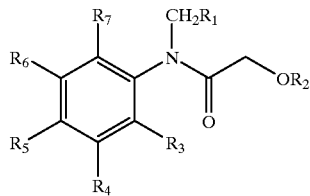

(I)

[wherein, $R_1$ represents a hydrogen atom, an alkyl group, an alkyl group containing a hydroxyl group, an alkenyl group, or an aryl group; $R_2$ represents an alkyl group, an alkenyl group, an aryl group, or an aralkyl group; $R_3$ represents a reactive carboxyl group; $R_4$, $R_5$ and $R_7$ each represents a hydrogen atom; and $R_6$ represents either a $R_8R_9N$ group (wherein, $R_8$ and $R_9$ represent, respectively and independently, a hydrogen atom, an alkyl group, an alkenyl group, an aralkyl group, or an acyl group), or a nitro group].

(10) An amide derivative according to (9), wherein $R_1$ represents a hydrogen atom, a straight-chain or branched-chain alkyl group having 1 to 9 carbon atoms, a straight-chain or branched-chain alkyl group containing a hydroxyl group and having 1 to 5 carbon atoms, a straight-chain or branched-chain alkenyl group having 2 to 9 carbon atoms, or an aryl group having 5 to 8 carbon atoms; $R_2$ represents a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; and $R_8$ and $R_9$ represent, respectively and independently, a hydroxyl group, an alkyl group having 1 to 10 carbon atoms, an alkenyl group having 2 to 10 carbon atoms, an aralkyl group having 7 to 9 carbon atoms, or an acyl group having 2 to 12 carbon atoms;

(11) An amide derivative according to (10), wherein $R_1$ represents a hydrogen atom; $R_2$ represents a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; and $R_8$ and $R_9$ represent, respectively and independently, a hydroxyl group, an alkyl group having 1 to 10 carbon atoms, an alkenyl group having 2 to 10 carbon atoms, an aralkyl group having 7 to 9 carbon atoms, or an acyl group having 2 to 12 carbon atoms;

(12) An amide derivative according to (10), wherein $R_1$ represents either a hydrogen atom, or a straight-chain or branched-chain alkyl group having 1 to 9 carbon atoms; and $R_2$ represents a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms;

(13) A quinolinone derivative and physiological salt of the same, expressed by the following general formula (II);

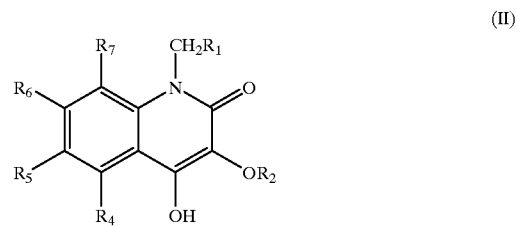

(II)

[wherein, $R_1$ represents a hydrogen atom, an alkyl group, an alkyl group containing a hydroxyl group, an alkenyl group, or an aryl group; $R_2$ represents an alkyl group, an alkenyl group, an aryl group, or an aralkyl group; and $R_4$ to $R_7$ represent, respectively and independently, a hydrogen atom, a hydroxyl group, an alkyl group, an alkoxy group, an alkenyl group, an alkenyloxy group, an aryl group, an aryloxy group, an aralkyloxy group, a $R_8R_9N$ group (wherein, $R_8$ and $R_9$ represent, respectively and independently, a hydrogen atom, an alkyl group, an alkenyl group, an aralkyl group or an acyl group), a nitro group, or a $R_{10}OOC$ group (wherein, $R_{10}$ represents a hydrogen atom, an alkyl group, an alkenyl group, an aryl group, or an aralkyl group), with the exception that the following two types of compounds are not included: (i) a compound in which $R_4$, $R_5$ and $R_7$ are respectively hydrogen atoms; and $R_6$ is selected from the group comprising a hydrogen atom, a hydroxyl group, an alkoxy group, an alkenyloxy group, an aralkyloxy group, a $R_8R_9N$ group (wherein, $R_8$ and $R_9$ represent, respectively and independently, a hydrogen atom, an alkyl group, an alkenyl group, an aralkyl group, or an acyl group), and a nitro group; and (ii) a compound in which $R_4$, $R_5$ and $R_6$ are respectively hydrogen atoms, and $R_7$ is a methoxy group].

(14) A quinolinone derivative and physiological salt of the same according to (13), wherein $R_1$ represents a hydrogen atom, a straight-chain or branched-chain alkyl group having 1 to 9 carbon atoms, a straight-chain or branched-chain alkyl group containing a hydroxyl group and having 1 to 5 carbon atoms, a straight-chain or branched-chain alkenyl group having 2 to 9 carbon atoms, or an aryl group having 5 to 8 carbon atoms; $R_2$ represents a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; $R_4$ to $R_7$ represent, respectively and independently, a hydrogen atom, a hydroxyl group, a straight-chain or branched-chain alkyl group having 1 to 10 carbon atoms, a straight-chain or branched-chain alkoxy group having 1 to 10 carbon atoms, a straight-chain or branched-chain alkenyl group having 2 to 10 carbon atoms, a straight-chain or branched-chain alkenyloxy group having 2 to 10 carbon atoms, an aryl group having 5 to 8 carbon atoms, an aryloxy group having 5 to 8 carbon atoms, or an aralkyloxy group having 7 to 9 carbon atoms; $R_8$ and $R_9$ represent, respectively and independently, a hydrogen atom, an alkyl group having 1 to 10 carbon atoms, an alkenyl group having 2 to 10 carbon atoms, an aralkyl group having 7 to 9 carbon atoms, or an acyl group having 2 to 12 carbon atoms; and $R_{10}$ represents a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms;

(15) A quinolinone derivative and physiological salt of the same according to (13), wherein $R_1$ represents a hydrogen atom; $R_2$ represents a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; $R_4$ to $R_7$ represent, respectively and independently, a hydrogen atom, a hydroxyl group, a straight-chain or branched-chain alkyl group having 1 to 10 carbon atoms, a straight-chain or branched-chain alkoxy group having 1 to 10 carbon atoms, a straight-chain or branched-chain alkenyl group having 2 to 10 carbon atoms, a straight-chain or branched-chain alkenyloxy group having 2 to 10 carbon atoms, an aryl group having 5 to 8 carbon atoms, an aryloxy group having 5 to 8 carbon atoms, or an aralkyloxy group having 7 to 9 carbon atoms; $R_8$ and $R_9$ represent, respectively and independently, a hydrogen atom, an alkyl group having 1 to 10 carbon atoms, an alkenyl group having 2 to 10 carbon atoms, an aralkyl group having 7 to 9 carbon atoms, or an acyl group having 2 to 12 carbon atoms; and $R_{10}$ represents a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms;

(16) A quinolinone derivative and physiological salt of the same according to (13), wherein $R_1$ represents either a hydrogen atom, or a straight-chain or branched-chain alkyl group having 1 to 9 carbon atoms; and $R_2$ represents a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; and

(17) A medicament containing, as the active ingredients, a quinolinone derivative and/or physiological salt of the same according to one of (13) to (16).

(18) An anti-allergic agent containing, as the active ingredients, a quinolinone derivative and/or physiological salt of the same according to one of (13) to (16).

(19) A method of treating allergic diseases of mammals, the method comprising administering a pathologically effective amount of quinolinone derivative or physiologically acceptable salt thereof according to one of (13) to (16).

DESCRIPTION OF THE PREFERRED EMBODIMENTS

In the following, the preferred embodiments of the present invention will be described in detail.

In general formula (I) of the present invention, $R_1$ represents a hydrogen atom, an alkyl group, an alkyl group containing a hydroxyl group, an alkenyl group, or an aryl group; and $R_2$ represents an alkyl group, an alkenyl group, an aryl group, or an aralkyl group.

As for $R_1$, the alkyl group may be either a straight-chain or branched-chain alkyl group, examples of which include a methyl group, ethyl group, propyl group, isopropyl group, n-butyl group, s-butyl group, n-pentyl group, hexyl group, n-heptyl group, octyl group, and the like. The alkyl group should preferably have 1 to 9 carbon atoms, more preferably 1 to 7 carbon atoms.

The alkyl group containing a hydroxyl group may be either a straight-chain or branched-chain alkyl group, examples of which may include a compound containing one hydroxyl group such as a hydroxymethyl group, 2-hydroxyethyl group, 3-hydroxypropyl group, 4-hydroxybutyl group, 6-hydroxypentyl group, 1-hydroxyetyl group, and the like, and a compound containing two hydroxyl groups such as a 1,2-dihydroxyethyl group, 2,3-dihydroxypropyl group, and the like.

The alkenyl group may be either a straight-chain or branched-chain alkenyl group, examples of which include a vinyl group, propenyl group, hexenyl group, octenyl group, prenyl group, and the like. The alkenyl group should preferably have 2 to 9 carbon atoms, and more preferably 3 to 7 carbon atoms. Examples of the aryl group may include a furyl group, pyridyl group, phenyl group, and substituted phenyl group. Examples of the substituted phenyl group may include a p-methylphenyl group, p-methoxyphenyl group, p-hydroxyphenyl group, 3,4-dimethoxyphenyl group, and the like. Among the aforementioned, however, a phenyl group is preferred.

Examples of the aralkyl group may include a benzyl group, and a substituted benzyl group (such as a p-methoxybenzyl group, p-hydroxybenzyl group, 3,5-dimethyl benzyl group, and the like); but of the aforementioned a benzyl group is preferred.

As for $R_2$ the alkyl group may be either a straight-chain or branched-chain alkyl group, examples of which include a methyl group, ethyl group, propyl group, isopropyl group, n-butyl group, s-butyl group, n-pentyl group, hexyl group, n-heptyl group, octyl group, n-decyl group, and the like. The alkyl group should preferably have 1 to 10 carbon atoms, and more preferably have 1 to 8 carbon atoms.

The alkenyl group may be either a straight-chain or branched-chain alkenyl group, examples of which include a vinyl group, propenyl group, hexenyl group, octenyl group, geranyl group, and the like. The alkenyl group should preferably have 2 to 10 carbon atoms, and more preferably have 3 to 8 carbon atoms. Examples of the aryl group may include a furyl group, pyridyl group, phenyl group, and a substituted-phenyl group. Examples of the substituted-phenyl group include a p-methylphenyl group, p-methoxyphenyl group, p-hydroxyphenyl group, 3,4-dimethoxyphenyl group, and the like. However, among the aforementioned, a phenyl group is preferred.

Examples of the aralkyl group may include a benzyl group, and substituted benzyl group (such as a p-methoxybenzyl group, p-hydroxybenzyl group, 3,5-dimethyl benzyl group, and the like). However, among the aforementioned, a benzyl group is preferred.

In general formula (I) of the present invention, $R_3$ represents a reactive carboxyl group, more specifically, a carboxyl group that is reactive with a carbon anion. Examples may include a carboxyl group, carboxylic acid ester group, carboxylic acid thioester group, halide carboxylate, and the like; however, among the aforementioned a carboxylic acid ester group is preferred.

In general formula (I) of the present invention, $R_4$ to $R_7$ represent, respectively and independently, a hydrogen atom, a hydroxyl group, an alkyl group, an alkoxy group, an alkenyl group, an alkenyloxy group, an aryl group, an aryloxy group, an aralkyloxy group, a $R_8R_9N$ group (wherein, $R_8$ and $R_9$ represent, respectively and independently, a hydrogen atom, an alkyl group, an alkenyl group, an aralkyl group, or an acyl group), a nitro group, or a $R_{10}OOC$ group (wherein, $R_{10}$ represents a hydrogen atom, an alkyl group, an alkenyl group, an aryl group, or an aralkyl group).

The alkyl group, alkenyl group, aryl group, and aralkyl group represent the same constituents as described above. In addition, the alkyl group, alkenyl group and aralkyl group contained respectively in the alkyloxyl group, alkenyloxyl group, and aralkyloxy group, similarly represent the same constituents as described above.

In general formula (I) of the present invention, the acyl group in $R_8$ and $R_9$ may include both an alkenoyl group represented by an acetyl group, propionyl group, butyryl group, and the like, and a benzoyl group. The benzoyl group may have a substituent group, and examples of such include a p-hydroxybenzoyl group, p-methoxybenzoyl group, 2,4-dihydroxybenzoyl group, 2,4-dimethoxybenzoyl group, and the like.

In addition, a cinnamoyl group and substituted cinnamoyl group may also be included. Examples of the substituted cinnamoyl group include a 2-hydroxycinnamoyl group, 3-hydroxycinnamoyl group, 4-hydroxycinnamoyl group, 3,4-dihydroxycinnamoyl group, 4-hydroxy-3-methoxycinnamoyl group, 3-hydroxy-4-methoxycinnamoyl group, 3,5-dimethoxy-4-hydroxycinnamoyl group, 3,4,5-trimethoxycinnamoyl group, and the like.

In general formula (I) of the present invention, $R_{10}$ represents an alkyl group, an alkenyl group, an aryl group, or an aralkyl group, each of which represents the same constituents as described above.

In the following, a method for preparing the quinolinone derivatives according to the present invention will be explained.

The quinolinone derivatives, expressed by general formula (II) in the present invention, can be prepared by means of the reaction pathway described below.

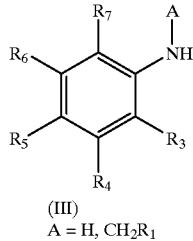
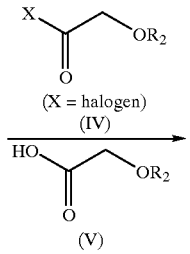
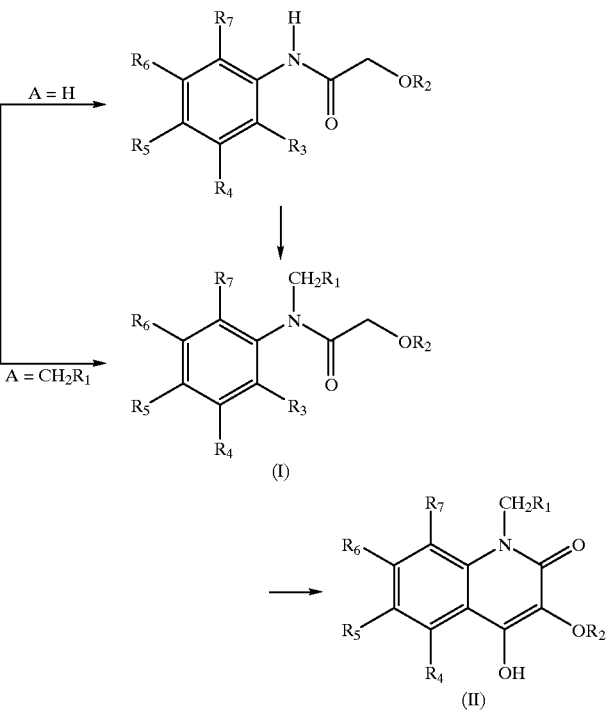

$R_1$ to $R_7$ in the chemical formula of the reaction pathway are defined in the same manner as described above. The preparation method according to the present invention is characterized in that an amide derivative, expressed by general formula (I), and a basic agent are reacted with each other, followed by intramolecular ring formation. The basic agent employed in the present invention may include various compounds such as alkali metals, alkali metal alkoxides, alkaline earth metal alkoxides, alkali metal hydrides, alkaline earth metal hydrides, alkali metal amides, and the like.

Examples of the alkali metal may include sodium, potassium, and the like; Examples of the alkali metal alkoxides may include basic agents such as sodium methoxide, sodium ethoxide, sodium t-butoxide, potassium t-butoxide, and the like; and examples of the alkaline earth metals may include magnesium methoxide, magnesium ethoxide, magnesium t-butoxide, calcium methoxide, calcium ethoxide, calcium t-butoxide, barium methoxide, barium ethoxide, barium t-butoxide, and the like.

Examples of the alkali metal hydrides may include lithium hydride, sodium hydride, potassium hydride, and the like; and examples of the alkaline earth metal hydride may include calcium hydride, and the like. In addition, examples of the alkali metal amides may include lithium amide, sodium amide, potassium amide, lithium diisopropylamide, lithium bis(trimethylsilyl) amide, sodium bis(trimethylsilyl) amide, potassium bis(trimethylsilyl) amide, and the like.

Among these, alkali metal alkoxides and alkali metal amides are especially preferred as a basic agent.

In addition, the amount of the basic agent necessary for ring formation is generally 1 to 5 times, preferably 2 to 3 times, greater in moles than an amide derivative with which a basic agent is reacted. For example, when sodium hydride, potassium t-butoxide, or lithium diisopropylamide is used as a basic agent, the amount of 2 times greater in moles than an amide derivative is, in general, sufficient.

However, even if a compound, in which a hydrogen atom is substituted for a nitrogen atom, is used at 4 times greater in moles than the amide derivative, ring formation does not occur as intended. Thus, it is critical that $R_1$ comprise the substituent group according to the present invention described above. For example, if 2-[(methoxyacetyl)amino]-4-nitro-benzoic ether is reacted with 4 times the amount in moles of sodium hydride in THF, ring formation does not occur.

On the other hand, when $R_1$ is a methyl group, that is, a compound in which an ethyl group is substituted at the position of a nitrogen atom (ethyl 2-[N-ethyl-(methoxyacetyl)amino]-4-nitro-benzoate), a desired quinolinone derivative can be obtained efficiently by means of using 2 times the amount in moles of sodium hydride under the same conditions. When $R_2$ is a hydrogen atom, ring formation does not occur as intended.

Reactions in the preparation method according to the present invention may occur in an organic solvent that does not hinder such reactions. Examples of the organic solvent may include hydrocarbon solvents such as a benzene, toluene, and the like; alcohol solvents such as a methanol, ethanol, propanol, isopropanol, t-butanol, and the like; ethers solvents such as a diethylether, tetrahydrofuran, 1,2-dimethoxyethane, and the like; and amide solvents such as a N,N-dimethylformamide, 1-methyl-2-pyrrolidine, and the like.

The preferable organic solvent differs depending on the type of basic agent employed. For example, alcohol solvents are generally preferred when using alkali metal alkoxides, whereas ammonia can be used as a solvent in case of alkali metal amides such as lithium amide, sodium amide, and potassium amide.

The reaction temperature differs depending on the type of basic agent and reaction solvent employed, but is generally between $-80°$ C. to $100°$ C., and preferably $-50°$ C. to $50°$ C. The reaction time is usually 1 to 5 hours.

The amide derivative of the present invention can be prepared by means of amidation of an amine derivative, expressed by general formula (III). Provided that, if A represents a hydrogen atom in the amine derivative, expressed by general formula (III), the amide derivative, expressed by general formula (I), is prepared by amidation, followed by alkylation. Substituent groups of $R_4$ to $R_7$ of the amide derivative, expressed by general formula (I), may be previously introduced into the amine derivative, or may be introduced after amidation of the amine derivative, expressed by general formula (III). For example, ethyl 2-[N-methyl-(octyloxyacetyl)amino]-4-] (3,5-dimethoxy-4-hydroxycinnamoyl)aminobenzoate can be prepared by reacting ethyl 2-[N-methyl-(octyloxyacetyl)amino] 4-aminobenzoate with 3,5-dimethoxy-4-hydroxycinnamic acid.

Amidation agents for amine derivatives may include either a carboxylic halide, expressed by general formula (IV), or a carboxylic acid, expressed by general formula (V).

Reactions are preferably promoted in an organic solvent in case of using the halide carboxylate, expressed by general formula (IV). Examples of the organic solvents employed may include hydrocarbon solvents such as benzene, toluene, xylene, and the like; ethers solvents such as a diethylether, tetrahydrofuran, 1,2-dimethoxyethane, and the like; and amide solvents such as a N,N-dimethylformamide, 1-methyl-2-pyrrolidine, and the like.

In addition, although it is not particularly necessary to add an agent which promotes the above reaction, it is possible to add an amine, as a catalyst, for example, a basic agent such as a triethylamine, pyridine, and the like. The reaction time differs depending on the type of reagents employed and the reaction temperature, but is usually 30 minutes to 3 hours. The reaction temperature is $-10°$ C. to $10°$ C., and preferably $0°$ C. to $50°$ C. Examples of the halide carboxylate employed may include a chloride, bromide, and iodide; however, among the aforementioned a chloride is preferred.

Furthermore, the desired amide derivative, expressed by general formula (I), can be obtained by means of reacting with a carboxylic acid derivative, expressed by general formula (V). In such a case, the desired amide derivative can be obtained by means of promoting reactions in an organic solvent, in the presence of an acid catalyst. Preferred organic solvents include hydrocarbon solvents such as benzene, toluene, xylene, and the like.

Examples of the acid catalyst preferably include acids which are used in conventional amide synthesis via dehydration, including mineral acids such as hydrochloric acid, sulfuric acid, and the like, and organic acids such as paratoluene sulfonate, methane sulfonate, triphloromethane sulfonate, and the like. It is desirable to allow this reaction to occur while removing water, formed during the reaction, from the group. The reaction time differs depending on the type of reagents employed and the reaction temperature, but is usually 1 to 10 hours. The reaction temperature is $50°$ C. to $140°$ C., and preferably $90°$ C. to $120°$ C.

The novel amide derivative according to the present invention is expressed by general formula (I).

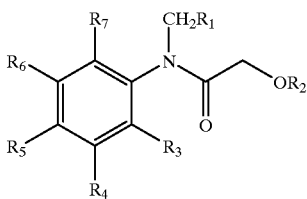

(I)

[wherein, $R_1$ represents a hydrogen atom, an alkyl group, an alkyl group containing a hydroxyl group, an alkenyl group, or an aryl group; $R_2$ represents an alkyl group, an alkenyl group, an aryl group, or an aralkyl group; $R_3$ represents an oxycarboxyl group; $R_4$, $R_5$ and $R_7$ each represents a hydrogen atom; and $R_6$ represents either a $R_8R_9N$ group (wherein, $R_8$ and $R_9$ represent, respectively and independently, a hydrogen atom, an alkyl group, an alkenyl group, an aralkyl group, or an acyl group), or a nitro group].

Specifically, an amide derivative, expressed by the above formula, is provided wherein, $R_1$ is a hydrogen atom, a straight-chain or branched chain alkyl group having 1 to 9 carbon atoms, a straight-chain or branched chain alkyl group containing a hydroxyl group and having 1 to 5 carbon atoms, a straight-chain or branched chain alkenyl group having 2 to 9 carbon atoms, or an aryl group having 5 to 8 carbon atoms; $R_2$ is a straight-chain or branched chain alkyl group having 1 to 10 carbon atoms, a straight-chain or branched chain alkenyl group having 2 to 10 carbon atoms, an aryl group having 5 to 8 carbon atoms, or an aralkyl group having 7 to 9 carbon atoms; and $R_8$ and $R_9$ are, respectively and independently, a hydrogen atom, an alkyl group having 1 to 10 carbon atoms, an alkenyl group having 2 to 10 carbon atoms, an aralkyl group having 7 to 9 carbon atoms, or an acyl group having 2 to 12 carbon atoms.

Alternatively, an amide derivative, expressed by the above formula, is provided wherein $R_1$ is a hydrogen atom; $R_2$ is a straight-chain or branched chain alkyl group having 1 to 10 carbon atoms, a straight-chain or branched chain alkenyl group having 2 to 10 carbon atoms, an aryl group having 5 to 8 carbon atoms, or an aralkyl group having 7 to 9 carbon atoms; and $R_8$ and $R_9$ are, respectively and independently, a hydrogen atom, an alkyl group having 1 to 10 carbon atoms, an alkenyl group having 2 to 10 carbon atoms, an aralkyl group having 7 to 9 carbon atoms, or an acyl group having 2 to 12 carbon atoms.

More specifically, an amide derivative, expressed by the above formula, is provided wherein $R_1$ is either a hydrogen atom, or a straight-chain or branched-chain alkyl group having 1 to 9 carbon atoms; and $R_2$ is a straight-chain or branched chain alkyl group having 1 to 10 carbon atoms, a straight-chain or branched chain alkenyl group having 2 to 10 carbon atoms, an aryl group having 5 to 8 carbon atoms, or an aralkyl group having 7 to 9 carbon atoms.

The following compounds are illustrative examples of the thus obtained amide derivatives represented by the formula (I) of the present invention.

Methyl 2-[N-methyl-N-(methoxyacetyl)amino]-4-nitrobenzoate,

Ethyl 2-[N-methyl-N-(methoxyacetyl)amino]-4-nitrobenzoate, Methyl 2-[N-methyl-N-(ethoxyacetyl)amino]-4nitrobenzoate, Ethyl 2 -[N-methyl-N-(propoxyacetyl)amino]-4-nitrobenzoate, Ethyl 2-[N-methyl-N-(butoxyacetyl)amino]-4-nitrobenzoate, Ethyl 2-[N-methyl-N-(hexyloxyacetyl)amino]-4-nitrobenzoate, Ethyl 2-[N-methyl-N-(octyloxyacetyl) amino]-4-nitrobenzoate, Ethyl 2-[N-methyl-N-(decyloxyacetyl)amino]-4-nitrobenzoate, Ethyl 2-[N-methyl-N-[(2-propenyloxy)acetyl]amino]-4-nitrobenzoate, Ethyl 2-[N-methyl-N-[(3-butenyloxy)acetyl]amino]-4-nitrobenzoate, Ethyl 2-[N-methyl-N-[(5-hexenyloxy)acetyl]amino]-4-nitrobenzoate, Ethyl 2-[N-methyl-N-(geranyloxyacetyl) amino]-4-nitrobenzoate, Ethyl 2-[N-methyl-N-(phenoxyacetyl)amino]-4-nitrobenzoate, Ethyl 2-[N-methyl-N-[(4-methoxyphenoxy)acetyl]amino]-4-nitrobenzoate, Ethyl 2-[N-methyl-N-[(4-hydroxyphenoxy)acetyl]amino]-4-nitrobenzoate, Ethyl 2-[N-methyl-N-[(3,4-dimethylphenoxy)acetyl] amino]-4-nitrobenzoate, Ethyl 2-[N-methyl-N-(benzyloxyacetyl)amino]-4-nitrobenzoate, Ethyl 2-[N-methyl-N-[(4-hydroxybenzyloxy) acetyl]amino]-4-nitrobenzoate, Ethyl 2-[N-methyl-N-[(3,4-dimethylbenzyloxy) acetyl]amino]-4-nitrobenzoate, Methyl 2-[N-ethyl-N-(methoxyacetyl)amino]-4-nitrobenzoate, Methyl 2-[N-ethyl-N-(ethoxyacetyl)amino]-4-nitrobenzoate, Ethyl 2-[N-ethyl-N-(propoxyacetyl) amino]-4-nitrobenzoate, Ethyl 2-[N-ethyl-N-(butoxyacetyl)amino]-4-nitrobenzoate, Ethyl 2-[N-propyl-N-(hexyloxyacetyl)amino]-4-nitrobenzoate, Ethyl 2-[N-propyl-N-(octyloxyacetyl)amino]-4-nitrobenzoate, Ethyl 2-[N-propyl-N-[(2-propenyloxy)acetyl] amino]-4-nitrobenzoate, Ethyl 2-[N-butyl-N-[(3-butenyloxy) acetyl]amino]-4-nitrobenzoate, Ethyl 2-[N-butyl-N-[(5-hexenyloxy) acetyl]amino]-4-nitrobenzoate, Ethyl 2-[N-butyl-N-(geranyloxyacetyl)amino]-4-nitrobenzoate, Ethyl 2-[N-butyl-N-(phenoxyacetyl)amino]-4-nitrobenzoate, Ethyl 2-[N-butyl-N-[(4-methoxyphenoxy)acetyl] amino]-4-nitrobenzoate, Ethyl 2-[N-butyl-N-[(4-hydoroxyphenoxy)acetyl]amino]-4-nitrobenzoate, Ethyl 2-[N-hexyl-N-(benzyloxyacetyl)amino]-4-nitrobenzoate, Ethyl 2-[N-octyl-N-[(4-hydroxybenzyloxy)acetyl] amino]-4-nitrobenzoate, Ethyl 2-[N-decyl-N-(butoxyacetyl)amino]-4-nitrobenzoate, Methyl 2-[N-(2-propenyl)-N-(ethoxyacetyl)amino]-4-nitrobenzoate, Ethyl 2-[N-(3-butenyl)-N-(propoxyacetyl) amino]-4-nitrobenzoate, Ethyl 2-[N-(5-hexenyl)-N-(butoxyacetyl)amino]-4-nitrobenzoate, Ethyl 2-[N-(2-propenyl)-N-(hexyloxyacetyl)amino]-4-nitrobenzoate, Ethyl 2-[N-geranyl-N (ethoxyacetyl)amino]-4-nitrobenzoate, Ethyl 2-[N-prenyl-N-[(5-hexenyloxy) acetyl]amino]-4-nitrobenzoate, Ethyl 2-[N-benzyl-N-(benzyloxyacetyl)amino]-4-nitrobenzoate, Ethyl 2-[N-benzyl-N-[(4-hydroxybenzyloxy)acetyl]amino]-4-nitrobenzoate, Ethyl 2-[N-(2-propenyl)-N-(methoxyacetyl)amino]-4-nitrobenzoate, Methyl 2-[N-methyl-N-(ethoxyacetyl) amino]-4aminobenzoate, Ethyl 2-[N-methyl-N-(propoxyacetyl)amino]-4-aminobenzoate Ethyl 2-[N-methyl-N-(butoxyacetyl)amino]-4-aminobenzoate, Ethyl 2-[N-methyl-N-(hexyloxyacetyl) amino]-4-aminobenzoate, Ethyl 2-[N-methyl-N-(octyloxyacetyl)amino]-4-aminobenzoate, Ethyl 2-[N-methyl-N-[(2-propenyloxy)acetyl]amino]-4-aminobenzoate, Ethyl 2-[N-methyl-N-[(3-butenyloxy)acetyl]amino]-4-aminobenzoate, Ethyl 2-[N-methyl-N-[(5-hexenyloxy)acetyl]amino]-4-aminobenzoate, Ethyl 2-[N-methyl-N-(geranyloxyacetyl)amino]-4-aminobenzoate, Ethyl 2-[N-methyl-N-(phenoxyacetyl)amino]-4-aminobenzoate, Ethyl 2-[N-methyl-N-[(4-methoxyphenoxy)acetyl]amino]-4-aminobenzoate, Ethyl 2-[N-methyl-N-[(4-hydroxyphenoxy)acetyl]amino]-4-aminobenzoate, Ethyl 2-[N-methyl-N-(benzyloxyacetyl)amino]-4-aminobenzoate, Ethyl 2-[N-methyl-N-[(4-hydroxybenzyloxy)acetyl]amino]-4-aminobenzoate, Methyl 2-[N-ethyl-N-(methoxyacetyl)amino]-4-aminobenzoate, Methyl 2-[N-ethyl-N-(ethoxyacetyl)amino]-4-aminobenzoate, Ethyl 2-[N-ethyl-N-(propoxyacetyl)amino]-4-aminobenzoate, Ethyl 2-[N-ethyl-N-(butoxyacetyl)amino]-4-aminobenzoate, Ethyl 2-[N-propyl-N-(hexyloxyacetyl)amino]-4-aminobenzoate, Ethyl 2-[N-propyl-N-(octyloxyacetyl)amino]-4-aminobenzoate, Ethyl 2-[N-propyl-N-[(2-propenyloxy)acetyl]amino]-4-aminobenzoate, Ethyl 2-[N-butyl-N-[(3-butenyloxy)acetyl]amino]-4-aminobenzoate, Ethyl 2-[N-butyl-N-[(5-hexenyloxy)acetyl]amino]-4-aminobenzoate, Ethyl 2-[N-butyl-N-(geranyloxyacetyl)amino]-4-aminobenzoate, Ethyl 2-[N-butyl-N-(phenoxyacetyl)amino]-4-aminobenzoate, Ethyl 2-[N-butyl-N-[(4-methoxyphenoxy)acetyl]amino]-4-aminobenzoate, Ethyl 2-[N-butyl-N-[(4-hydroxyphenoxy)acetyl]aminol]-4-aminobenzoate, Ethyl 2-[N-hexyl-N-(benzyloxy acetyl)amino]-4-aminobenzoate, Ethyl 2-[N-octyl-N-[(4-hydroxybenzyloxy)acetyl]amino]-4-aminobenzoate, Methyl 2-[N-(2-propenyl)-(ethoxyacetyl)amino]-4-aminobenzoate, Ethyl 2-[N-(3-butenyl)-N-(propoxyacetyl)amino]-4-aminobenzoate, Ethyl 2-[N-(5-hexenyl)-N-(butoxyacetyl)amino]-4-aminobenzoate, Ethyl 2-[N-(2-propenyl)-N-(hexyloxyacetyl)amino]-4-aminobenzoate, Ethyl 2-[N-geranyl-N-(octyloxyacetyl)amino]-4-aminobenzoate, Ethyl 2-[N-prenyl-N-[(5-hexenyloxy)acetyl]amino]-4-aminobenzoate, Ethyl 2-[N-benzyl-N-[(4-hydroxybenzyloxy)acetyl]amino]-4-aminobenzoate, Methyl 2-[N-(2-hydroxyethyl)-N-(methoxyacetyl)amino]-4-aminobenzoate, Methyl 2-[N-methyl-N-(methoxyacetyl)amino]-4-hexylaminobenzoate, Methyl 2-[N-methyl-N-(ethoxyacetyl)amino]-4-hexylaminobenzoate, Ethyl 2-[N-methyl-N-(propoxyacetyl)amino]-4-hexylaminobenzoate, Ethyl 2-[N-methyl-N-(butoxyacetyl)amino]-4-hexylaminobenzoate, Ethyl 2-[N-methyl-N-(hexyloxyacetyl)amino]-4-hexylaminobenzoate, Ethyl 2-[N-methyl-N-(octyloxyacetyl)amino]-4-hexylaminobenzoate, Ethyl 2-[N-methyl-N-[(2-propenyloxy)acetyllamino]-4-hexylaminobenzoate, Ethyl 2-[N-methyl-N-[(3-butenyloxy)acetyl]amino]-4-octylaminobenzoate, Ethyl 2-[N-methyl-N-(methoxyacetyl)amino]-4-decylaminobenzoate, Ethyl 2-[N-methyl-N-[(5-hexenyloxy)acetyl]amino]-4-octylaminobenzoate, Ethyl 2-[N-methyl-N-(geranyloxyacetyl)amino]-4-octylaminobenzoate, Ethyl 2-[N-methyl-N-(phenoxyacetyl)amino]-4-octylaminobenzoate, Ethyl 2-[N-methyl-N-[(4-methoxyphenoxy)acetyl]amino]-4-octylaminobenzoate, Ethyl 2-[N-methyl-N-[(hydroxyphenoxy)acetyl]amino]-4-octylaminobenzoate, Ethyl 2-[N-methyl-N-(methoxyacetyl)amino]-4-vinylaminobenzoate, Ethyl 2-[N-methyl-N-(benzyloxyacetyl)amino]-4-(2-propenyl)aminobenzoate, Ethyl 2-[N-methyl-N-[(4-hydroxybenzyloxy)acetyl]amino]-4-(2-propenyl)aminobenzoate, Methyl 2-[N-ethyl-N-(methoxyacetyl)amino]-4-(5-hexenyl)aminobenzoate, Methyl 2-[N-ethyl-N-(ethoxyacetyl)amino]-4-(5-hexenyl)aminobenzoate, Ethyl 2-[N-ethyl-N-(propoxyacetyl)amino]-4-(5-hexenyl)aminobenzoate, Ethyl 2-[N-ethyl-N-(butoxyacetyl)amino]-4-(5-hexenyl)aminobenzoate, Ethyl 2-[N-propyl-N-(hexyloxyacetyl)amino]-4-(5-hexenyl)aminobenzoate, Ethyl 2-[N-propyl-N-(octyloxyacetyl)amino]-4-(5-hexenyl)aminobenzoate, Ethyl 2-[N-propyl-N-[(2-propenyloxy)acetyl]amino]-4-(5-hexenyl)aminobenzoate, Ethyl 2-[N-butyl-N-[(3-butenyloxy)acetyl]amino]-4-(5-hexenyl)aminobenzoate, Ethyl 2-[N-butyl-N-[(5-hexenyloxy)acetyl]amino]-4-(5-hexenyl)aminobenzoate, Ethyl 2-[N-butyl-N-(geranyloxyacetyl)amino]-4-(5-hexenyl)aminobenzoate, Ethyl 2-[N-butyl-N-(phenoxyacetyl)amino]-4-(5-hexenyl)aminobenzoate Ethyl 2-[N-butyl-N-[(4-methoxyphenoxy)acetyl]amino]-4-(5-hexenyl)aminobenzoate, Ethyl 2-[N-butyl-N-[(4-hydroxyphenoxy)acetyl]amino]-4-geranylaminobenzoate, Ethyl 2-[N-hexyl-N-(benzyloxyacetyl)amino]-4-geranylaminobenzoate, Ethyl 2-[N-octyl-N-[(4-hydroxybenzyloxy)acetyl]amino]-4-geranylaminobenzoate, Methyl 2-[N-methyl-N-(methoxyacetyl)amino]-4-acetylaminobenzoate, Methyl 2-[N-methyl-N-(ethoxyacetyl)amino]-4-acetylaminobenzoate, Ethyl 2-[N-methyl-N-(propoxyacetyl)amino]-4-acetylaminobenzoate, Ethyl 2-[N-methyl-N-(butoxyacetyl)amino]-4-acetylaminobenzoate, Ethyl 2-[N-methyl-N-(hexyloxyacetyl)amino]-4-acetylaminobenzoate, Ethyl 2-[N-methyl-N-(octyloxyacetyl)amino]-4-acetylaminobenzoate, Ethyl 2-[N-methyl-N-[(2-propenyloxy)acetyl]amino]-4-acetylaminobenzoate, Ethyl 2-[N-methyl-N-[(3-butenyloxy)acetyl]amino]-4-acetylaminobenzoate, Ethyl 2-[N-methyl-N-[(5-hexenyloxy)acetyl]amino]-4-acetylaminobenzoate, Ethyl 2-[N-methyl-N-(geranyloxyacetyl)amino]-4-acetylaminobenzoate, Ethyl 2-[N-methyl-N-(phenoxyacetyl)amino]-4-acetylaminobenzoate, Ethyl 2-[N-methyl-N-[(4-methoxyphenoxy)acetyl]amino]-4-acetylaminobenzoate, Ethyl 2-[N-methyl-N-[(4-hydroxyphenoxy)acetyl]amino]-4-acetylaminobenzoate, Ethyl 2-[N-methyl-N-(benzyloxy acetyl)amino]-4-(2-propenyl)aminobenzoate, Ethyl 2-[N-methyl-N-[(4-hydroxybenzyloxy)acetyl]amino]-4-acetylaminobenzoate, Methyl 2-[N-(2-propenyl)-N-(ethoxyacetyl)amino]-4-acetylaminobenzoate, Ethyl 2-[N-(3-butenyl)-N-(propoxyacetyl)amino]-4-acetylaminobenzoate, Ethyl 2-[N-(5-hexenyl)-(butoxyacetyl)amino]-4-acetylaminobenzoate, Ethyl 2-[N-(2-propenyl)-N-(hexyloxyacetyl)amino]-4-acetylaminobenzoate, Ethyl 2-[N-methyl-N-(octyloxyacetyl)amino]-4-benzoylaminobenzoate, Ethyl 2-[N-geranyl-N-(octyloxyacetyl)amino]-4-benzoylaminobenzoate, Ethyl 2-[N-prenyl-N-[(5-hexenyloxy)acetyl]amino]-4-benzoylaminobenzoate, Ethyl 2-[N-geranyl-N-(ethoxyacetyl)amino]-4-aminobenzoate, Ethyl 2-[N-methyl-N-(methoxyacetyl)amino]-4-benzylaminobenzoate, Ethyl 2-[N-benzyl-N-(benzyloxyacetyl)amino]-4-benzylaminobenzoate, Ethyl 2-[N-benzyl-N-[(4-hydroxybenzyloxy)acetyl]amino]-4-benzylaminobenzoate, Methyl 2-[N-methyl-N-

(methoxyacetyl)amino]-4-cinnamoylaminobenzoate, Methyl 2-[N-methyl-N-(ethoxyacetyl)amino]-4-cinnnamoylaminobenzoate, Ethyl 2-[N-methyl-N-(propoxyacetyl)amino]-4-(3,5-dimethoxy-4-hydroxycinnamoyl)aminobenzoate, Ethyl 2-[N-methyl-N-(butoxyacetyl)amino]-4-(3,5-dimethoxy-4-hydroxycinnamoyl)aminobenzoate, Ethyl 2-[N-methyl-N-(hexyloxyacetyl)amino]-4-(3,5-dimethoxy-4-hydroxycinnamoyl)aminobenzoate, Ethyl 2-[N-methyl-N-(octyloxyacetyl)amino]-4-[(3,5-dimethoxy-4-hydroxycinnamoyl)amino]-benzoate, Ethyl 2-[N-methyl-N-[(2-propenyloxy)acetyl]amino]-4-(4-hydroxycinnamoyl)aminobenzoate, Ethyl 2-[N-methyl-N-[(3-butenyloxy)acetyl]amino]-4-(3,4-dihydroxycinnamoyl)aminobenzoate, Ethyl 2-[N-methyl-N-[(5-hexenyloxy)acetyl]amino]-4-(3-hydroxycinnamoyl)aminobenzoate, Ethyl 2-[N-methyl-N-(geranyloxyacetyl)amino]-4-(3,5-dimethoxy-4-hydroxycinnamoyl)aminobenzoate, Methyl 2-[N-methyl-N-(methoxyacetyl)amino]-4-(N-methyl-N-acetyl)aminobenzoate, Methyl 2-[N-methyl-N-(ethoxyacetyl)amino]-4-(N,N-dimethyl)aminobenzoate, Ethyl 2-[N-methyl-N-(propoxyacetyl)amino]-4-(N,N-dimethyl)aminobenzoate, Ethyl 2-[N-methyl-N-(butoxyacetyl)amino]-4-(N,N-dimethyl)aminobenzoate, Ethyl 2-[N-methyl-N-(hexyloxyacetyl)amino]-4-(N,N-dimethyl)aminobenzoate, Ethyl 2-[N-methyl-N-(octyloxyacetyl)amino]-4-(N,N-dimethyl)aminobenzoate, Ethyl 2-[N-methyl-N-[(2-propenyloxy)acetyl]amino]-4-(N-methyl-N-acetyl)aminobenzoate, Ethyl 2-[N-methyl-N-[(3-butenyloxy)acetyl]amino]-4-(N-ethyl-N-acetyl)aminobenzoate, Ethyl 2-[N-methyl-N-[(5-hexenyloxy)acetyl]amino]-4-(N-ethyl-N-acetyl)aminobenzoate, Ethyl 2-[N-methyl-N-(geranyloxyacetyl)amino]-4-(N-butyl-N-acetyl)aminobenzoate, Ethyl 2-[N-methyl-N-(phenoxyacetyl)amino]-4-[N-(2-propenyl)-N-acetyl]aminobenzoate, Ethyl 2-[N-methyl-N-[(4-methoxyphenoxy)acetyl]amino]-4-(N-geranyl-N-acetyl)aminobenzoate, Ethyl 2-[N-methyl-[(4-hydroxyphenoxy)acetyl]amino]-4-(N-benzyl-N-acetyl)aminobenzoate, Ethyl 2-[N-methyl-N-(benzyloxy-N-acetyl)amino]-4-(N-methyl-N-benzyl)aminobenzoate, Methyl 2-[N-ethyl-N-(ethoxyacetyl)amino]-4-nitrobenzoate, Methyl 2-[N-decyl-(butoxyacetyl)amino]-4-nitrobenzoate, Methyl 2-[N-methyl-N-(decyloxyacetyl)amino]-4-nitrobenzoate, Methyl 2-[N-methyl-N-(octyloxyacetyl)amino]-4-nitrobenzoate, Methyl 2-[N-(2-puropenyl)-N-(methoxyacetyl)amino]-4-nitrobenzoate, Methyl 2-[N-(2-hydroxyethyl)-N-(methoxyacetyl)amino]-4-nitrobenzoate, Methyl 2-[N-methyl-N-(methoxyacetyl)amino]-4-aminobenzoate, Methyl 2-[N-geranyl-N-(ethoxyacetyl)amino]-4-aminobenzoate, Methyl 2-[N-methyl-N-(octyloxyacetyl)amino]-4-aminobenzoate, Methyl 2-[N-methyl-N-(benzyloxyacetyl)amino]-4-aminobenzoate, Methyl 2-[N-methyl-N-(butoxyacetyl)amino]-4-aminobenzoate, Methyl 2-[N-(3-hydroxypropyl)-N-(methoxyacetyl)amino]-4-aminobenzoate, Methyl 2-[N-methyl-N-(methoxyacetyl)amino]-4-benzylaminobenzoatemethyl, Methyl 2-[N-methyl-N-(octyloxyacetyl)amino]-4-benzylaminobenzoate, Methyl 2-[N-methyl-N-(octyloxyacetyl)amino]-4-acetylaminobenzoate, Methyl 2-[N-methyl-N-(benzyloxyacetyl)amino]-4-methylaminobenzoate, Methyl 2-[N-ethyl-N-(3,4-dimethylbenzyloxy)acetyl]amino]-4-hexylaminobenzoate, Methyl 2-[N-methyl-N-(octyloxyacetyl)amino]-4-(N,N-dimethyl)aminobenzoate, Methyl 2-[N-methyl-N-(methoxyacetyl)amino]-4-decylaminobenzoate, Methyl 2-[N-methyl-N-(methoxyacetyl)amino]-4-vinylaminobenzoate, Methyl 2-[N-methyl-N-(benzyloxyacetyl)amino]-4-hexylaminobenzoate, Ethyl 2-[N-methyl-N-(octyloxyacetyl)amino]-4-(N,N-dimethyl)aminobenzoate, Ethyl 2-[N-methyl-N-(methoxyacetyl)amino]-4-geranylaminobenzoate, Ethyl 2-[N-methyl-N-(octyloxyacetyl)amino]-4-[(3, 4, 5-trimethoxycinnamoyl)amino]-benzoate, Ethyl 2-[N-methyl-(2-pyridyloxy)acetyl]amino]-4-nitrobenzoate, Ethyl 2-[N-(2-furanyl)methyl-N-methoxyacetyl]amino]-4-nitrobenzoate, Ethyl 2-[N-methyl-N-(butoxyacetyl)amino]-6-phenoxycarbonylbenzoate, Ethyl 2-[N-methyl-N-(butoxyacetyl)amino]-6-decyloxycarbonylbenzoate, Ethyl 2-[N-(3,5-dimethylbenzyloxy)-N-ethoxyscetyl]amino]-6-hexylaminobenzoate.

These are using synthetic intermediate of useful quinolinone derivatives as medicine, especially anti-allergic agent.

The novel quinolinone derivative, obtained by means of the preparation method according to the present invention, is a quinolinone derivative, expressed by general formula (II).

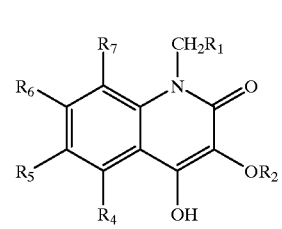

(II)

[wherein, $R_1$ represents a hydrogen atom, an alkyl group, an alkyl group containing a hydroxyl group, an alkenyl group, or an aryl group; $R_2$ represents an alkyl group, an alkenyl group, an aryl group, or an aralkyl group; and $R_4$ to $R_7$ represent, respectively and independently, a hydrogen atom, a hydroxyl group, an alkyl group, an alkoxy group, an alkenyl group, an alkenyloxy group, an aryl group, an aryloxy group, an aralkyloxy group, a $R_8R_9N$ group (wherein, $R_8$ and $R_9$ represent, respectively and independently, a hydrogen atom, an alkyl group, an alkenyl group, an aralkyl group, or an acyl group), a nitro group, or a $R_{10}OOC$ group (wherein, $R_{10}$ represents a hydrogen atom, an alkyl group, an alkenyl group, an aryl group, or an aralkyl group)]; with the exception that the following two types of compounds are not included: (i) a compound in which $R_4$, $R_5$ and $R_7$ are respectively hydrogen atoms; and $R_6$ is selected from the group comprising a hydrogen atom, a hydroxyl group, an alkoxy group, an alkenyloxy group, an aralkyloxy group, a $R_8R_9N$ group (wherein, $R_8$ and $R_9$ represent, respectively and independently, a hydrogen atom, an alkyl group, an alkenyl group, an aralkyl group, or an acyl group), and a nitro group; and (ii) a compound in which $R_4$, $R_5$ and $R_6$ are respectively hydrogen atoms, and $R_7$ is a methoxy group.

Specifically, a quinolinone derivative, expressed by the above formula, is provided wherein $R_1$ is a hydrogen atom, a straight-chain or branched-chain alkyl group having 1 to 9 carbon atoms, a straight-chain or branched-chain alkyl group containing a hydroxyl group and having 1 to 5 carbon atoms, a straight-chain or branched-chain alkenyl group having 2 to 9 carbon atoms, or an aryl group having 5 to 8 carbon atoms; $R_2$ is a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; $R_4$ to $R_7$ are, respectively and independently, a hydrogen atom, a hydroxyl group, a straight-chain or branched-chain alkyl group having 1 to 10 carbon atoms, a straight-chain or branched-chain alkoxy group having 1 to 10 carbon atoms, a straight-chain or branched-chain alkenyl group having 2 to 10 carbon atoms, a straight-chain or branched-chain alkenyloxy group having 2 to 10 carbon atoms, an aryl group having 5 to 8 carbon atoms, an aryloxy group having 5 to 8 carbon atoms, or an aralkyloxy group having 7 to 9 carbon atoms; $R_8$ and $R_9$ are, respectively and independently, a hydrogen atom, an alkyl group having 1 to 10 carbon atoms, an alkenyl group having 2 to 10 carbon atoms, an aralkyl group having 7 to 9 carbon atoms, or an acyl group having 2 to 12 carbon atoms; and $R_{10}$ is a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; with the exception that the following two types of compounds are not included: (i) a compound in which $R_4$, $R_5$ and $R_7$ are respectively hydrogen atoms; and $R_6$ is selected from the group comprising a hydrogen atom, a hydroxyl group, an alkoxy group, an alkenyloxy group, an aralkyloxy group, a $R_8R_9N$ group (wherein, $R_8$ and $R_9$ represent, respectively and independently, a hydrogen atom, an alkyl group, an alkenyl group, an aralkyl group, or an acyl group), and a nitro group; and (ii) a compound in which $R_4$, $R_5$ and $R_6$ are respectively hydrogen atoms, and $R_7$ is a methoxy group.

More specifically, a quinolinone derivative, expressed by the above formula, is provided, wherein $R_1$ is a hydrogen atom; $R_2$ is a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; $R_4$ to $R_7$ are, respectively and independently, a hydrogen atom, a hydroxyl group, a straight-chain or branched-chain alkyl group having 1 to 10 carbon atoms, a straight-chain or branched-chain alkoxy group having 1 to 10 carbon atoms, a straight-chain or branched-chain alkenyl group having 2 to 10 carbon atoms, a straight-chain or branched-chain alkenyloxy group having 2 to 10 carbon atoms, an aryl group having 5 to 8 carbon atoms, an aryloxy group having 5 to 8 carbon atoms, or an aralkyloxy group having 7 to 9 carbon atoms; $R_8$ and $R_9$ are, respectively and independently, a hydrogen atom, an alkyl group having 1 to 10 carbon atoms, an alkenyl group having 2 to 10 carbon atoms, an aralkyl group having 7 to 9 carbon atoms, or an acyl group having 2 to 12 carbon atoms; and $R_{10}$ is a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; with the exception that the following two types of compounds are not included: (i) a compound in which $R_4$, $R_5$ and $R_7$ are respectively hydrogen atoms; and $R_6$ is selected from the group comprising a hydrogen atom, a hydroxyl group, an alkoxy group, an alkenyloxy group, an aralkyloxy group, a $R_8R_9N$ group (wherein, $R_8$ and $R_9$ represent, respectively and independently, a hydrogen atom, an alkyl group, an alkenyl group, an aralkyl group, or an acyl group), and a nitro group; and (ii) a compound in which $R_4$, $R_5$ and $R_6$ are respectively hydrogen atoms, and $R_7$ is a methoxy group.

More specifically, a quinolinone derivative, expressed by the above formula, is provided wherein $R_1$ is either a hydrogen atom, or a straight-chain or branched-chain alkyl group having 1 to 9 carbon atoms; and $R_2$ is a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; with the exception that the following two types of compounds are not included: (i) a compound in which $R_4$, $R_5$ and $R_7$ are respectively hydrogen atoms; and $R_6$ is selected from the group comprising a hydrogen atom, a hydroxyl group, an alkoxy group, an alkenyloxy group, an aralkyloxy group, a $R_8R_9N$ group (wherein, $R_8$ and $R_9$ represent, respectively and independently, a hydrogen atom, an alkyl group, an alkenyl group, an aralkyl group, or an acyl group), and a nitro group; and (ii) a compound in which $R_4$, $R_5$ and $R_6$ are respectively hydrogen atoms, and $R_7$ is a methoxy group.

The following compounds are illustrative examples of the thus obtained quinolinone derivatives represented by the formula (II) of the present invention.

7-nitro-3-methoxy-4-hydroxy-1-ethyl-2(1H)-quinolinone, 5-nitro-3-methoxy-4-hydroxy-1-ethyl-2(1H)-quinolinone, 6-nitro-3-methoxy-4-hydroxy-1-octyl-2(1H)-quinolinone, 7-nitro-3-butoxy-4-hydroxy-1-decyl-2(1H)-quinolinone, 7-nitro-3-butoxy-4-hydroxy-1-propenyl-2(1H)-quinolinone, 7-nitro-3-decyloxy-4-hydroxy-1-methyl-2(1H)-quinolinone, 8-nitro-3-methoxy-4-hydroxy-1-benzyl-2(1H)-quinolinone, 7-nitro-3-octyloxy-4-hydroxy-1-methyl-2(1H)-quinolinone, 7-nitro-3-methoxy-4-hydroxy-1-propenyl-2(1H)-quinolinone, 7-nitro-3-methoxy-4-hydroxy-1-(2-hydroxyethyl)-2(1H)-quinolinone, 6-nitro-3-butoxy-4-hydroxy-1-(6-hydroxyhexyl)-2(1H)-quinolinone, 7-amino-3-methoxy-4-hydroxy-1-methyl-2(1H)-quinolinone, 7-amino-3-ethoxy-4-hydroxy-1-geranyl-2(1H)-quinolinone, 5-amino-3-ethoxy-4-hydroxy-1-methyl-2(1H)-quinolinone, 6-amino-3-phenoxy-4-hydroxy-1-methyl-2(1H)-quinolinone, 8-amino-3-geranyloxy-4-hydroxy-1-methyl-2(1H)-quinolinone, 7-amino-3-octyloxy-4-hydroxy-1-methyl-2(1H)-quinolinone, 6-amino-3-butoxy-4-hydroxy-1-(2-furylmethyl)-2(1H)-quinolinone, 7-amino-3-benzyloxy-4-hydroxy-1-methyl-2(1H)-quinolinone, 7-amino-3-butoxy-4-hydroxy-1-methyl-2(1H)-quinolinone, 7-amino-3-methoxy-4-hydroxy-1-(2-hydroxyethyl)-2(1H)-quinolinone, 7-benzoylamino-3-methoxy-4-hydroxy-1-methyl-2(1H)-quinolinone, 5-acetylamino-3-ethoxy-4-hydroxy-1-methyl-2(1H)-quinolinone, 6-acetylamino-3-phenoxy-4-hydroxy-1-methyl-2(1H)-quinolinone, 8-acetylamino-3-geranyloxy-4-hydroxy-1-methyl-2(1H)-quinolinone, 7-[(4-hydroxy-3,5-dimethoxycinnamoyl)amino]-3-octyloxy-4-hydroxy-1-methyl-2(1H)-quinolinone, 7-[(3,4,5-trimethoxycinnnamoyl)amino]-3-octyloxy-4-hydroxy-1-methyl-2(1H)-quinolinone, 7-acetylamino-3-octyloxy-4-hydroxy-1-methyl-2(1H)-quinolinone, 7-benzoylamino-3-octyloxy-4-hydroxy-1-methyl-2(1H)-quinolinone, 7-methylamino-3-benzyloxy-4-hydroxy-1-methyl-2(1H)-quinolinone, 7-hexylamino-3-(3,4-dimethylbenzyloxy)-4-hydroxy-1-ethyl-2(1H)-quinolinone, 7-dimethylamino-3-octyloxy-4-hydroxy-1-methyl-2(1H)-quinolinone, 7-benzylamino-3-methoxy-4-hydroxy-1-methyl-2(1H)-quinolinone, 7-decylamino-3-methoxy-4-hydroxy-1-methyl-2(1H)-quinolinone, 7-vinylamino-3-methoxy-4-hydroxy-1-methyl-2(1H)-quinolinone, 6-(2-furylmethyl)amino-3-methoxy-4-hydroxy-1-methyl-2(1H)-quinolinone, 6-(2-pyridylmethyl)amino-3-methoxy-4-hydroxy-1-methyl-2(1H)-quinolinone, 6-(3,4-dimethylbenzyl)amino-3-methoxy-4-hydroxy-1-methyl-2(1H)-quinolinone, 6-geranylamino-3-methoxy-4-hydroxy-1-methyl-2(1H)-quinolinone, 5-puropenylamino-3-ethoxy-4-hydroxy-1-methyl-2(1H)-quinolinone, 6-benzylmethylamino-3-phenoxy-4-hydroxy-1-methyl-2(1H)-quinolinone, 8-butylamino-3-geranyloxy-4-hydroxy-1-methyl-2(1H)-quinolinone, 7-hexylamino-3-benzyloxy-4-hydroxy-1-methyl-2(1H)-quinolinone, 7-hydroxy-3-methoxy-4-hydroxy-1-methyl-2(1H)-quinolinone, 5-hydroxy-3-ethoxy-4-hydroxy-1-ethyl-2(1H)-quinolinone, 6-hydroxy-3-phenoxy-4-hydroxy-1-octyl-2(1H)-quinolinone, 8-hydroxy-3-geranyloxy-4-hydroxy-1-benzyl-2(1H)-quinolinone, 7-hydroxy-3-octyloxy-4-hydroxy-1-methyl-2(1H)-quinolinone, 7-hydroxy-3-octyloxy-4-hydroxy-1-propenyl-2(1H)-quinolinone, 7-vinyloxy-3-octyloxy-4-hydroxy-1-methyl-2(1H)-quinolinone, 7-octyloxy-3-methoxy-4-hydroxy-1-methyl-2(1H)-quinolinone, 6-decyloxy-3-methoxy-4-hydroxy-1-methyl-2(1H)-quinolinone, 5-phenoxy-3-ethoxy-4-hydroxy-1-ethyl-2(1H)-quinolinone, 5-geranyloxy-3-ethoxy-4-hydroxy-1-ethyl-2(1H)-quinolinone, 6-propenyloxy-3-phenoxy-4-hydroxy-1-octyl-2(1H)-quinolinone, 8-benzyloxy-3-geranyloxy-4-hydroxy-1-benzyl-2(1H)-quinolinone, 7-methoxy-3-octyloxy-4-hydroxy-1-methyl-2(1H)-quinolinone, 7-butoxy-3-octyloxy-4-hydroxy-1-propenyl-2(1H)-quinolinone, 7-methyl-3-octyloxy-4-hydroxy-1-propenyl-2(1H)-quinolinone, 7-hexyl-3-methoxy-4-hydroxy-1-methyl-2(1H)-quinolinone, 7-decyl-3-methoxy-4-hydroxy-1-methyl-2(1H)-quinolinone, 6-propenyl-3-methoxy-4-hydroxy-1-methyl-2(1H)-quinolinone, 6-geranyl-3-methoxy-4-hydroxy-1-methyl-2(1H)-quinolinone, 7-(3,4-dimethylbenzyl)-3-methoxy-4-hydroxy-1-methyl-2(1H)-quinolinone, 5-butyl-3-ethoxy-4-hydroxy-1-ethyl-2(1H)-quinolinone, 6-phnyl-3-phenoxy-4-hydroxy-1-octyl-2(1H)-quinolinone, 6-propenyl-3-phenoxy-4-hydroxy-1-octyl-2(1H)-quinolinone, 8-methyl-3-geranyloxy-4-hydroxy-1-benzyl-2(1H)-quinolinone, 7-methyl-3-octyloxy-4-hydroxy-1-methyl-2(1H)-quinolinone, 7-butyl-3-octyloxy-4-hydroxy-1-propenyl-2(1H)-quinolinone, 5,7-dihydroxy-3-methoxy-4-hydroxy-1-methyl-2(1H)-quinolinone, 5,7-dihydroxy-3-ethoxy-4-hydroxy-1-ethyl-2(1H)-quinolinone, 5,7-dimethoxy-3-phenoxy-4-hydroxy-1-octyl-2(1H)-quinolinone, 5,7-dibenzyloxy-3-geranyloxy-4-hydroxy-1-benzyl-2(1H)-quinolinone, 5,7-dipuropenyloxy-3-octyloxy-4-hydroxy-1-methyl-2(1H)-quinolinone, 5-ethoxycsrbonyl-3-butoxy-4-hydroxy-1-methyl-2(1H)-quinolinone, 5-phenoxycarbonyl-3-butoxy-4-hydroxy-1-methyl-2(1H)-quinolinone, 5-propenyloxycarbonyl-3-butoxy-4-hydroxy-1-methyl-2(1H)-quinolinone, 5-hydroxycarbonyl-3-octyloxy-4-hydroxy-1-methyl-2(1H)-quinolinone, 7-[(3,5-dimethoxy-4-hydroxycinnamoyl)amino]-3-octyloxy-4-hydroxy-1-methyl-2(1H)-quinolinone, 6-benzylamino-3-phenoxy-4-hydroxy-1-methyl-2(1H)-quinolinone, 6-nitro-3-butoxy-4-hydroxy-1-decyl-2(1H)-quinolinone, 6-nitro-3-butoxy-4-hydroxy-1-(6-hydroxyhexyl)-2(1H)-quinolinone, 5-amino-3-ethoxy-4-hydroxy-1-geranyl-2(1H)-quinolinone, 7-[(3,4,5-trimethoxycinnamoyl)amino]-3-octyloxy-4-hydroxy-1-methyl-2(1H)-quinolinone, 5-methylamino-3-benzyloxy-4-hydroxy-1-methyl-2(1H)-quinolinone, 5-hexylamino-3-(3,5-dimethylbenzyloxy)-4-hydroxy-1-ethyl-2(1H)-quinolinone, 6-decylamino-3-methoxy-4-hydroxy-1-methyl-2(1H)-quinolinone, 6-vinylamino-3-methoxy-4-hydroxy-1-methyl-2(1H)-quinolinone, 6-(3,5-dimethylbenzylamino)-3-methoxy-4-hydroxy-1-methyl-2(1H)-quinolinone, 6-(2-propenyloxy)-3-phenoxy-4-hydroxy-1-octyl-2(1H)-quinolinone, 7-methyl-3-methoxy-4-hydroxy-1-methyl-2(1H)-quinolinone, 6-(2-propenyl)-3-methoxy-4-hydroxy-1-methyl-2-(1H)-quinolinone, 7-butyl-3-octyloxy-4-hydroxy-1-(2-propenyl)-2(1H)-quinolinone, 7-nitro-3-(2-pyridyloxy)-4-hydroxy-1-methyl-2(1H)-quinolinone, 7-nitro-3-methoxy-4-hydroxy-1-(2-furanyl)methyl-2(1H)-quinolinone, 5-phenoxycarbonyl-3-butoxy-4-hydroxy-1-methyl-2(1H)-quinolinone, 5-decyloxycarbonyl-3-butoxy-4-hydroxy-1-methyl-2(1H)-quinolinone, 5-hexylamino-3-ethoxy-4-hydroxy-1-(3,5-dimethylbenzyloxy)-2(1H)-quinolinone 5-nitro-3-octyloxy-4-hydroxy-1-methyl-2(1H)-quinolinone, 6-nitro-3-octyloxy-4-hydroxy-1-methyl-2(1H)-quinolinone, 8-nitro-3-octyloxy-4-hydroxy-1-methyl-2(1H)-quinolinone, 5-amino-3-octyloxy-4-hydroxy-1-methyl-2(1H)-quinolinone, 6-amino-3-octyloxy-4-hydroxy-1-methyl-2(1H)-quinolinone, 8-amino-3-octyloxy-4-hydroxy-1-methyl-2(1H)-quinolinon, 5-[(3,5-dimethoxy-4-hydroxycinnamoyl)amino]-3-octyloxy-4-hydroxy-1-methyl-2(1H)-quinolinone, 6-[(3,5-dimethoxy-4-hydroxycinnamoyl)amino]-3-octyloxy-4-hydroxy-1-methyl-2(1H)-quinolinone, 8-[(3,5-dimethoxy-4-hydroxycinnamoyl)amino]-3-octyloxy-4-hydroxy-1-methyl-2(1H)-quinolinone, 6-hexylamino-5-ethyl-3-butoxy-4-hydroxy-1-methyl-2(1H)-quinolinone, 6-methoxy-3-phenoxy-4-hydroxy-1-octyl-2(1H)-quinolinone, 6-benzyloxy-3-geranyloxy-4-hydroxy-1-benzyl-2(1H)-quinolinone, 6-propenyloxy-3-octyloxy-4-hydroxy-1-methyl-2(1H)-quinolinone, 6-ethoxycarbonyl-3-butoxy-4-hydroxy-1-methyl-2(1H)-quinolinone, 6-phenoxycarbonyl-3-butoxy-4-hydroxy-1-methyl-2(1H)-quinolinone, 6-propenyloxycarbonyl-3-butoxy-4-hydroxy-1-methyl-2(1H)-quinolinone, 6-hydroxycarbonyl-3-octyloxy-4-hydroxy-1-methyl-2(1H)-quinolinone, 8-methoxy-3-phenoxy-4-hydroxy-1-octyl-2(1H)-quinolinone, 8-benzyloxy-3-geranyloxy-4-hydroxy-1-benzyl-2(1H)-quinolinone, 8-propenyloxy-3-octyloxy-4-hydroxy-1-methyl-2 (H 11)-quinolinone 8-ethoxycarbonyl-3-butoxy-4-hydroxy-1-methyl-2(1H)-quinolinone, 8-phenoxycarbonyl-3-butoxy-4-hydroxy-1-methyl-2(1H)-quinolinone, 8-propenyloxycarbonyl-3-butoxy-4-hydroxy 1-methyl-2(1H)-quinolinone, 8-hydroxycarbonyl-3-octyloxy-4-hydroxy-1-methyl-2(1H)-quinolinone, 5-octyloxy-3-methoxy-4-hydroxy-1-methyl-2(1H)-quinolinone, 6-hexyl-3-butoxy-4-hydroxy-1-methyl-2(1H)-quinolinone, 8-hexyloxy-3-hexyloxy-4-hydroxy-1-methyl-2(1H)-quinolinone, 8-octyl-3-butoxy-4-hydroxy-1-methyl-2(1H)-quinolinone, 8-methylamino-3-octyloxy-4-hydroxy-1-methyl-2(1H)-quinolinone, 8-decylamino-3-ethoxy-4-10hydroxy-1-methyl-2(1H)-quinolinone Since the 7-aminoquinolinone derivatives and physiologically acceptable salts of the present invention (to be referred to as "the compound of the present invention" hereinafter) have a function to inhibit both immediate and delayed type allergic reactions and low toxicity as will be described later in examples, they are useful as antiallergic agents for the treatment or prevention of various allergic diseases.

The term "allergic diseases" as used herein means allergic diseases resulting from excess activation of the biological immune mechanism caused by extrinsic or intrinsic antigens, which include immediate type asthma, delayed type asthma, bronchial asthma, pediatric asthma, atopic dermatitis, allergic dermatitis, urticaria, eczema, allergic conjunctivitis, allergic rhinitis, hay fever, food allergy, allergic gastroenteritis, allergic colitis, contact dermatitis, autoimmune disease and the like.

The antiallergic agent which comprises the compound of the present invention as an active ingredient can be administered orally (internal use or inhalation) or parenterally (for example, intravenous injection, subcutaneous injection, percutaneous absorption, rectal administration or the like). Such a pharmaceutical agent can be made into various dosage forms according to the purpose, such as tablets, capsules, granules, fine subtilaes, powders, troches, sublingual tablets, suppositories, ointments, injections, emulsions, suspensions, medicated syrups and the like. These dosage forms can be prepared in accordance with known techniques making use of pharmaceutically acceptable carriers which are commonly used in this type of drugs, such as excipients, bonding agents, disintegrators, lubricants, preservatives, anti-oxidative agents, isotonic agents, buffering agents, coating agents, sweetening agents, dissolving agents, bases, dispersing agents, stabilizing agents, coloring agents and the like.

Illustrative examples of these pharmaceutically acceptable carriers are listed in the following.

Firstly, as excipients, the following can be listed: starch and derivatives of starch (such as dextrin, carboxymethyl starch and the like), cellulose and derivatives of cellulose (such as methylcellulose, hydroxypropylmethylcellulose and the like), sugars (such as lactose, sucrose, glucose and the like), silicic acid and silicates (such as naturally occurring aluminum silicate, magnesium silicate and the like), carbonates (such as calcium carbonate, magnesium carbonate, sodium hydrogencarbonate and the like), aluminum magnesium hydroxide, synthetic hydrotalcite, polyoxyethylene derivatives, glycerin monostearate, sorbitan monooleic acid and the like.

As bonding agents, the following can be listed: starch and starch derivatives (such as alpha starches, dextrin and the like), cellulose and derivatives of cellulose (such as ethyl cellulose, sodium carboxymethyl cellulose, hydroxypropylmethyl cellulose and the like), gum arabic, traganth, gelatin, sugars (such as glucose, sucrose and the like), ethanol, polyvinyl alcohols and the like.

As disintegrators, the following can be listed: starch and starch derivatives (such as carboxymethyl starch, hydroxypropyl starch and the like), cellulose and cellulose derivatives (such as sodium carboxymethyl cellulose, crystal cellulose, hydroxypropylmethyl cellulose and the like), carbonates (such as calcium carbonate, calcium hydrogencarbonate and the like), traganth, gelatins, agar and the like.

As lubricants, the following can be listed: stearic acid, calcium stearate, magnesium stearate, talc, silicic acid and its salts (such as light silicic anhydrides, naturally occurring aluminum silicates and the like), titanium oxide, calcium hydrogen phosphate, dry aluminum hydroxide gel, macrogol and the like.

As preservatives, the following can be listed: p-hydroxybenzoates, sulfites (such as sodium sulfites, sodium pyrosulfites and the like), phosphates (such as sodium phosphates, calcium polyphosphates, sodium polyphosphates, sodium methaphosphate and the like), alcohols (such as chlorobutanol, benzyl alcohol and the like), benzalkonium chloride, benzethonium chloride, phenol, cresol, chlorocresol, dihydroacetic acid, sodium dihydroacetate, glycerin sorbic acid, sugars and the like.

As anti-oxidative agents, the following can be listed: sulfites (such assodium sulfite, sodium hydrogen sulfite and the like), rongalite, erythorbic acid, L-ascorbic acid, cysteine, thioglycerol, butylhydroxyanisol, dibutylhydroxytoluene, propylgallic acid, ascorbyl palmitate, dl-a-tocopherol and the like.

As isotonic agents, the following can be listed: sodium chloride, sodium nitrate, potassium nitrate, dextrin, glycerin, glucose and the like.

As buffering agents, the following can be listed: sodium carbonate, hydrochloric acid, boric acid, phosphates (such as sodium hydrogenphosphate) and the like.

As coating agents, the following can be listed: cellulose derivatives (such as hydroxypropyl cellulose, cellulose acetate phthalate, hydroxypropylmethyl cellulose phthalate and the like), shellac, polyvinylpyrrolidone, polyvinylpyridines (such as poly-2-vinylpyridine, poly-2-vinyl-5-ethylpyridine and the like), polyvinylacetyl diethylaminoacetate, polyvinyl alcohol phthalate, methacrylate, methacrylate copolymers and the like.

As sweetening agents, the following can be listed: sugars (such as glucose, sucrose, lactose and the like), sodium saccharin, sugar alcohols and the like.

As dissolving agents, the following can be listed: ethylenediamine, nicotinamide, sodium saccharin, citric acid, citrates, sodium benzoic acid, soaps, polyvinylpyrrolidone, polysolvates, sorbitan fatty acid esters, glycerin, propylene glycol, benzyl alcohols and the like.

As bases, the following can be listed: fats (such as lard and the like), vegetable oils (such as olive oil, sesame oil and the like), animal oil, lanolin acid, petrolatums, paraffin, wax, resins, bentonite, glycerin, glycol oils, higher alcohols (such as stearyl alcohol, cetanol) and the like.

As dispersing agents, the following can be listed: gum arabic, traganth, cellulose derivatives (such as methyl cellulose and the like), stearic acid polyesters, sorbitan sesquioleate, aluminum monostearate, sodium alginate, polysolvates, sorbitan fatty acid esters and the like.

Lastly, as stabilizing agents, the following can be listed: sulfites (such as sodium hydrogen sulfite and the like), nitrogen, carbon dioxide and the like.

Though the content of the compound of the present invention in these pharmaceutical preparations varies depending on the dosage forms, it may be contained preferably in a concentration of from 0.01 to 100% by weight.

Dose of the antiallergic agent of the present invention can be varied over a broad range depending on each warm-blooded animal including human and the like, to be treated, extent of each disease, doctor's judgement and the like. In general, however, it may be administered in a dose of from 0.01 to 50 mg, preferably from 0.01 to 10 mg, as the active ingredient per day per kg body weight in the case of oral administration or in a dose of from 0.01 to 10 mg, preferably from 0.01 to 5 mg, as the active ingredient per day per kg body weight in the case of parenteral administration. The daily dose described above may be used in one portion or in divided portions and changed optionally in accordance with the extent of diseases and doctor's judgement.

The following examples are intended to illustrate this invention, however these examples are intended to illustrate the invention and not to be construed to limit the scope of the invention.

EXAMPLE 1

Ethyl 2-[(octyloxyacetyl)amino]-4-nitrobenzoate (compound 1)

To a mixture of 20.00 g of ethyl 4-nitroanthranilate (95.15 mmol) in 60 ml of toluene was added 19.71 g of octyloxy-acetic acid (104.67 mmol) and 0.91 g of p-toluenesulfonic acid monohydrate (4.76 mmol), and the mixture was stirred at 120° C. for 6 hours. (The water formed during the reaction process were removed as required.) After the mixture was cooled at 30° C., 0.53 g of triethylamine (5.71 mmol) was added and the mixture was concentrated under reduced pressure. The resulting crude product was crystallized from methanol to give 41.64 g of title compound (1). (yield=93.9%).

$^1$H-NMR (CDCl$_3$, δ-TMS); 11.86 (s, 1H), 9.68 (s, 1H), 8.21 (d, 1H, J=8.8 Hz), 7.91 (d, 1H, J=8.8 Hz), 4.22 (m, 2H), 4.13 (s, 2H), 3.63 (t, 2H, J=6.4 Hz), 1.80~1.20 (m, 15H), 0.88 (t, 3H, J=6.8 Hz); IR (KBr, cm$^{-1}$): 3240, 2850, 1740, 1550, 1345; Elemental analysis for: C$_{19}$H$_{28}$N$_2$O$_6$; Calculated (%): C 59.98; H 7.42; N 7.36; O 25.23; Found (%): C 59.75; H 7.57; N 7.26; O 25.42.

EXAMPLE 2

Ethyl 2-[(octyloxyacetyl)amino]-4-nitrobenzoate (compound 1)

To a mixture of 20.00 g of ethyl 4-nitroanthranilate (95.15 mmol) in 60 ml of tetrahydrofuran was added 21.63 g of octyloxyacetylchloride (104.67 mmol) and 11.65 g of triethylamine (115.14 mmol) at 10° C., and the mixture was stirred at 10° C. for 1 hour. The reaction mixture was filtered and the filtrate was concentrated under reduced pressure. The resulting crude product was crystallized from methanol to give 41.91 g of title compound (1). (yield=94.5%).

EXAMPLE 3

Ethyl 2-[(octyloxyacetyl)amino]-4-aminobenzoate (compound 2)

To a mixture of 10.00 g of ethyl 2-[(octyloxyacetyl) amino]-4-nitorbenzoate (26.28 mmol) in 58 ml of 2-methoxyethanol and 16 ml of toluene was added 6.88 g of zinc powder at 20° C. After the mixture was stirred at 10° C., 0.53 g of triethylamine (5.71 mmol) was added keeping the temperature below 45° C. for 1 hour. Further, the mixture was stirred at 80° C. for 3 hours. The reaction mixture was filtered and the filtrate was added toluene and water, and extracted with toluene. The organic layer was concentrated under reduced pressure. The resulting crude product was crystallized from heptane to give 9.07 g of title compound (2). (yield=98.4%)

$^1$H-NMR (CDCl$_3$, δ-TMS); 11.96 (S, 1H), 8.13 (s. 1H), 7.88 (d, 1H, J=8.8 Hz), 6.32 (d, 1H, J=8.8 Hz), 4.35 (t, 2H, J=5.2 Hz), 4.22 (bs, 2H), 4.07 (s, 2H), 3.74 (t, 2H, J=5.2 Hz), 1.80~1.20 (m, 15H), 0.88 (t, 3H, J=6.8 Hz); IR (KBr, cm$^{-1}$): 3350, 2850, 1725; Elemental analysis for: C$_{19}$H$_{30}$N$_2$O$_4$; Calculated (%): C 65.11; H 8.63; N 7.99; O 18.26; Found (%): C 65.23; H 8.57; N 7.86; O 18.34.

EXAMPLE 4

Ethyl 2-[N-methyl-N-(octyloxyacetyl)amino]-4-aminobenzoate (compound 3)

To a mixture of 10.00 g of ethyl 2-[(octyloxyacetyl) amino]-4-aminobenzoate (28.53 mmol) in 50 ml of N,N-dimethylformamide was cooled at 0 to 5° C. After the mixture was added 0.99 g of sodium ethoxide (14.27 mmol), 2.20 g of dimethyl sulfate (17.12 mmol) was added s at −10 to −5° C. After the mixture was stirred at −10 to −5° C. for 1 hour, 0.99 g of sodium ethoxide (14.27 mmol) and 2.20 g of dimethyl sulfate (17.12 mmol) was added s at −10 to −5° C. After the mixture was stirred at −10 to −5° C. for 1 hour, 0.40 g of sodium ethoxide (5.71 mmol) and 0.88 g of dimethyl sulfate (6.85 mmol) was added s at −10 to −5° C. After the mixture was stirred at −10 to −5° C. for 1 hour, 0.40 g of sodium ethoxide (5.71 mmol) and 0.88 g of dimethyl sulfate (6.85 mmol) was added s at −10 to −5° C. After the mixture was stirred at −10 to −5° C. for 1 hour, 5.00 g of sulfuric acid (1% solution in water), 50 ml of water and 50 ml of toluene were added, and extracted with toluene. The organic layer was concentrated under reduced pressure. The resulting crude product was crystallized from toluene to give 8.54 g of title compound (3). (yield=80.0%)

$^1$H-NMR (CDCl$_3$, δ-TMS); 7.94 (d, 1H, J=8.0 Hz), 6.65 (d, 1H, J=8.0 Hz), 6.32 (d, 1H, J=1.6 Hz), 4.40 (s, 2H) 4.22 (m, 2H), 3.85 (m, 2H), 3.40 (m, 2H), 3.18 (s, 3H), 1.80~1.20 (m, 15H), 0.87 (t, 3H, J=6.8 Hz); IR (KBr, cm$^{-1}$): 3350, 2850, 1725; Elemental analysis for: C$_{20}$H$_{32}$N$_2$O$_4$; Calculated (%): C 65.90; H 8.85; N 7.69; O 17.56; Found (%): C 65.73; H 8.77; N 7.83; O 17.67.

EXAMPLE 5

Ethyl 2-[-methyl-N-(octyloxyacetyl)amino]-4-(3,5-dimethoxy-4-hydroxycinnamoyl)aminobenzoate (compound 4)

To the mixture of 8.20 g of 3,5-dimethoxy-4-hydroxycinnamic acid (36.2 mmol) in 30 ml of tetrahydrofuran and 0.265 g of N,N-dimethylformamide was cooled at 0° C. The mixture was added 4.31 g of tionyl chloride (36.2 mmol) at 0 to 10° C. After the mixture was stirred at 0 to 10° C. for 1 hour, a solution of 12.00 g of ethyl 2-[N-methyl-N-(octyloxyacetyl)amino]-4-aminobenzoate (32.9 mmol) in 36 ml of tetrahydrofuran was added. After the mixture was stirred at 0 to 10° C. for 30 minutes, 7.80 g of pyridine (82.2 mmol) was added. After the mixture was stirred at 0 to 10° C. for 30 minutes, 60 ml of toluene and 60 ml of water were added, and extracted with toluene. The organic layer was concentrated under reduced pressure to give a crude product. Purification of this crude product by column chromatography on silica gel (hexane/ethyl acetate=1/2 as an eluent) gave 17.66 g of title compound (4). (yield=94.0%)

$^1$H-NMR (d$_6$-DMSO, δ-TMS); 10.52 (s, 1H), 8.94 (s, 1H), 7.96 (d, 1H, J=8.8 Hz), 7.83 (d, 1H, J=2.0 Hz), 7.76 (d, 1H, J=8.8 Hz), 7.57 (d, 1H, J=15.6 Hz), 6.93 (s, 2H), 6.68 (d, 1H, J=15.6 Hz), 4.24 (q, 2H), 3.85 (s, 6H), 3.78 (s, 3H), 3.68 (m, 2H), 3.38 (s, 3H), 3.27 (m, 2H), 1.40~1.10 (m, 12H), 0.83 (m, 3H); IR (KBr, cm$^{-1}$): 3350, 1745, 1680, 1225; Elemental analysis for: C$_{31}$H$_{42}$N$_2$O$_8$; Calculated (%): C 65.24; H 7.42; N 4.91; O 22.42; Found (%): C 65.35; H 7.35; N 4.96; O 22.34.

EXAMPLE 6

Ethyl 2-[N-methyl-N-(octyloxyacetyl)amino]-4-acetylaminobenzoate (compound 5)

To the solution of 5.0 g of ethyl 2-[N-methyl-N-(octyloxyacetyl)amino]-4-aminobenzoate (13.72 mmol) in 15 ml of ethyl acetate was added 3.0 g of acetic anhydride at room temperature for 2 hours. The reaction mixture was filtered and the filtrate was concentrated under reduced pressure. The resulting crude product was crystallized from ethyl acetate and hexane to give 4.73 g of title compound (5). (yield=85.0%).

$^1$H-NMR (d$_6$-DMSO, δ-TMS); 10.52 (s, 1H), 7.94 (d, 1H, J=8.0 Hz), 6.65 (d, 1H, J=8.0 Hz), 6.32 (d, 1H, J=1.6 Hz), 4.24 (q, 2H), 3.78 (s, 3H), 3.68 (m, 2H), 3.38 (s, 3H), 3.27 (m, 2H), 2.34 (s3H), 1.40~1.10 (m, 12H), 0.83 (m, 3H); IR (KBr, cm$^{-1}$): 3350, 1745, 1680, 1225; Elemental analysis for: C$_{22}$H$_{34}$N$_2$O$_5$; Calculated (%): C 65.00; H 8.43; N 6.89; O 19.68; Found (%): C 65.12; H 8.35; N 6.96; O 19.57.

EXAMPLE 7

Ethyl 2-[N-methyl-N-(methoxyacetyl)amino]-4-nitrobenzoate (compound 6)

In accordance with EXAMPLE 4, ethyl 2-[(methoxyacetyl)amino]-4-nitrobenzoate was used instead of Ethyl 2-[(octyloxyacetyl)amino]-4-aminobenzoate, the title compound (6) was obtained.

$^1$H-NMR (CDCl$_3$, δ-TMS); 9.68 (s, 1H), 8.21 (d, 1H, J=8.8 Hz), 7.91 (d, 1H, J=8.8 Hz), 4.23 (t, 2H, J=7.2 Hz), 4.13 (s, 2H), 3.78 (s, 3H), 3.56 (s, 3H), 1.15 (t, 3H, J=6.8 Hz); IR (KBr, cm$^{-1}$): 2850, 1740, 1550, 1345, 1225; Elemental analysis for: C$_{13}$H$_{16}$N$_2$O$_6$; Calculated (%): C 52.70; H 5.44; N 9.46; O 32.40; Found (%): C 52.55; H 5.35; N 9.44; O 32.66.

EXAMPLE 8

Ethyl 2-[N-methyl-N-(decylxyacetyl)amino]-4-nitrobenzoate (compound 7)

In accordance with EXAMPLE 4, ethyl 2-[(decyloxyacetyl)amino]-4-nitrobenzoate as used instead of Ethyl 2-[(octyloxyacetyl)amino]-4-aminobenzoate, the title compound (7) was obtained.

$^1$H-NMR (CDCl$_3$, δ-TMS); 9.68 (s, 1H), 8.21 (d, 1H, J=8.8 Hz), 7.91 (d, 1H, J=8.8 Hz), 4.22 (m, 2H), 4.13 (m, 2H), 3.63 (t, 2H, J=6.4 Hz), 3.56 (s, 3H), 1.80~1.20(m, 19H), 0.88 (t, 3H, J=6.8 Hz); IR (KBr, cm$^{-1}$): 2850, 1740, 1550, 1345, 1225; Elemental analysis for: C$_{22}$H$_{34}$N$_2$O$_6$; Calculated (%): C 62.54; H 8.11; N 6.63; O 22.72; Found (%): C 62.55; H 8.05; N 6.43; O 22.97.

EXAMPLE 9

Ethyl 2-[N-methyl-N-(methoxyacetyl)amino]-4-benzylaminobenzoate (compound 8)

In accordance with EXAMPLE 4, ethyl 2-[(methoxyacetyl)amino]-4-benzylaminobenzoate was used instead of Ethyl 2-[(octyloxyacetyl)amino]-4-aminobenzoate, the title compound (8) was obtained.

$^1$H-NMR (CDCl$_3$, δ-TMS); 8.13 (s, 1H), 7.88 (d, 1H, J=8.8 Hz), 7.22 (m, 5H), 6.32 (d, 1H, J=8.8 Hz), 5.23 (s, 1H), 5.15 (s, 2H), 4.25 (t, 2H, J=5.2 Hz), 4.07 (s, 2H), 3.74 (s, 3H), 3.58 (s, 3H), 1.22 (t, 3H, J=6.8 Hz); IR (KBr, cm$^{-1}$): 3350, 2850, 1725, 1225; Elemental analysis for: C$_{20}$H$_{24}$N$_2$O$_4$; Calculated (%): C 67.39; H 6.79; N 7.86; O 17.96; Found (%): C 67.55; H 6.84; N 7.83; O 17.78.

EXAMPLE 10

Ethyl 2-[N-decyl-N-(butoxyacetyl)amino]-4-nitrobenzoate (compound 9)

In accordance with EXAMPLE 1, ethyl 4-nitro-N-decyl-anthranilate and butoxy acetic acid were used instead of ethyl 4-nitroanthranilate and octyloxyacetic acid, the title compound (9) was obtained.

$^1$H-NMR (CDCl$_3$, δ-TMS); 9.68 (s, 1H), 8.21 (d, 1H, J=8.8 Hz), 7.91 (d, 1H, J=8.8 Hz), 4.22 (m, 4H), 4.13 (s, 2H), 3.63 (m, 2H), 2.25~1.20 (m, 20H), 1.23 (t, 3H, J=7.0 Hz), 0.88 (m, 6H); IR (KBr, cm$^{-1}$): 2850, 1740, 1550, 1345; Elemental analysis for: C$_{25}$H$_{40}$N$_2$O$_6$; Calculated (%): C 64.63; H 8.63; N 6.03; O 20.66; Found (%): C 64.55; H 8.84; N 6.00; O 20.61.

EXAMPLE 11

Ethyl 2-[N-methyl-N-(methoxyacetyl)amino]-4-decylaminobenzoate (compound 10)

In accordance with EXAMPLE 1, ethyl 4-nitro-N-methyl-anthranilate and methoxyacetic acid were used instead of ethyl 4-nitroanthranilate and octyloxyacetic acid, the title compound (10) was obtained.

$^1$H-NMR (CDCl$_3$, δ-TMS); 8.13 (s, 1H), 7.88 (d, 1H, J=8.8 Hz), 6.32 (d, 1H, J=8.8 Hz), 5.23 (s, 1H), 4.25 (t, 2H, J=5.2 Hz), 4.07 (s, 2H), 3.74 (s, 3H), 3.58 (s, 3H), 2.25~1.26 (m, 21H), 0.90 (t, 3H, J=6.8 Hz); IR (KBr, cm$^{-1}$): 3350, 2850, 1725, 1225; Elemental analysis for: C$_{23}$H$_{38}$N$_2$O$_4$; Calculated (%): C 67.94; H 9.42; N 6.89; O 15.74; Found (%): C 67.99; H 9.34; N 6.78; O 15.89.

EXAMPLE 12

Ethyl 2-[N-(2-propenyl)-N-(methoxyacetyl)amino]-4-nitrobenzoate (compound 11)

In accordance with EXAMPLE 1, ethyl 4-nitro-N-(2-propenyl)-anthranilate and methoxyacetic acid were used instead of ethyl 4-nitroanthranilate and octyloxyacetic acid, the title compound (11) was obtained.

$^1$H-NMR (CDCl$_3$, δ-TMS); 9.68 (s, 1H), 8.21 (d, 1H, J=8.8 Hz), 7.91 (d, 1H, J=8.8 Hz), 5.95 (m, 1H), 5.20~5.02 (m, 2H), 4.23(t, 2H, J=7.2 Hz), 4.13 (s, 2H), 3.78 (s, 3H), 3.45 (d, 2H, J=7.2 Hz), 1.15 (t, 3H, J=6.8 Hz); IR (KBr, cm$^{-1}$): 2850, 1740, 1550, 1345; Elemental analysis for: C$_{15}$H$_{18}$N$_2$O$_6$; Calculated (%): C 57.48; H 5.43; N 8.38; O 28.72; Found (%): C 57.55; H 5.45; N 8.22; O 28.78.

EXAMPLE 13

Ethyl 2-[N-geranyl-N-(ethoxyacetyl)amino]-4-aminobenzoate (compound 12)

In accordance with EXAMPLE 3, ethyl 2-[N-geranyl-N-(ethoxyacetyl)amino]-4-nitrobenzoate was used instead of Ethyl 2-(octyloxyacetyl)amino-4-nitrobenzoate, the title compound (12) was obtained.

$^1$H-NMR (CDCl$_3$, δ-TMS); 8.13 (s, 1H), 7.88 (d, 1H, J=8.8 Hz), 6.32 (d, 1H, J=8.8 Hz), 5.40 (m, 1H), 5.10 (m, 1H), 4.35 (t, 2H, J=5.2 Hz), 4.22 (bs, 2H), 4.07 (s, 2H), 3.74 (t, 2H, J=5.2 Hz), 3.45 (m, 2H), 2.25~1.55 (m, 131H), 1.18 (m, 6H); IR (KBr, cm$^{-1}$): 3350, 2850, 1725, 1225; Elemental analysis for: C$_{23}$H$_{34}$N$_2$O$_4$; Calculated (%): C 68.63; H 8.51; N 6.96; O 15.90; Found (%): C 68.55; H 8.57; N 6.86; O 16.02.

EXAMPLE 14

Ethyl 2-[N-methyl-N-(geranyloxyacetyl)amino]-4-acetylaminobenzoate (compound 13)

In accordance with EXAMPLE 1, ethyl 4-acetylamino-N-methyl-anthranilate and geranyloxyacetic acid were used instead of ethyl 4-nitroanthranilate and octyloxyacetic acid, the title compound (13) was obtained.

$^1$H-NMR (CDCl$_3$, δ-TMS); 10.89 (s, 1H), 8.13 (S, 1H), 7.88 (d, 1H, J=8.8 Hz), 6.32 (d, 1H, J=8.8 Hz), 5.40 (m, 1H), 5.10 (m, 1H), 4.13 (t, 2H, J=5.2 Hz), 4.07 (s, 2H), 3.74 (t, 2H, J=5.2 Hz), 3.55 (s, 31H), 2.25 1.55 (m, 131H), 2.23 (s, 31H), 1.18 (m, 31H); IR (KBr, cm$^{-1}$): 3350, 2850, 1725, 1225; Elemental analysis for: C$_{24}$H$_{34}$N$_2$O$_5$; Calculated (%): C 66.95; H 7.96; N 6.51; O 18.58; Found (%): C 66.89; H 7.97; N 6.45; O 18.69.

EXAMPLE 15

Ethyl 2-[N-methyl-N-(octyloxyacetyl)amino]-4-(N,N-dimethyl)aminobenzoate (compound 14)

In accordance with EXAMPLE 1, ethyl 4-(N,N-dimethyl)amino-N-methyl-anthranilate was used instead of ethyl 4-nitroanthranilate, the title compound (14) was obtained.

$^1$H-NMR (CDCl$_3$, δ-TMS); 7.94 (d, 1H, J=8.0 Hz), 6.65 (d, 1H, J=8.0 Hz), 6.32 (d, 1H, J=1.6 Hz), 4.27 (m, 2H), 4.06 (s, 2H), 3.78 (m, 2H), 3.18 (s, 3H), 2.56 (s, 6H), 1.80~1.20 (m, 15H), 0.87 (t, 3H, J=6.8 Hz); IR (KBr, cm$^{-1}$): 2850, 1725, 1225; Elemental analysis for: C$_{22}$H$_{36}$N$_2$O$_4$; Calculated (%): C 67.31; H 9.24; N 7.14; O 16.30; Found (%): C 67.34; H 9.14; N 7.13; O 16.39.

EXAMPLE 16

Ethyl 2-[N-methyl-N-(methoxyacetyl)amino]-4-vinylaminobenzoate (compound 15)

In accordance with EXAMPLE 1, ethyl 4-vinylamino-N-methyl-anthranilate and methoxyacetic acid were used instead of ethyl 4-nitroanthranilate and octyloxyacetic acid, the title compound (15) was obtained.

$^1$H-NMR (CDCl$_3$, δ-TMS); 7.88 (d, 1H, J=8.0 Hz), 6.65 (d, 1H, J=8.0 Hz), 6.32 (d, 1H, J=1.6 Hz), 6.23 (m, 1H), 5.26 (s, 1H), 4.90 (m, 1H), 4.56 (m, 1H), 4.25 (t, 2H, J=5.2 Hz), 4.07 (s, 2H), 3.74 (s, 3H), 3.58 (s, 3H), 1.22 (t, 3H, J=6.8 Hz); IR (KBr, cm$^{-1}$): 2850, 1725, 1225; Elemental analysis for: C$_{15}$H$_{20}$N$_2$O$_4$; Calculated (%): C 61.63; H 6.90; N 9.58; O 21.89; Found (%): C 61.55; H 6.84; N 9.43; O 22.18.

EXAMPLE 17

Ethyl 2-[N-methyl-N-(methoxyacetyl)amino]-4-geranylaminobenzoate (compound 16)

In accordance with EXAMPLE 1, ethyl 4-geranylamino-N-methylanthranilate and methoxyacetic acid were used instead of ethyl 4-nitroanthranilate and octyloxyacetic acid, the title compound (16) was obtained.

$^1$H-NMR (CDCl$_3$, δ-TMS); 7.88 (d, 1H, J=8.0 Hz), 6.65 (d, 1H, J=8.0 Hz), 6.32 (d, 1H, J=1.6 Hz), 6.23 (m, 1H), 5.45 (m, 1H), 5.26 (s, 1H), 5.08 (m, 1H), 4.25 (t, 2H, J=5.2 Hz), 4.10 (d, 2H, J=7.5 Hz), 4.07 (s, 2H), 3.58 (s, 3H), 2.25~1.55 (m, 13H), 1.22 (t, 3H, J=6.8 Hz); IR (KBr, cm$^{-1}$): 2850, 1725, 1225; Elemental analysis for: C$_{23}$H$_{34}$N$_2$O$_4$; Calculated (%): C 68.63; H 8.51; N 6.96; O 15.90; Found (%): C 68.55; H 8.64; N 6.93; O 15.88.

EXAMPLE 18

Ethyl 2-[N-methyl-N-(octyloxyacetyl)amino]-4-[(3,4,5-trimethoxycinnamoyl)amino]-benzoate (compound 17)

In accordance with EXAMPLE 5, 3, 4, 5-trimethoxycinnamic acid was used instead of 3,5-dimethoxy-4-hydroxycinnamic acid, the title compound (17) was obtained.

$^1$H-NMR (d$_6$-DMSO, δ-TMS); 10.52 (s, 1H), 7.96 (d, 1H, J=8.8 Hz), 7.83 (d, 1H, J=2.0 Hz), 7.76 (d, 1H, J=8.8 Hz), 7.57 (d, 1H, 15.6 Hz), 6.93 (s, 2H), 6.68 (d, 1H, J=15.6 Hz), 4.24 (q, 2H), 3.78 (s, 9H), 3.78 (s, 3H), 3.68 (m, 2H), 3.38 (s, 3H), 3.27 (m, 2H), 1.40~1.10 (m, 12H), 0.83 (m, 3H); IR (KBr, cm$^{-1}$): 3350, 1745, 1680, 1225; Elemental analysis for: C$_{33}$H$_{44}$N$_2$O$_8$; Calculated (%): C 65.73; H 7.59; N 4.79; O 21.89; Found (%): C 65.67; H 7.55; N 4.86; O 21.92.

EXAMPLE 19

7-[(3,5-dimethoxy-4-hydroxy-cinnamoyl)amino]-3-octyloxy-4-hydroxy-1-methyl-2(1H)- quinolinone (compound 18)

To a solution 16.25 g of potassium tert-butoxide (114.9 mmol) in 97 ml of tetrahydrofuran was stirred at room temperature. After the solution was cooled at 0° C., a solution of 18.77 g of ethyl 2-[N-methyl-N-(octyloxyacetyl)amino]-4-[(3,5-dimethoxy-4-hydroxycinnamoyl)amino]-benzoate (32.9 mmol) in 56 ml of tetrahydrofuran was added at 0 to 10° C. After the mixture was stirred at 0 to 10° C. for 30 minutes, 85 g of 2 mol/l of aqueous hydrogen chloride solution was added, and extracted with 38 ml of ethyl acetate. The organic layer was washed with 60 g of 1%-NaCl solution in water, and concentrated under reduced pressure to give a crude product. The resulting crude product was crystallized from 2-propanol to give 15.87 g of title compound (18). (yield=92.0%).

$^1$H-NMR (d$_6$-DMSO, δ-TMS); 10.39 (s, 1H), 10.29 (s, 1H), 8.92 (s, 1H), 7.99 (s, 1H), 7.85 (d, 1H, J=8.8 Hz), 7.53 (d, 1H, J=15.6 Hz), 7.49 (s, 1H), 6.93 (s, 2H), 6.75 (d, 1H, J=15.6 Hz), 3.92 (t, 2H, J=6.8 Hz), 3.82 (s, 6H), 3.54 (s, 3H), 1.68 (m, 2H), 1.25 (m, 10H), 0.86 (t, 3H,J=6.8 Hz); IR (KBr, cm$^{-1}$): 3550, 2940, 1600, 1515, 1250; Elemental analysis for: C$_{29}$H$_{36}$N$_2$O$_7$; Calculated (%): C 66.39; H 6.92; N 5.34; O 21.35; Found (%): C 66.45; H 7.08; N 4.96; O 21.51.

EXAMPLE 20

7-[(3,5-dimethoxy-4-hydroxy-cinnamoyl)amino]-3-octyloxy-4-hydroxy-1-methyl-2(1H)-quinolinone (compound 18)

To a mixture of 5.80 g of sodium hydride (purity 60%, 114.9 mmol) in 90 ml of tetrahydrofuran was added a solution of 18.77 g of ethyl 2-[N-methyl-N-(octyloxyacetyl)amino]-4-[(3,5-dimethoxy-4-hydroxycinnamoyl)amino]-benzoate (32.9 mmol) in 56 ml of tetrahydrofuran at 0 to 10° C. After the mixture was stirred at 0 to 10° C. for 30 minutes, 85 g of 2 mol/l of aqueous hydrogen chloride solution was added, and extracted with 38 ml of ethyl acetate. The organic layer was washed with 60 g of 1%-NaCl solution in water, and concentrated under reduced pressure to give a crude product. The resulting crude product was crystallized from 2-propanol to give 15.70 g of title compound (18). (yield=92.0%).

EXAMPLE 21

7-[(3,5-dimethoxy-4-hydroxy-cinnamoyl)amino]-3-octyloxy-4-hydroxy-1-methyl-2(1H)-quinolinone (compound 18)

To a solution of 144.9 mmol of LHDS* in 150 ml of tetrahydrofuran was added a solution of 18.77 g of ethyl 2-[N-methyl-N-(octyloxyacetyl)amino]-4-[(3,5-dimethoxy- 4-hydroxycinnamoyl)amino]-benzoate (32.9 mmol) in 56 ml of tetrahydrofuran at −40° C. After the mixture was stirred at −40° C. for 30 minutes, 85 g of 2 mol/l of aqueous hydrogen chloride solution was added, and extracted with 38 ml of ethyl acetate. The organic layer was washed with 60 g of 1%-NaCl solution in water, and concentrated under reduced pressure to give a crude product. The resulting crude product was crystallized from 2-propanol to give 16.05 g of title compound (18). (yield=93.0%). *LHDS: Lithium hexam ethyl disilazed

EXAMPLE 22

7-[(3,5-dimethoxy-4-hydroxy-cinnamoyl)amino]-3-octyloxy-4-hydroxy-1-methyl-2(1H)-quinolinone (compound 18)

To a solution of 144.9 mmol of LDA* in 150 ml of tetrahydrofuran was added a solution of 18.77 g of ethyl 2-[N-methyl-N-(octyloxyacetyl)amino]-4-[(3,5-dimethoxy-4-hydroxycinnamoyl)amino]-benzoate (32.9 mmol) in 56 ml of tetrahydrofuran at −40° C. After the mixture was stirred at −40° C. for 30 minutes, 85 g of 2 mol/l of aqueous hydrogen chloride solution was added, and extracted with 38 ml of ethyl acetate. The organic layer was washed with 60 g of 1%-NaCl solution in water, and concentrated under reduced pressure to give a crude product. The resulting crude product was crystallized from 2-propanol to give 15.18 g of title compound (18). (yield 88.0%). *LDA: Lithium diisopropylamido

EXAMPLE 23

7-acetylamino-3-octyloxy-4-hydroxy-1-methyl-2 (1H)-quinolinone (compound 19)

In accordance with EXAMPLE 19, ethyl 2-[N-methyl-N-(octyloxyacetyl)amino]-4-acetylaminobenzoate was used instead of ethyl 2-[N-methyl-N-(octyloxyacetyl)amino]-4-[(3,5-dimethoxy-4-hydroxycinnamoyl)amino]-benzoate, the title compound (19) was obtained.

$^1$H-NMR (d$_6$-DMSO, δ-TMS); 10.28 (s, 1H), 10.23 (s, 1H), 7.85 (s, 1H), 7.80 (d, 1H, J=8.8 Hz), 7.42 (d, 1H, J=8.8 Hz), 3.94 (t, 2H, J=6.8 Hz), 3.52 (s, 3H), 2.10 (s, 3H), 1.69 (m, 2H), 1.25 (m, 10H), 0.86 (t, 3H, J=6.8 Hz); IR (KBr, cm$^{-1}$): 3550, 2940, 1610, 1515, 1250; Elemental analysis for: C$_{20}$H$_{28}$N$_2$O$_4$; Calculated (%): C 66.64; H 7.83; N 7.77; O 17.76; Found (%): C 66.55; H 7.78; N 7.86; O 17.81.

EXAMPLE 24

7-benzoylamino-3-octyloxy-4-hydroxy-1-methyl-2 (1H)-quinolinone (compound 20)

In accordance with EXAMPLE 19, ethyl 2-[N-methyl-N-(octyloxyacetyl)amino]-4-benzoylaminobenzoate was used instead of ethyl 2-[N-methyl-N-(octyloxyacetyl)amino]-4-[(3,5-dimethoxy-4-hydroxycinnamoyl)amino]-benzoate, the title compound (20) was obtained.

$^1$H-NMR (d$_6$-DMSO, δ-TMS); 10.28 (s, 1H), 10.23 (s, 1H), 8.10 (m, 2H), 7.85 (s, 1H), 7.80 (d, 1H, J=8.8 Hz), 7.60~7.45 (m, 3H), 7.42 (d, 1H, J=8.8 Hz), 3.94 (t, 2H, J=6.8 Hz), 3.52 (s, 3H), 1.69 (m, 2H), 1.25 (m,10H), 0.86 (t, 3H, J=6.8 Hz); IR (KBr, cm$^{-1}$):3550,2940, 1610, 1515, 1250; Elemental analysis for: C$_{25}$H$_{30}$N$_2$O$_4$; Calculated (%): C 71.06; H 7.16; N 6.63; O 15.15; Found (%):C 71.00; H 7.28; N 6.56; O 15.16.

EXAMPLE 25

7-nitro-3-methoxy-4-hydroxy-1-ethyl-2(1H)-quinolinone (compound 21)

In accordance with EXAMPLE 20, ethyl 2-[N-ethyl-N-(methoxyacetyl)amino]-4-nitrobenzoate was used instead of ethyl 2-[N-methyl-N-(octyloxyacetyl)aminoi-4-[(3,5-dimethoxy-4-hydroxycinnamoyl)amino]-benzoate, the title compound (21) was obtained.

$^1$H-NMR (d$_6$-DMSO, δ-TMS); 11.05 (s, 1H), 8.05 (m, 3H), 3.75 (s, 3H), 3.68 (d, 2H, J=6.8 Hz), 1.23 (t, 3H, J=6.8 Hz); IR(KBr, cm$^{-1}$): 3550,2940, 1610, 1515, 1250, 1100; Elemental analysis for: C$_{12}$H$_{12}$N$_2$O$_5$; Calculated (%): C 54.54; H 4.58; N 10.60; O 30.28; Found (%): C 54.44; H 4.65; N 10.56; O 30.35.

EXAMPLE 26

6-nitro-3-methoxy-4-hydroxy-1-octyl-2(1H)-quinolinone (compound 22)

In accordance with EXAMPLE 21, ethyl 2-[N-octyl-N-(methoxyacetyl)amino]-5-nitrobenzoate was used instead of ethyl 2-[N-methyl-N-(octyloxyacetyl)amino]-4-[(3,5-dimethoxy-4-hydroxycinnamoyl)amino]-benzoate, the title compound (22) was obtained.

$^1$H-NMR (d$_6$-DMSO, δ-TMS); 11.05 (s, 1H), 8.05 (m, 3H), 3.75 (s, 3H), 3.68 (d, 2H, J=6.8 Hz), 1.87~1.23 (m, 12H), 0.90 (t, 3H, J=6.9 Hz); IR (KBr, cm$^{-1}$): 3500, 2940, 1610, 1515, 1250, 1100; Elemental analysis for: C$_{18}$H$_{24}$N$_2$O$_5$; Calculated (%): C 62.05; H 6.94; N 8.04; O 22.96; Found (%): C 62.00; H 7.08; N 8.02; O 22.90.

EXAMPLE 27

5-amino-3-ethoxy-4-hydroxy-1-methyl-2(1H)-quinolinone (compound 23)

In accordance with EXAMPLE 22, ethyl 2-[N-methyl-N-(ethoxyacetyl)amino]-6-aminobenzoate was used instead of ethyl 2-[N-methyl-N-(octyloxyacetyl)amino]-4-[(3,5-dimethoxy-4-hydroxycinnamoyl)amino]-benzoate, the title compound (23) was obtained.

$^1$H-NMR (d$_6$-DMSO, δ-TMS); 10.85 (s, 1H), 7.88~7.50 (m, 3H), 5.90 (bs, 2H), 4.23 (q, 2H, J=6.8 Hz), 3.65 (s,3H), 1.23 (t, 3H, J=6.8 Hz); IR (KBr, cm$^{-1}$): 3550, 2940, 1610, 1100; Elemental analysis for: C$_{12}$H$_{14}$N$_2$O$_3$; Calculated (%): C 61.52; H 6.02; N 11.96; O 20.49; Found (%): C 61.55; H 6.07; N 11.78; O 20.60.

EXAMPLE 28

6-amino-3-phenoxy-4-hydroxy-1-methyl-2(1H)-quinolinone (compound 24)

In accordance with EXAMPLE 19, ethyl 2-[N-methyl-N-(phenoxyacetyl)amino]-5-aminobenzoate was used instead of ethyl 2-[N-methyl-N-(octyloxyacetyl)amino]-4-[(3,5-dimethoxy-4-hydroxycinnamoyl)amino]-benzoate, the title compound (24) was obtained.

$^1$H-NMR (d$_6$-DMSO, δ-TMS); 10.85 (s, 1H), 7.90~7.23 (m, 8H), 5.65 (bs, 2H), 3.65 (s, 3H), IR (KBr, cm$^{-1}$): 3550, 2940, 1610, 1250, 1100; Elemental analysis for: C$_{16}$H$_{14}$N$_2$O$_3$; Calculated (%): C 68.07; H 5.00; N 9.92; O 17.00; Found (%): C 68.00; H 5.18; N 9.89; O 16.93.

EXAMPLE 29

5-acetylamino-3-ethoxy-4-hydroxy-1-methyl-2(1H)-quinolinone (compound 25)

In accordance with EXAMPLE 20, ethyl 2-N-methyl-N-(ethoxyacetyl)amino]-6-acetylaminobenzoate was used instead of ethyl 2-[N-methyl-N-(octyloxyacetyl)amino]-4-[(3,5-dimethoxy-4-hydroxycinnamoyl)amino]-benzoate, the title compound (25) was obtained.

¹H-NMR (d₆-DMSO, δ-TMS); 11.07 (s, 1H), 10.85 (s, 1H), 7.90~7.23 (m, 3H), 4.22 (m, 2H), 3.65 (s, 3H), 2.35 (s, 3H), 1.23 (t, 3H, J=6.8 Hz); IR (KBr, cm⁻¹): 3550, 2940, 1610, 1250, 1100; Elemental analysis for: $C_{14}H_{16}N_2O_4$; Calculated (%): C 60.86; H 5.84; N 10.14; O 23.16; Found (%): C 60.99; H 5.78; N 10.09; O 23.14.

EXAMPLE 30

6-acetylamino-3-phenoxy-4-hydroxy-1-methyl-2 (1H)-quinolinone (compound 26)

In accordance with EXAMPLE 21, ethyl 2-N-methyl-N-(phenoxyacetyl)amino]-5-acetylaminobenzoate was used instead of ethyl 2-[N-methyl-N-(octyloxyacetyl)amino]-4-[(3,5-dimethoxy-4-hydroxycinnamoyl)amino]-benzoate, the title compound (26) was obtained.

¹H-NMR (d₆-DMSO, δ-TMS); 11.07 (s, 1H<10.85 (s, 1H9, 7.90~7.23 (m, 8H), 3.65 (s, 3H), 2.35 (s, 3H), IR (KBr, cm⁻¹): 3550, 2940, 1610, 1250, 1100; Elemental analysis for: $C_{18}H_{16}N_2O_4$; Calculated (%): C 66.66; H 4.97; N 8.64; O 19.73; Found (%): C 66.54; H 4.90; N 8.66; O 19.90.

EXAMPLE 31

5-propenylamino-3-ethoxy-4-hydroxy-1-methyl-2 (1H)-quinolinone (compound 27)

In accordance with EXAMPLE 22, ethyl 2-[N-methyl-N-(ethoxyacetyl)amino]-6-propenylamino benzoate was used instead of ethyl 2-N-methyl-N-(octyloxyacetyl)amino]-4-[(3,5-dimethoxy-4-hydroxycinnamoyl)amino]-benzoate, the title compound (27) was obtained.

¹H-NMR (d₆-DMSO, δ-TMS); 10.85 (s, 1H, 7.90~7.23 (m, 3H), 5.96 (m, 1H), 5.26 (m, 3H), 4.22 (m, 2H), 3.88 (m, 2H), 3.65 (s, 3H), 1.23 (t, 3H, J=6.8 Hz); IR (KBr, cm⁻¹): 3550, 2940, 1610, 1250, 1100; Elemental analysis for: $C_{15}H_{18}N_2O_3$; Calculated (%): C 65.67; H 6.61; N 10.21; O 17.50; Found (%): C 65.55; H 6.64; N 10.34; O 17.47.

EXAMPLE 32

6-benzylamino-3-phenoxy-4-hydroxy-1-methyl-2 (1H)-quinolinone (compound 28)

In accordance with EXAMPLE 22, ethyl 2-[N-methyl-N-(phenoxyacetyl)amino]-5-benzylamino benzoate was used instead of ethyl 2-[N-methyl-N-(octyloxyacetyl)amino]-4-[(3,5-dimethoxy-4-hydroxycinnamoyl)amino]-benzoate, the title compound (28) was obtained.

¹H-NMR (d₆-DMSO, δ-TMS); 10.85 (s, 1H), 7.90~7.15 (m, 13H), 5.26 (s, 1H), 3.65 (s, 3H), 3.45 (m, 2H); IR (KBr, cm⁻¹): 3550, 2940, 1610, 1250, 1100; Elemental analysis for: $C_{23}H_{33}N_2O_3$; Calculated (%): C 74.17; H 5.41; N 7.52; O 12.89; Found (%): C 74.00; H 5.48; N 7.56; O 12.96.

EXAMPLE 33

5-hydroxy-3-ethoxy-4-hydroxy-1-ethyl-2(1H)-quinolinone (compound 29)

In accordance with EXAMPLE 19, ethyl 2-[N-ethyl-N-(ethoxyacetyl)amino]-6-hydroxybenzoate was used instead of ethyl 2-[N-methyl-N-(octyloxyacetyl)amino]-4-[(3,5-dimethoxy-4-hydroxycinnamoyl)amino]-benzoate, the title compound (29) was obtained.

¹H-NMR (d₆-DMSO, δ-TMS); 11.07 (s, 1H), 10.75 (s, 1H), 7.65~7.13 (m, 3H), 4.22 (m, 2H), 3.65 (t, 2H), 1.23 (m, 6H); IR (KBr, cm⁻¹): 3550, 2940, 1610, 1250, 1100; Elemental analysis for: $C_{13}H_{15}N_1O_4$; Calculated (%): C 62.64; H 6.07; N 5.62; O 25.68; Found (%): C 62.68; H 6.05; N 5.56; O 25.71.

EXAMPLE 34

7-hydroxy-3-octyloxy-4-hydroxy-1-methyl-2(1H)-quinolinone (compound 30)

In accordance with EXAMPLE 20, ethyl 2-[N-methyl-N-(octyloxyacetyl)amino]-4-hydroxybenzoate was used instead of ethyl 2-[N-methyl-N-(octyloxyacetyl)amino]-4-[(3,5-dimethoxy-4-hydroxycinnamoyl)amino]-benzoate, the title compound (30) was obtained.

¹H-NMR (d₆-DMSO, δ-TMS); 11.23 (s, 1H), 9.98 (s, 1H), 7.85 (s, 1H), 7.76 (d, 1H, J=7.2 Hz), 7.50 (d, 1H, J=7.2 Hz), 4.23 (d, 2H, J=7.6 Hz), 3.54 (s, 3H), 1.86~1.45 (m, 12H), 0.97 (t, 3H, J=7.5 Hz); IR (KBr, cm⁻¹): 3550, 2940, 1610, 1250, 1100; Elemental analysis for: $C_{18}H_{25}N_1O_4$; Calculated (%): C 67.69; H 7.89; N 4.39; O 20.04; Found (%): C 67.78; H 7.78; N 4.44; O 20.00.

EXAMPLE 35

5-phenoxy-3-ethoxy-4-hydroxy-1-ethyl-2(1H)-quinolinone (compound 31)

In accordance with EXAMPLE 20, ethyl 2-[N-ethyl-N-(ethoxyacetyl)amino]-6-phenoxybenzoate was used instead of ethyl 2-[-methyl-N-(octyloxyacetyl)amino]-4-[(3,5-dimethoxy-4-hydroxycinnamoyl)amino]-benzoate, the title compound (31) was obtained.

¹H-NMR (d₆-DMSO, δ-TMS); 10.75 (s, 1H), 7.65~7.13 (m, 8H), 4.22 (m, 2H), 3.65 (t, 2H), 1.23 (m, 6H); IR (KBr, cm⁻¹): 3550, 2940, 1610, 1250, 1100; Elemental analysis for: $C_{19}H_{19}N_2O_4$; Calculated (%): C 70.14; H 5.89; N 4.31; O 19.67; Found (%): C 70.08; H 5.78; N 4.46; O 19.68.

EXAMPLE 36

7-methoxy-3-octyloxy-4-hydroxy-1-methyl-2(1H)-quinolinone (compound 32)

In accordance with EXAMPLE 21, ethyl 2-[N-methyl-N-(octyloxyacetyl)amino]-4-methoxybenzoate was used instead of ethyl 2-[N-methyl-N-(octyloxyacetyl)amino]-4-[(3,5-dimethoxy-4-hydroxycinnamoyl)amino]-benzoate, the title compound (32) was obtained.

¹H-NMR (d₆-DMSO, δ-TMS); 11.23 (s,1H), 7.85 (s, 1H), 7.76 (d, 1H, J=7.2 Hz), 7.50 (d, 1H, J=7.2 Hz), 4.23 (d, 2H, J=7.6 Hz), 3.78 (s, 3H), 3.54 (s, 3H), 1.86~1.45 (m, 12H), 0.97 (t, 3H, J=7.5 Hz); IR (KBr, cm⁻¹): 3550, 2940, 1610, 1250, 1100; Elemental analysis for: $C_{19}H_{27}N_1O_4$; Calculated (%): C 68.44; H 8.16; N 4.20; O 19.20; Found (%): C 68.24; H 8.28; N 4.21; O 19.27.

EXAMPLE 37

7-butoxy-3-octyloxy-4-hydroxy-1-propenyl-2(1H)-quinolinone (compound 33)

In accordance with EXAMPLE 21, ethyl 2-[N-propenyl-N-(octyloxyacetyl)amino]-4-butoxybenzoate was used instead of ethyl 2-[N-methyl-N-(octyloxyacetyl)amino]-4-[(3,5-dimethoxy-4-hydroxycinnamoyl)amino]-benzoate, the title compound (33) was obtained.

¹H-NMR (d₆-DMSO, δ-TMS); 11.02 (s, 1H), 7.85 (s, 1H), 7.76 (d, 1H, J=7.2 Hz), 7.50 (d, 1H, J=7.2 Hz), 5.95 (m, 1H), 510 (m, 2H), 4.23 (m, 4H), 3.30 (d, 2H, J=7.2 Hz), 1.86~1.45 (m, 16H9, 0.97 (m, 6H); IR (KBr, cm$^{-1}$): 3550, 2940, 1610, 1250, 1100; Elemental analysis for: $C_{24}H_{35}N_1O_4$; Calculated (%): C 71.79; H 8.79; N 3.49; O 15.94; Found (%):C 71.67; H 8.66; N 3.48; O 16.19.

EXAMPLE 38

6-phenyl-3-phenoxy-4-hydroxy-1-octyl-2(1H)-quinolinone (compound 34)

In accordance with EXAMPLE 22, ethyl 2-[N-octyl-N-(phenoxyacetyl)amino]-5-20 phenylbenzoate was used instead of ethyl 2-[N-methyl-N-(octyloxyacetyl)amino]-4-[(3,5-dimethoxy-4-hydroxycinnamoyl)amino]-benzoate, the title compound (34) was obtained.

$^1$H-NMR (d$_6$-DMSO, δ-TMS); 10.85 (s, 1H), 7.90~7.15 (m, 13H), 3.65 (d, 2H, J=6.8 Hz), 1.84~1.23 (m, 12H), 0.90 (t,3H, J=6.8 Hz); IR (KBr, cm$^{-1}$): 3550, 2940, 1610, 1250, 1100; Elemental analysis for: $C_{29}H_{31}N_1O_4$; Calculated (%): C 76.12; H 6.83; N 3.06; O 13.99; Found (%): C 76.01; H 6.87; N 3.05; O 14.07.

EXAMPLE 39

7-methyl-3-octyloxy-4-hydroxy-1-methyl-2(1H)-quinolinone (compound 35)

In accordance with EXAMPLE 22, ethyl 2-[N-methyl-N-(octyloxyacetyl)amino]-4-methylbenzoate was used instead of ethyl 2-[N-methyl-N-(octyloxyacetyl)amino]-4-[(3,5-dimethoxy-4-hydroxycinnamoyl)amino]-benzoate, the title compound (35) was obtained.

$^1$H-NMR (d$_6$-DMSO, δ-TMS); 11.23 (s, 1H), 7.85 (s, 1H), 7.76 (d, 1H, J=7.2 Hz), 7.50 (d, 1H, J=7.2 Hz), 4.23 (d, 2h, J=7.6 Hz), 3.54 (s, 3H), 2.25 (s, 3H), 1.86~1.45 (m, 12H), 0.97 (t, 3H, J=7.5 Hz); IR (KBr, cm$^{-1}$): 3550, 2940, 1610, 1250, 1100; Elemental analysis for: $C_{19}11_{27}N_1O_3$; Calculated (%): C 71.89; H 8.57; N 4.41; O 15.12; Found (%): C 71.77; H 8.43; N 4.45; O 15.35.

EXAMPLE 40

5,7-dihydroxy-3-methoxy-4-hydroxy-1-methyl-2 (1H)-quinolinone (compound 36)

In accordance with EXAMPLE 19, ethyl 2-[N-methyl-N-(methoxyacetyl)amino]-4,6-dihydroxy-benzoate was used instead of ethyl 2-[N-methyl-N-(octyloxyacetyl)amino]-4-[(3,5 -dimethoxy-4-hydroxycinnamoyl)amino]-benzoate, the title compound (36) was obtained.

$^1$H-NMR (d$_6$-DMSO, δ-TMS); 11.23 (s, 111), 10.87 (s, 1H), 10.23 (s, 1H), 7.56 (s, 1H), 7.50 (s, 1H), 3.89 (s, 3H), 3.64 (s, 3H); IR (KBr, cm$^{-1}$): 3550, 2940, 1610, 1250, 1100; Elemental analysis for: $C_{11}H_{11}N_1O_5$; Calculated (%): C 71.06; H 7.16; N 6.63; O 15.15; Found (%): C 71.00; H 7.28; N 6.56; O 15.16.

EXAMPLE 41

5,7-dibenzyloxy-3-geranyloxy-4-hydroxy-1-benzyl-2(1H)-quinolinone (compound 37)

In accordance with EXAMPLE 19, ethyl 2-[N-benzyl-N-(geranyloxyacetyl)amino]-4,6-dibenzyloxy-benzoate was used instead of ethyl 2-[N-methyl-N-(octyloxyacetyl) amino]-4-[(3,5-dimethoxy-4-hydroxycinnamoyl)amino]-benzoate, the title compound (37) was obtained.

$^1$H-NMR (d$_6$-DMSO, δ-TMS); 10.87 (s, 1H), 7.65~7.13 (m, 23H), 5.40 (m, 1H), 4.12 (m, 2H), 2.15~1.60 (m, 13H); IR (KBr, cm$^{-1}$): 3550, 2940, 1610, 1250, 1100; Elemental analysis for: $C_{40}H_{41}N_1O_5$; Calculated (%): C 78.02; H 6.71; N 2.27; O 12.99; Found (%): C 78.00; H 6.78; N 2.34; O 12.88.

EXAMPLE 42

5-ethoxycarbonyl-3-butoxy-4-hydroxy-1-methyl-2 (1H)-quinolinone (compound 38)

In accordance with EXAMPLE 20, ethyl 2-[N-methyl-N-(butoxyacetyl)amino]-6-ethoxycarbonylbenzoate was used instead of ethyl 2-[N-methyl-N-(octyloxyacetyl)amino]-4-[(3,5-dimethoxy-4-hydroxycinnamoyl)amino]-benzoate, the title compound (38) was obtained.

$^1$H-NMR (d$_6$-DMSO, δ-TMS); 10.68 (s, 1H), 7.88~7.55 (m, 3H), 4.22 (t, 2h, J=6.9 Hz), 3.84 (t, 2H, J=6.8 Hz), 3.62 (s, 3H), 1.78~1.34 (m, 4H), 1.22 (t, 3H, J=6.8 Hz), 0.96 (t, 3H, J=6.8 Hz); IR (KBr, cm$^{-1}$): 3550,2940, 1715, 1610, 1250, 1100; Elemental analysis for: $C_{40}H_{41}N_1O_5$; Calculated (%): C 63.93; H 6.63; N 4.39; O 25.05; Found (%): C 63.99; H 6.56; N 4.23; O 25.22.

EXAMPLE 43

7-nitro-3-methoxy-4-hydroxy-1-(2-hydroxyethyl)-2 (1H)-quinolinone (compound 39)

In accordance with EXAMPLE 21, ethyl 2-[N-(2-hydroxyethyl)-N-(methoxyacetyl)amino]-4-nitrobenzoate was used instead of ethyl 2-[N-methyl-N-(octyloxyacetyl)amino]-4-[(3,5-dimethoxy-4-hydroxycinnamoyl)amino]-benzoate, the title compound (39) was obtained.

$^1$H-NMR (d$_6$-DMSO, δ-TMS); 11.05 (s, 1H), 8.05 (m, 3H), 3.75 (s, 3H), 3.68 (s, 3H), 2.88 (m, 2H); IR(KBr, cm$^{-1}$): 3550, 2940, 1610, 1515, 1400, 1250; Elemental analysis for: $C_{12}H_{12}N_2O_6$; Calculated (%): C 51.43; H 4.32; N 9.99; O 34.26; Found (%): C 51.33; H 4.35; N 10.01; O 34.31.

EXAMPLE 44

7-acetylamino-3-octyloxy-4-hydroxy-1-methyl-2 (1H)-quinolinone (compound 19)

In accordance with EXAMPLE 19, ethyl 2-[N-methyl-N-(octyloxyacetyl)amino]-4-acetylaminobenzoate and magnesium ethoxide were used instead of ethyl 2-[N-methyl-N-(octyloxyacetyl)amino]-4-[(3,5-dimethoxy-4-hydroxycinnamoyl)amino]-benzoate and potassium tert-butoxide, the title compound (19) was obtained.

EXAMPLE 45

7-acetylamino-3-octyloxy-4-hydroxy-1-methyl-2 (1H)-quinolinone (compound 19)

In accordance with EXAMPLE 20, ethyl 2-[N-methyl-N-(octyloxyacetyl)amino]-4-acetylaminobenzoate and calcium hydridewere used instead of ethyl 2-[N-methyl-N-(octyloxyacetyl)amino]-4-[(3,5-dimethoxy-4-hydroxycinnamoyl)amino]-benzoate and sodium hydride, the title compound (19) was obtained.

EXAMPLE 46

5-nitro-3-methoxy-4-hydroxy-1 -ethyl-2(11H)-quinolinone (compound 40)

In accordance with EXAMPLE 25, ethyl 2-[N-ethyl-N-(methoxyacetyl)amino]-6-nitrobenzoate was used instead of ethyl 2-[N-methyl-N-(octyloxyacetyl)amino]-4-[(3,5-dimethoxy-4-hydroxycinnamoyl)amino]-benzoate, the title compound (40) was obtained.

$^1$H-NMR (d$_6$-DMSO, δ-TMS); 11.05 (s, 1H), 8.09 (m, 3H), 3.75 (s, 3H), 3.68 (d, 2H, J=6.8 Hz),1.23 (t, 3H, J=6.8 Hz); IR (KBr, cm$^{-1}$): 3550, 2940, 1610, 1515, 1250, 1100; Elemental analysis for: C$_{12}$H$_{12}$N$_2$O$_5$; Calculated (%): C 54.54; H 4.58; N 10.60; O 30.28; Found (%): C 54.43; H 4.58; N 10.67; O 30.45.

EXAMPLE 47

6-nitro-3-butoxy-4-hydroxy-1-decyl-2(1H)-quinolinone (compound 41)

In accordance with EXAMPLE 19, ethyl 2-[N-decyl-N-(butoxyacetyl)amino]5-nitrobenzoate was used instead of ethyl 2-[N-methyl-N-(octyloxyacetyl)amino]-4-[(3,5-dimethoxy-4-hydroxycinnamoyl)amino]-benzoate, the title compound (41) was obtained.

$^1$H-NMR (d$_6$-DMSO, δ-TMS); 11.05 (s, 1H), 8.09 (m, 3H), 4.12 (d, 2H, J=6.8 Hz), 3.75 (d, 2H, J=6.9 Hz), 2.23~1.23 (m, 20H), 0.90 (m, 6H); IR (KBr, cm$^{-1}$): 3550, 2940, 1610, 1515, 1250, 1100; Elemental analysis for: C$_{23}$H$_{34}$N$_2$O$_5$; Calculated (%): C 66.00; H 8.19; N 6.69; O 19.12; Found (%): C 66.09; H 8.09; N 6.67; O 19.15.

EXAMPLE 48

8-nitro-3-methoxy-4-hydroxy-1-benzyl-2(1H)-quinolinone (compound 42)

In accordance with EXAMPLE 19, ethyl 2-[N-benzyl-N-(methoxyacetyl)amino]-3-nitrobenzoate was used instead of ethyl 2-[N-methyl-N-(octyloxyacetyl)amino]-4-[(3,5-dimethoxy-4-hydroxycinnamoyl)amino]-benzoate, the title compound (42) was obtained.

$^1$H-NMR (d$_6$-DMSO, δ-TMS); 11.05 (s, 1H), 8.09 (m, 3H), 7.25 (m, 5H), 5.23 (s, 2H), 3.89 (s, 3H); IR (KBr, cm$^{-1}$): 3550, 2940, 1610, 1515, 1250, 1100; Elemental analysis for: C$_{17}$H$_{14}$N$_2$O$_5$; Calculated (%): C 62.57; H 4.32; N 8.59; O 24.52; Found (%): C 62.45; H 4.45; N 8.67; O 24.43.

EXAMPLE 49

6-nitro-3-butoxy-4-hydroxy-1-(6-hydroxyhexyl)-2(11H)-quinolinone (compound 43)

In accordance with EXAMPLE 19, ethyl 2-[N-(6-hydroxyhexyl)-N-(butoxyacetyl)amino]-5-nitrobenzoate was used instead of ethyl 2-[N-methyl-N-(octyloxyacetyl)amino]-4-[(3,5-dimethoxy-4-hydroxycinnamoyl)amino]-benzoate, the title compound (43) was obtained.

$^1$H-NMR (d$_6$-DMSO, δ-TMS); 11.05 (s, 1H), 8.05 (m, 3H), 4.12 (d, 2H, j=6.8 Hz), 3.87 (m, 3H), 3.75 (d, 2H, J=6.9 Hz), 2.23~1.23 (m, 12H), 0.90 (t, 3H, J=6.8 Hz); IR (KBr, cm$^{-1}$): 3550, 2940, 1610, 1515, 1250, 1100; Elemental analysis for: C$_{19}$H$_{25}$N$_2$O$_6$; Calculated (%): C 60.30; H 6.93; N 7.40; O 25.38; Found (%): C 60.24; H 7.09; N 7.28; O 25.39.

EXAMPLE 50

5-amino-3-ethoxy-4-hydroxy-1-geranyl-2(1H)-quinolinone (compound 44)

In accordance with EXAMPLE 20, ethyl 2-[N-geranyl-N-(ethoxyacetyl)amino]-6-aminobenzoate was used instead of ethyl 2-[N-methyl-N-(octyloxyacetyl)amino]-4-[(3,5-dimethoxy-4-hydroxycinnamoyl)amino]-benzoate, the title compound (44) was obtained.

$^1$H-NMR (d$_6$-DMSO, δ-TMS); 10.87 (s, 1H), 7.65~7.06 (m, 3H), 5.40 (m, 1H), 5.25 (m, 2H), 5.10 (m, 1H), 4.12 (m, 2H), 3.34 (m, 2H), 2.15~1.60 (m, 13H), 1.23 (t, 3H, J=7.2 Hz); IR (KBr, cm$^{-1}$): 3550, 2940, 1610, 1515, 1250, 1100; Elemental analysis for: C$_{21}$H$_{28}$N$_2$O$_3$; Calculated (%): C 70.76; H 7.92; N 7.86; O 13.47; Found (%): C 70.74; H 7.89; N 7.78; O 25.39.

EXAMPLE 51

8-amino-3-geranyloxy-4-hydroxy-1-methyl-2(1H)-quinolinone (compound 45)

In accordance with EXAMPLE 20, ethyl 2-[N-methyl-N-(geranyloxyacetyl)amino]-3-aminobenzoate was used instead of ethyl 2-[N-methyl-N-(octyloxyacetyl)amino]-4-[(3,5-dimethoxy-4-hydroxycinnamoyl)amino]-benzoate, the title compound (45) was obtained.

$^1$H-NMR (d$_6$-DMSO, δ-TMS); 10.87 (s, 1H), 7.65~7.06 (m, 3H), 5.40 (m, 1H), 5.25 (m, 2H), 5.10 (m, 1H), 4.23 (m, 2H), 3.67 (s, 3H), 2.15~1.60 (m, 13H); IR (KBr, cm$^{-1}$): 3550,2940, 1610, 1515, 1250, 1100; Elemental analysis for: C$_{20}$H$_{35}$N$_2$O$_3$; Calculated (%): C 70.15; H 7.65; N 8.18; O 14.02; Found (%): C 70.18; H 7.79; N 7.98; O 14.05.

EXAMPLE 52

7-[(3,4,5-trimethoxycinnamoyl)amino]-3-octyloxy-4-hydroxy-1-methyl-2(1H)-quinolinone (compound 46)

In accordance with EXAMPLE 21, ethyl 2-[N-methyl-N-(octyloxyacetyl)amino]-4-[(3,4,5-trimethoxycinnamoyl)amino]-benzoate was used instead of ethyl 2-[N-methyl-N-(octyloxyacetyl)amino]-4-[(3,5-dimethoxy-4-hydroxycinnamoyl)amino]-benzoate, the title compound (46) was obtained.

$^1$H-NMR (d$_6$-DMSO, δ-TMS); 10.39 (s, 1H), 8.92 (s, 1H), 7.99 (s, 1H), 7.85 (d, 1H, J=8.8 Hz), 7.53 (d, 1H, J=15.6 Hz), 7.49 (s, 1H), 6.93 (s, 2H), 6.75 (d, 1H, J=15.6 Hz), 3.92 (t, 2H, J=6.8 Hz), 3.78 (s, 9H), 3.54 (s, 3H), 1.68 (m, 2H), 1.25 (m, 10H), 0.86 (t, 3H, J=6.8 Hz); IR (KBr, cm$^{-1}$): 3550, 2940, 1600, 1515, 1250, 1100; Elemental analysis for: C$_{30}$H$_{38}$N$_2$O$_7$; Calculated (%): C 66.89; H 7.12; N 5.20; O 20.79; Found (%): C 66.78; H 7.08; N 5.23; O 20.91.

EXAMPLE 53

5-methylamino-3-benzyloxy-4-hydroxy-1-methyl-2(1H)-quinolinone (compound 47)

In accordance with EXAMPLE 21, ethyl 2-[N-methyl-N-(benzyloxyacetyl)amino]-6-methylaminobenzoate was used instead of ethyl 2-[N-methyl-N-(octyloxyacetyl)amino]-4-[(3,5-dimethoxy-4-hydroxycinnamoyl)amino]-benzoate, the title compound (47) was obtained.

$^1$H-NMR (d$_6$-DMSO, δ-TMS); 10.85 (s, 1H), 7.88~7.20 (m, 8H), 5.70 (bs, 1H), 5.15 (s, 2H), 3.65 (s, 3H), 2.78)s, 3H); IR (K br, cm$^{-1}$): 3550, 2940, 1610, 1515, 1100; Elemental analysis for: C$_{18}$H$_{18}$N$_2$O$_3$; Calculated (%): C 69.66; H 5.85; N 9.03; O 15.47; Found (%): C 69.78; H 5.78; N 9.00; O 15.44.

EXAMPLE 54

5-hexylamino-3-(3,5-dimethylbenzyloxy)-4-hydroxy-1-ethyl-2(1H)-quinolinone (compound 48)

In accordance with EXAMPLE 21, ethyl 2-[N-ethyl-N-(3,5-dimethylbenzyloxy acetyl)amino]-6- hexylaminobenzoate was used instead of ethyl 2-[N-methyl-N-(octyloxyacetyl)amino]-4-[(3,5-dimethoxy-4-hydroxycinnamoyl)amino]-benzoate, the title compound (48) was obtained.

$^1$H-NMR (d$_6$-DMSO, δ-TMS); 10.85 (s, 1H), 7.88~7.20 (m, 6H), 5.65 (bs, 1H), 5.13 (s, 2H), 3.65 (d, 2H, J=7.2 Hz), 2.89 (t, 2H, J=6.9 Hz), 1.86~1.23 (m, 8H), 2.18 (s, 6H), 1.15 (t, 3H, J=7.2 Hz), 0.90 (t, 3H, J=6.9 Hz); IR (KBr, cm$^{-1}$): 3550, 2940, 1610, 1100; Elemental analysis for: C$_{26}$H$_{34}$N$_2$O$_3$; Calculated (%): C 73.90; H 8.11; N 6.63; O 11.36; Found (%): C 73.88; H 8.05; N 6.69; O 11.38.

EXAMPLE 55

6-decylamino-3-methoxy-4-hydroxy-1-methyl-2 (1H)-quinolinone (compound 49)

In accordance with EXAMPLE 21, ethyl 2-[N-methyl-N-(methoxyacetyl)amino]-5-decylaminobenzoate was used instead of ethyl 2-[N-methyl-N-(octyloxyacetyl)amino]-4-[(3,5-dimethoxy-4-hydroxycinnamoyl)amino]-benzoate, the title compound (49) was obtained.

$^1$H-NMR (d$_6$-DMSO, δ-TMS); 10.85 (s, 1H), 7.88~7.40 (m, 3H), 5.65 (bs, 1H), 3.79 (s, 3H), 3.65 (s, 3H), 2.78 (t, 2H, J=6.9 Hz), 1.89~1.18 (m, 16H), 0.90 (t, 3H, J=6.9 Hz); IR (KBr, cm$^{-1}$): 3550, 2940, 1610, 1100; Elemental analysis for: C$_{21}$H$_{32}$N$_2$O$_3$; Calculated (%): C 69.97; H 8.95; N 7.77; O 13.32; Found (%) C 69.98; H 8.95; N 7.58; O 13.49.

EXAMPLE 56

6-vinylamino-3-methoxy-4-hydroxy-1-methyl-2 (11H)-quinolinone (compound 50)

In accordance with EXAMPLE 22, ethyl 2-[N-methyl-N-(methoxyacetyl)amino]-5-vinylaminobenzoate was used instead of ethyl 2-[N-methyl-N-(octyloxyacetyl)amino]-4-[(3,5-dimethoxy-4-hydroxycinnamoyl)amino]-benzoate, the title compound (50) was obtained.

$^1$H-NMR (d$_6$-DMSO, δ-TMS); 10.85 (s, 1H), 7.88~7.40 (m, 3H), 6.23 (m, 1H), 5.26 (s, 1H), 4.90 (m, 1H), 4.56 (m, 1H), 3.87 (s, 3H), 3.65 (s, 3H); IR (KBr, cm$^{-1}$): 3550, 2940, 1610, 1100; Elemental analysis for: C$_{13}$H$_{14}$N$_2$O$_3$; Calculated (%): C 63.40; H 5.73; N 11.38; O 19.49; Found (%): C 63.39; H 5.78; N 11.45; O 19.38.

EXAMPLE 57

6-(3, 5 -dimethylbenzylamino]-3-methoxy-4-hydroxy-1-methyl-2(1H)-quinolinone (compound 51)

In accordance with EXAMPLE 22, ethyl 2-[N-methyl-N-(methoxyacetyl)amino]-5-(3,5-dimethylbenzylamino)-benzoate was used instead of ethyl 2-[N-methyl-N-(octyloxyacetyl)amino]-4-[(3,5-dimethoxy-4-hydroxycinnamoyl)amino]-benzoate, the title compound (51) was obtained.

$^1$H-NMR (d$_6$-DMSO, δ-TMS); 10.85 (s, 1H), 7.88 ~7.20 (m, 6H), 5.65 (bs, 1H), 3.78 (s, 3H), 3.56 (s, 3H), 3.06 (s, 2H), 2.18 (s, 6H); IR (KBr, cm$^{-1}$): 3550, 2940, 1610, 1100; Elemental analysis for: C$_{20}$H$_{22}$N$_2$O$_3$; Calculated (%): C 70.98; H 6.55; N 8.28; O 14.18; Found (%): C 71.01; H 6.45; N 8.33; O 14.21.

EXAMPLE 58

6-geranylamino-3-methoxy-4-hydroxy-1-methyl-2 (1H)-quinolinone (compound 52)

In accordance with EXAMPLE 19, ethyl 2-[N-methyl-N-(methoxyacetyl)amino]-5-geranylaminobenzoate was used instead of ethyl 2-[N-methyl-N-(octyloxyacetyl)amino]-4-[(3,5-dimethoxy-4-hydroxycinnamoyl)amino]-benzoate, the title compound (52) was obtained.

$^1$H-NMR (d$_6$-DMSO, δ-TMS); 10.85 (s, 1H), 7.68~7.20 (m, 3H), 5.65 (bs, 1H), 5.45 (m, 1H), 5.08 (m, 1H), 3.78 (s, 3H), 3.56 (s, 3H), 3.34 (d, 2H, J=7.5 Hz), 2.25~1.55 (m, 13H); IR (KBr, cm$^{-1}$): 3550, 2940, 1610, 1100; Elemental analysis for: C$_{21}$H$_{28}$N$_2$O$_3$; Calculated (%): C 70.76; H 7.92; N 7.86; O 13.47; Found (%): C 70.67; H 7.96; N 7.87; O 13.50.

EXAMPLE 59

8-butylamino-3-geranyloxy-4-hydroxy-1-methyl-2 (1H)-quinolinone (compound 53)

In accordance with EXAMPLE 19, ethyl 2-[N-methyl-N-(geranyloxyacetyl)amino]-3-butylaminobenzoate was used instead of ethyl 2-[N-methyl-N-(octyloxyacetyl)amino]4-[(3,5-dimethoxy-4-hydroxycinnamoyl)amino]-benzoate, the title compound (53) was obtained.

$^1$H-NMR (d$_6$-DMSO, δ-TMS); 10.85 (s, 1H), 7.68~7.20 (m, 3H), 5.58 (bs, 1H), 5.45 (m, 1H), 5.08 (m, 1H), 4.12 (d, 2H, J=7.5 Hz), 3.56 (s, 3H), 2.89 (d, 2H, J=7.2 Hz), 2.25~1.55 (m, 17H), 0.90 (t, 3H, J=6.9 Hz); IR (KBr, cm$^{-1}$): 3550, 2940, 1610, 1100; Elemental analysis for: C$_{24}$H$_{34}$N$_2$O$_3$; Calculated (%): C 72.33; H 8.60; N 7.03; O 12.04; Found (%): C 72.18; H 8.59; N 7.07; O 12.16.

EXAMPLE 60

6-decyloxy-3-methoxy-4-hydroxy-1-methyl-2(1H)-quinolinone (compound 54)

In accordance with EXAMPLE 20, ethyl 2-[N-methyl-N-(methoxyacetyl)amino]-5-decyloxybenzoate was used instead of ethyl 2-[N-methyl-N-(octyloxyacetyl)amino]-4-[(3,5-dimethoxy-4-hydroxycinnamoyl)amino]-benzoate, the title compound (54) was obtained.

$^1$H-NMR (d$_6$-DMSO, δ-TMS); 10.85 (s, 1H), 7.68~7.20 (m, 3H), 4.18 (d, 2H, J=7.2 Hz), 3.80 (d, 2H), 3.56 (s, 3H), 1.86~1.18 (m, 16H), 0.90 (t, 3H, J=6.9 Hz); IR (KBr, cm$^{-1}$): 3550, 2940, 1610, 1100; Elemental analysis for: C$_{21}$H$_{31}$N$_1$O$_4$; Calculated (%): C 69.77; H 8.65; N 3.88; O 17.71; Found (%): C 69.68; H 8.59; N 3.90; O 17.83.

EXAMPLE 61

6-(2-propenyloxy)-3-phenoxy-4-hydroxy-1-octyl-2 (1H)-quinolinone (compound 55)

In accordance with EXAMPLE 20, ethyl 2-[N-octyl-N-(phenoxyacetyl)amino]-5-(2-propenyloxy)-benzoate was used instead of ethyl 2-[N-methyl-N-(octyloxyacetyl) amino]-4-[(3,5-dimethoxy-4-hydroxycinnamoyl)amino]-benzoate, the title compound (55) was obtained.

$^1$H-NMR (d$_6$-DMSO, δ-TMS); 10.85 (s, 1H), 7.75~7.20 (m, 8H), 5.80 (m, 1H), 5.25 (m, 2H), 4.45 (m, 2H), 3.67 (t, 2H, J=7.4 Hz), 1.86~1.18 (m, 12H), 0.90 (t, 3H, J=6.9 Hz); IR (KBr, cm$^{-1}$): 3550, 2940, 1610, 1100; Elemental analysis for: C$_{26}$H$_{31}$N$_1$O$_4$; Calculated (%): C 74.08; H 7.41; N 3.32; O 15.18; Found (%): C 74.10; H 7.43; N 3.40; O 15.07.

EXAMPLE 62

8-benzyloxy-3-geranyloxy-4-hydroxy-1-benzyl-2 (1H)-quinolinone (compound 56)

In accordance with EXAMPLE 21, ethyl 2-[N-benzyl-N-(geranyloxyacetyl)amino]-3-benzylbenzoate was used instead of ethyl 2-[N-methyl-N-(octyloxyacetyl)amino]-4-[(3,5-dimethoxy-4-hydroxycinnamoyl)amino]-benzoate, the title compound (56) was obtained.

$^1$H-NMR (d$_6$-DMSO, δ-TMS); 10.85 (s, 1H), 7.75~7.20 (m, 13H), 5.40 m, 1H), 5.10 (m, 1H), 5.20(s, 2H), 4.24 (t, 2H, J=7.4 Hz), 3.67 (s, 2H), 2.15~1.45 (m, 13H); IR (KBr, cm$^{-1}$): 3550, 2940, 1610, 1100; Elemental analysis for: C$_{33}$H$_{35}$N$_1$O$_4$; Calculated (%): C 77.77; H 6.92; N 2.75; O 12.56; Found (%): C 77.88; H 6.89; N 2.76; O 12.47.

EXAMPLE 63

7-methyl-3-methoxy-4-hydroxy-1-methyl-2(1H)-quinolinone (compound 57)

In accordance with EXAMPLE 21, ethyl 2-[N-methyl-N-(methoxyacetyl)amino]-4-methylbenzoate was used instead of ethyl 2-[N-methyl-N-(octyloxyacetyl)amino]-4-[(3,5-dimethoxy-4-hydroxycinnamoyl)amino]-benzoate, the title compound (57) was obtained.

$^1$H-NMR (d$_6$-DMSO, δ-TMS); 10.85 (s, 1H), 7.75~7.20 (m, 3H), 3.78 (s, 3H), 3.65 (s, 3H), 2.15 (s, 3H); IR (KBr, cm$^{-1}$): 3550, 2940, 1610, 1100; Elemental analysis for: C$_{12}$H$_{13}$N$_1$O$_3$; Calculated (%): C 65.74; H 5.98; N 6.93; O 21.89; Found (%): C 65.77; H 5.89; N 6.55; O 21.79.

EXAMPLE 64

7-hexyl-3-methoxy-4-hydroxy-1-methyl-2(1H)-quinolinone (compound 58)

In accordance with EXAMPLE 21, ethyl 2-[N-methyl-N-(methoxyacetyl)amino]-4-hexylbenzoate was used instead of ethyl 2-[N-methyl-N-(octyloxyacetyl)amino]-4-[(3,5-dimethoxy-4-hydroxycinnamoyl)amino]-benzoate, the title compound (58) was obtained.

$^1$H-NMR (d$_6$-DMSO, δ-TMS); 10.85 (s, 1H), 7.75~7.20 (m, 3H), 3.74 (s, 3H), 3.65 (s, 3H), 2.22 (d, 2H, J=7.0 Hz), 1.78~1.23 (m, 8H), 0.89 (t, 3H, J=7.0 Hz); IR (KBr, cm$^{-1}$): 3550, 2940, 1610, 1100; Elemental analysis for: C$_{17}$H$_{23}$N$_1$O$_3$; Calculated (%): C 70.56; H 8.01; N 4.84; O 16.59; Found (%): C 70.55; H 7.97; N 4.87; O 16.61.

EXAMPLE 65

7-decyl-3-methoxy-4-hydroxy-1-methyl-2(1H)-quinolinone (compound 59)

In accordance with EXAMPLE 22, ethyl 2-[N-methyl-N-(methoxyacetyl)amino]-4-decylbenzoate was used instead of ethyl 2-[N-methyl-N-(octyloxyacetyl)amino]4-[(3,5-dimethoxy-4-hydroxycinnamoyl)amino]-benzoate, the title compound (59) was obtained.

$^1$H-NMR (d$_6$-DMSO, δ-TMS); 10.85 (s, 1H), 7.75~7.20 (m, 3H), 3.74 (s, 3H), 3.69 (s, 3H), 2.14 (d, 2H, J=7.0 Hz), 1.78~1.23 (m, 16H), 0.89 (t, 3H, J=7.0 Hz); IR (KBr, cm$^{-1}$): 3550, 2940, 1610, 1100; Elemental analysis for: C$_{21}$H$_{31}$N$_1$O$_3$; Calculated (%): C 73.00; H 9.05; N 4.05; O 13.89; Found (%): C 72.89; H 8.97; N 4.03; O 14.11.

EXAMPLE 66

6-(2-propenyl)-3-methoxy-4-hydroxy-1-methyl-2(1H)-quinolinone (compound 60)

In accordance with EXAMPLE 22, ethyl 2-[N-methyl-N-(methoxyacetyl)amino]-5-(2-propenyl) -benzoate was used instead of ethyl 2-[N-methyl-N-(octyloxyacetyl)amino]-4-[(3,5-dimethoxy-4-hydroxycinnamoyl)amino]-benzoate, the title compound (60) was obtained.

$^1$H-NMR (d$_6$-DMSO, δ-TMS); 10.85 (s, 1H), 7.75~7.20 (m, 3H), 6.06 (m, 1H), 5.33 (m, 1H), 5.15 (m, 1H), 3.74 (s, 3H), 3.69 (s, 3H), 3.23 (m, 2H); IR (KBr, cm$^{-1}$): 3550, 2940, 1610, 1100; Elemental analysis for: C$_{14}$H$_{15}$N$_1$O$_3$; Calculated (%): C 68.55; H 6.16; N 5.71; O 19.57; Found (%): C 68.45; H 6.23; N 5.69; O 19.63.

EXAMPLE 67

6-geranyl-3-methoxy-4-hydroxy-1-methyl-2(1H)-quinolinone (compound 61)

In accordance with EXAMPLE 22, ethyl 2-[N-methyl-N-(methoxyacetyl)amino]5-geranylbenzoate was used instead of ethyl 2-[N-methyl-N-(octyloxyacetyl)amino]-4-[(3,5-dimethoxy-4-hydroxycinnamoyl)amino]-benzoate, the title compound (61) was obtained.

$^1$H-NMR (d$_6$-DMSO, δ-TMS); 10.85 (s, 1H), 7.75~7.15 (m, 3H), 5.42 (m, 1H), 5.10 (m, 1H), 3.74 (s, 3H), 3.69 (s, 3H), 2.23 1.55 (m, 15H); IR (KBr, cm$^{-1}$): 3550, 2940, 1610, 1100; Elemental analysis for: C$_{21}$H$_{27}$N$_1$O$_3$; Calculated (%): C 73.87; H 7.97; N 4.10; O 14.06; Found (%): C 73.78; H 7.87; N 4.09; O 14.26.

EXAMPLE 68

5-butyl-3-ethoxy-4-hydroxy-1-ethyl-2(1H)-quinolinone (compound 62)

In accordance with EXAMPLE 19, ethyl 2-[N-ethyl-N-(ethoxyacetyl)amino]-6-butylbenzoate was used instead of ethyl 2-[N-methyl-N-(octyloxyacetyl)amino]-4-[(3,5-dimethoxy-4-hydroxycinnamoyl)amino]-benzoate, the title compound (62) was obtained.

$^1$H-NMR (d$_6$-DMSO, δ-TMS); 10.78 (s, 1H), 7.75~7.15 (m, 3H), 4.23 (d, 2H, J-7.3 Hz), 3.68 (d, 2H, J=6.8 Hz), 2.34 (d, 2H, J=7.1 Hz), 1.85~1.23 (m, 10H), 0.90 (t, 3H, J=6.9 Hz); IR (KBr, cm$^{-1}$): 3550, 2940, 1610, 1100; Elemental analysis for: C$_{17}$H$_{23}$N$_1$O$_3$; Calculated (%): C 70.56; H 8.01; N 4.84; O 16.59; Found (%): C 70.45; H 7.99; N 4.89; O 16.67.

EXAMPLE 69

8-methyl-3-geranyloxy-4-hydroxy-1-benzyl-2(1H)-quinolinone (compound 63)

In accordance with EXAMPLE 20, ethyl 2-[N-benzyl-N-(geranyloxyacetyl)amino]-3-methylbenzoate was used instead of ethyl 2-[N-methyl-N-(octyloxyacetyl)amino]-4-[(3,5-dimethoxy-4-hydroxycinnamoyl)amino]-benzoate, the title compound (63) was obtained.

$^1$H-NMR (d$_6$-DMSO, δ-TMS); 10.78 (s, 1H), 7.79~7.15 (m, 8H), 4.33 (s, H), 4.24 (d, 2H, J=7.3 Hz), 2.34 (d, 2H, J=7.1 Hz), 2.25 (s, 3H), 2.34~1.56 (m, 13H); IR (KBr, cm$^{-1}$): 3550, 2940, 1610, 1100; Elemental analysis for: C$_{27}$H$_{31}$N$_1$O$_3$; Calculated (%): C 77.66; H 7.48; N 3.35; O 11.50; Found (%): C 77.65; H 7.39; N 3.32; O 11.64.

EXAMPLE 70

7-butyl-3-octyloxy-4-hydroxy-1-(2-propenyl)-2(1H)-quinolinone (compound 64)

In accordance with EXAMPLE 21, ethyl 2-[N-(2-propenyl)-N-(octyloxyacetyl)amino]-4-butylbenzoate was used instead of ethyl 2-[N-methyl-N-(octyloxyacetyl) amino]-4-[(3,5-dimethoxy-4-hydroxycinnamoyl)amino]-benzoate, the title compound (64) was obtained.

¹H-NMR (d₆-DMSO, δ-TMS); 10.78 (s, 1H), 7.80~7.15 (m, 3H), 5.95 (m, 1H), 5.20~5.00 (m, 2H), 4.24 (d, 2H, J=7.3 Hz), 3.89 (m, 2H), 2.25 (t, 2H, J=7.2 Hz), 1.80~1.25 (m, 16H), 0.89 (m, 6H); IR (KBr, cm⁻¹): 3550, 2940, 1610, 1105; Elemental analysis for: $C_{24}H_{35}N_1O_3$; Calculated (%): C 74.76; H 9.15; N 3.63; O 12.45; Found (%): C 74.75; H 9.09; N 3.52; O 12.64.

EXAMPLE 71

7-nitro-3-(2-pyridyloxy)-4-hydroxy-1-methyl-2(1H)-quinolinone (compound 65)

In accordance with EXAMPLE 21, ethyl 2-[N-methyl-N-(2-pyridyloxyacetyl)amino]-4-nitrobenzoate was used instead of ethyl 2-[N-methyl-N-(octyloxyacetyl)amino]-4-[(3,5-dimethoxy-4-hydroxycinnamoyl)amino]-benzoate, the title compound (65) was obtained.

¹H-NMR (d₆-DMSO, δ-TMS); 10.78 (s, 1H), 8.56 (m, 1H), 8.15~7.23 (m, 6H), 3.58 (s, 3H); IR (KBr, cm⁻¹): 3550, 2940, 1550, 1255; Elemental analysis for: $C_{15}H_{11}N_3O_5$; Calculated (%): C 57.51; H 3.54; N 13.42; O 25.54; Found (%): C 57.65; H 3.49; N 13.35; O 25.51.

EXAMPLE 72

7-nitro-3-methoxy-4-hydroxy-1-(2-franyl)-2(1H)-quinolinone (compound 66)

In accordance with EXAMPLE 21, ethyl 2-[N-(2-franyl)-N-(methoxyacetyl)amino]-4-nitrobenzoate was used instead of ethyl 2-[N-methyl-N-(octyloxyacetyl)amino]-4-[(3,5-dimethoxy-4-hydroxycinnamoyl)amino]-benzoate, the title compound (66) was obtained.

¹H-NMR (d₆-DMSO, δ-TMS); 10.78 (s, 1H), 8.15~7.69 (m,3H), 7.28 (m, 1H), 6.25 (m, 1H), 5.85 (m, 1H), 3.78 (s, 3H), 2.56 (s, 2H); IR (KBr, cm⁻¹): 3550, 2920, 1550, 1255; Elemental analysis for: $C_{15}H_{12}N_2O_6$; Calculated (%): C 56.96; H 3.82; N 8.86; O 30.35; Found (%): C 56.85; H 3.89; N 8.89; O 30.37.

EXAMPLE 73

5-phenoxycarbonyl-3-butoxy-4-hydroxy-1-methyl-2(1H)-quinolinone (compound 67)

In accordance with EXAMPLE 20, ethyl 2-[N-methyl-N-(butoxyacetyl)amino]-6-phenoxycarbonylbenzoate was used instead of ethyl 2-[N-methyl-N-(octyloxyacetyl)amino]-4-[(3,5-dimethoxy-4-hydroxycinnamoyl)amino]-benzoate, the title compound (67) was obtained.

¹H-NMR (d₆-DMSO, δ-TMS); 10.68 (s, 1H), 7.88~7.35 (m, 8H), 3.84 (t, 2H1, J=6.8 Hz), 3.62 (s, 3H), 1.78~1.34 (m, 4H), 0.96 (t, 3H, J=6.8 Hz); IR (KBr, cm⁻¹): 3550, 2920, 1715, 1610, 1250, 1100; Elemental analysis for: $C_{20}H_{21}N_1O_5$; Calculated (%): C 67.59; H 5.69; N 3.94; O 22.51; Found (%): C 67.45; H 5.99; N 3.97; O 22.59.

EXAMPLE 74

5-decyloxycarbonyl-3-butoxy-4-hydroxy-1-methyl-2(1H)-quinolinone (compound 68)

In accordance with EXAMPLE 20, ethyl 2-[N-methyl-N-(butoxyacetyl)amino]-6-decyloxycarbonyl-benzoate was used instead of ethyl 2-[N-methyl-N-octyloxyacetyl)amino]-4-[(3,5-dimethoxy-4-hydroxycinnamoyl)amino]-benzoate, the title compound (68) was obtained.

¹H-NMR (d₆-DMSO, δ-TMS); 10.68 (s, 1H), 7.88~7.45 (m, 3H), 4.23 (t, 2H, J=6.8 Hz), 3.84 (t, 2H, J=6.8 Hz), 3.62 (s, 3H), 1.78~1.34 (m, 20H), 0.96 (m, 6H); IR (KBr, cm⁻¹): 3550, 2940, 1715, 1610, 1250, 1100; Elemental analysis for: $C_{24}H_{37}N_1O_5$; Calculated (%): C 68.70; H 8.89; N 3.34; O 19.07; Found (%): C 68.64; H 8.79; N 3.23; O 19.34.

EXAMPLE 75

5-hexylamino-3-ethoxy-4-hydroxy-1-(3,5-dimethylbenzyl)-2(1H)-quinolinone (compound 69)

In accordance with EXAMPLE 21, ethyl 2-[N-(3,5-dimethylbenzyl)-N-(ethoxyacetyl)amino]-6-hexylaminobenzoate was used instead of ethyl 2-[N-methyl-N-(octyloxyacetyl)amino]-4-[(3,5-dimethoxy-4-hydroxycinnamoyl)amino]-benzoate, the title compound (69) was obtained.

¹H-NMR (d₆-DMSO, δ-TMS); 10.78 (s, 1H), 7.79 ~7.20 (m, 6H), 5.65 (bs, 1H), 3.65 (d, 2H, J=7.2 Hz), 3.33 (s, 2H), 2.89 (t, 2H, J=6.9 Hz), 1.86~1.23 (m, 8H), 2.25 (s, 6H), 1.15 (t, 3H, J=7.2 Hz), 0.90 (t, 3H, J=6.9 Hz); IR (KBr, cm⁻¹): 3550, 2940, 1715, 1610, 1100; Elemental analysis for: $C_{26}H_{34}N_2O_3$; Calculated (%): C 73.90; H 8.11; N 6.63; O 11.36; Found (%): C 73.89; H 8.10; N 6.58; O 11.43.

EXAMPLE 76

Ethyl 2-[N-benzyl-N-(methoxyacetyl)amino]-4-nitrobenzoate (compound 70)

In accordance with EXAMPLE 1, ethyl 2-benzylamino-4-nitrobenzoate and methoxyacetic acid were used instead of ethyl 4-nitrobenzoate and octyloxyacetic acid, the title compound (70) was obtained.

¹H-NMR (CDCl₃, δ-TMS); 9.55 (s, 1H), 8.21 (d, 1H, J=8.8 Hz), 7.91 (d, 1H, J=8.8 Hz), 7.25 (m, 5H), 4.23 (t, 2H, J=7.2 Hz), 4.13 (s, 2H), 3.78 (s, 3H), 3.33 (s, 2H), 1.15 (t, 31~1, J=6.8 Hz); IR (KBr, cm⁻¹): 2850, 1740, 1550, 1345, 1225; Elemental analysis for: $C_{19}H_{20}N_2O_6$; Calculated (%): C 61.28; H 5.41; N 7.52; O 25.78; Found (%): C 61.24; H 5.35; N 7.45; O 25.96.

EXAMPLE 77

Ethyl 2-[N-methyl-N-(phenoxyacetyl)amino]-4-nitrobenzoate (compound 71)

In accordance with EXAMPLE 1, ethyl 2-methylamino-4-nitrobenzoate and phenoxyacetic acid were used instead of ethyl 4-nitrobenzoate and octyloxyacetic acid, the title compound (71) was obtained.

¹H-NMR (CDCl₃, δ-TMS); 9.55 (s,1H), 8.18 (d, 1H, J=8.8 Hz), 7.91 (d, 1H, J=8.8 Hz), 7.35 (m, 5H), 4.23 (t, 2H, J=7.2 Hz), 4.13 (s, 2H), 3.56 (s, 3H), 1.15 (t, 3H, J=6.8 Hz); IR (KBr, cm⁻¹): 2850, 1740, 1550, 1345, 1225; Elemental analysis for: $C_{18}H_{18}N_2O_6$; Calculated (%): C 60.33; H 5.06; N 7.82; O 26.79; Found (%): C 60.24; H 5.15; N 7.75; O 26.86.

EXAMPLE 78

Ethyl 2-[N-methyl-N-(benzyloxyacetyl)amino]-4-nitrobenzoate (compound 72)

In accordance with EXAMPLE 1, ethyl 2-methylamino-4-nitrobenzoate and benzyloxyacetic acid were used instead of ethyl 4-nitrobenzoate and octyloxyacetic acid, the title compound (72) was obtained.

¹H-NMR (CDCl₃, δ-TMS); 9.55 (s, 1H), 8.18 (d, 1H, J=8.8 Hz), 7.91 (d, 1H, J=8.8 Hz), 7.35 (m, 5H), 5.25 (s,

2H), 4.23 (t, 2H, J=7.2 Hz), 4.13 (s, 2H), 3.56 (s, 3H), 1.15 (t, 3H, J=6.8 Hz); IR (KBr, cm$^{-1}$): 2850, 1740, 1550, 1345, 1225; Elemental analysis for: $C_{19}H_{20}N_2O_6$; Calculated (%): C 61.28; H 5.41; N 7.52; O 25.78; Found (%): C 61.22; H 5.45; N 7.55; O 25.78.

EXAMPLE 79

Ethyl 2-[N-(6-hydroxyhexyl)-N-(butoxyacetyl) amino]-4-nitrobenzoate (compound 73)

In accordance with EXAMPLE 1, ethyl 2-(6-hydroxyhexyl)amino-4-nitrobenzoate and butoxyacetic acid were used instead of ethyl 4-nitrobenzoate and octyloxyacetic acid, the title compound (73) was obtained.

$^1$H-NMR (CDCl$_3$, δ-TMS); 9.55 (s, 1H), 8.18 (d, 1H, J=8.8 Hz), 7.91 (d, 1H, J=8.8 Hz), 5.25 (s, 2H), 4.23 (t, 2H, J=7.2 Hz), 4.13 (s, 2H), 3.45 (m, 2H), 2.87 (m, 2H), 1.78~1.25 (m, 12H), 1.15 (t, 3H, J=6.8 Hz), 0.88 (t, 3H, J=6.8 Hz); IR (KBr, cm$^{-1}$): 2850, 1740, 1550, 1345, 1225; Elemental analysis for: $C_{21}H_{32}N_2O_7$; Calculated (%): C 59.42; H 7.60; N 6.60; O 26.39; Found (%): C 59.28; H 7.45; N 6.65; O 26.62.

EXAMPLE 80

6-nitro-3-octyloxy-4-hydroxy-1-methyl-2(1H)-quinolinone (compound 74)

In accordance with EXAMPLE 21, ethyl 2-[N-methyl-N-(octyloxyacetyl)amino]-6-nitrobenzoate was used instead of ethyl 2-[N-methyl-N-(octyloxyacetyl)amino]-4-[(3,5-dimethoxy-4-hydroxycinnamoyl)amino]-benzoate, the title compound (74) was obtained.

$^1$H-NMR (d$_6$-DMSO, δ-TMS); 11.05 (s, 1H), 8.09 (m, 3H), 3.64 (s, 3H), 3.68 (d, 2H, J=6.8 Hz), 1.87~1.23 (m, 12H), 0.90 (t, 3H, J=6.9 Hz); IR (KBr, cm$^{-1}$): 3500, 2940, 1610, 1515, 1250, 1100; Elemental analysis for: $C_{18}H_{24}N_2O_5$; Calculated (%): C 62.05; H 6.94; N 8.04; O 22.96; Found (%): C 62.02; H 7.04; N 8.00; O 22.64.

EXAMPILE 81

8-nitro-3-octyloxy-4-hydroxy-1-methyl-2(1H)-quinolinone (compound 75)

In accordance with EXAMPLE 21, ethyl 2-[N-methyl-N-(octyloxyacetyl)amino]-3-nitrobenzoate was used instead of ethyl 2-[N-methyl-N-(octyloxyacetyl)amino]-4-[(3,5-dimethoxy-4-hydroxycinnamoyl)amino]-benzoate, the title compound (75) was obtained.

$^1$H-NMR (d$_6$-DMSO, δ-TMS); 11.05 (s, 1H), 8.05 (m, 3H), 3.66 (s, 3H), 3.64 (d, 2H, J=6.8 Hz), 1.87~1.23 (m, 12H), 0.89 (t, 3H, J=6.9 Hz); IR (KBr, cm$^{-1}$): 3500, 2940, 1610, 1515, 1250, 1100; Elemental analysis for: $C_{18}H_{24}N_2O_5$; Calculated (%): C 62.05; H 6.94; N 8.04; O 22.96; Found (%): C 62.00; H 7.03; N 8.05; O 22.98.

EXAMPLE 82

7-acetylamino-3-octyloxy-4-hydroxy-1-methyl-2(1H)-quinolinone (compound 76)

In accordance with EXAMPLE 19, ethyl 2-[N-methyl-N-(octyloxyacetyl)amino]-4-acetylaminobenzoate was used instead of ethyl 2-[N-methyl-N-(octyloxyacetyl)amino]-4-[(3,5-dimethoxy-4-hydroxycinnamoyl)amino]-benzoate, the title compound (76) was obtained.

$^1$H-NMR (d$_6$-DMSO, δ-TMS); 10.28 (s, 1H), 10.23 (s, 1H), 7.85 (s, 1H), 7.80 (d, 1H, J=8.8 Hz), 7.42 (d, 1H, j=8.8 Hz), 3.94 (t, 1H, J=6.8 Hz), 3.52 (s, 3H), 2.10 (s, 3H), 1.69 (m, 2H), 1.25(m, 10H), 0.86 (t, 3H, J=6.8 Hz); IR (KBr, cm$^{-1}$): 3550,2940, 1610, 1515, 1250, 1100; Elemental analysis for: $C_{18}H_{26}N_2O_3$; Calculated (%): C 67.90; H 8.23; N 8.80; O 15.07; Found (%): C 67.95; H 8.21; N 8.81; O 15.03.

EXAMPLE 83

5-[(3,5-dimethoxy-4-hydroxycinnamoyl)amino]-3-octyloxy-4-hydroxy-1-methyl-2(1H)-quinolinone (compound 77)

In accordance with EXAMPLE 19, ethyl 2-[N-methyl-N-(octyloxyacetyl)amino]-6-[(3,5-dimethoxy-4-hydroxycinnamoyl)amino]-benzoate was used instead of ethyl 2-[N-methyl-N-(octyloxyacetyl)amino]-4-[(3,5-dimethoxy-4-hydroxycinnamoyl)amino]-benzoate, the title compound (77) was obtained.

$^1$H-NMR (d$_6$-DMSO, δ-TMS); 10.39 (s, 1H), 10.29 (s, 1H), 8.90 (s, 1H), 7.96 (s, 1H), 7.85 (d, 1H, J=8.8 Hz), 7.52 (d, 1H, J=15.6 Hz), 7.49 (s, 1H), 6.93 (s, 2H), 6.75 (d, 1H, J=15.6 Hz), 3.92 (t, 2H, J=6.8 Hz), 3.82 (s, 6H), 3.54 (s, 3H), 1.68 (m, 2H), 1.25 (m, 10H), 0.87 (t, 3H, J=6.8 Hz); IR (KBr, cm$^{-1}$): 3550,2940, 1600, 1515, 1250, 1100; Elemental analysis for: $C_{29}H_{36}N_2O_7$; Calculated (%): C 66.39; H 6.92; N 5.34; O 21.35; Found (%): C 66.44; H 7.00; N 5.30; O 21.26.

EXAMPLE 84

6-[(3,5-dimethoxy-4-hydroxycinnamoyl)amino]-3-octyloxy-4-hydroxy-1-methyl-2(1H)-quinolinone (compound 78)

In accordance with EXAMPLE 19, ethyl 2-[N-methyl-N-(octyloxyacetyl)amino]-5-[(3,5-dimethoxy-4-hydroxycinnamoyl)amino]-benzoate was used instead of ethyl 2-[N-methyl-N-(octyloxyacetyl)amino]-4-[(3,5-dimethoxy-4-hydroxycinnamoyl)amino]-benzoate, the title compound (78) was obtained.

$^1$H-NMR (d$_6$-DMSO, δ-TMS); 10.31 (s, 1H), 10.23 (s, 1H), 8.90 (s, 1H), 7.96 (s, 1H), 7.85 (d, 1H, J=8.8 Hz), 7.54 (d, 1H, J=15.6 Hz), 7.49 (s, 1H), 6.93 (s, 2H), 6.75 (d, 1H, J=15.6 Hz), 3.92 (t, 2H, J=6.8 Hz), 3.81 (s, 6H), 3.54 (s, 3H), 1.68 (m, 2H), 1.25 (m, 10H), 0.85 (t, 3H, J=6.8 Hz); IR (KBr, cm$^{-1}$): 3550, 2950, 1600, 1515, 1240, 1100; Elemental analysis for: $C_{29}H_{36}N_2O_7$; Calculated (%): C 66.39; H 6.92; N 5.34; O 21.35; Found (%) C 66.32; H 6.98; N 5.41; O 21.29.

EXAMPLE 85

8-[(3,5-dimethoxy-4-hydroxycinnamoyl)amino]-3-octyloxy-4-hydroxy-1-methyl-2(1H)-quinolinone (compound 79)

In accordance with EXAMPLE 19, ethyl 2-[N-methyl-N-(octyloxyacetyl)amino]-3-[(3, 5 -dimethoxy-4-hydroxycinnamoyl)amino]-benzoate was used instead of ethyl 2-[N-methyl-N-(octyloxyacetyl)amino]-4-[(3,5-dimethoxy-4-hydroxycinnamoyl)amino]-benzoate, the title compound (79) was obtained.

$^1$H-NMR (d$_6$-DMSO, δ-TMS); 10.35 (s, 1H), 10.23 (s, 1H), 8.90 (s, 1H), 7.94 (s, 1H), 7.85 (d, 1H, J=8.8 Hz), 7.54 (d, 1H, J=15.6 Hz), 7.50 (s, 1H), 6.93 (s, 2H), 6.74 (d, 1H, J=15.6 Hz), 3.92 (t, 2H, J=6.8 Hz), 3.81 (s, 6H), 3.54 (t, 2H, J=6.8 Hz), 1.68 (m, 2H), 1.25 (m, 10H), 0.87 (t, 3H, J=6.8 Hz); IR (KBr, cm$^{-1}$): 3550, 2940, 1550, 1515, 1240, 1100;

Elemental analysis for: $C_{29}H_{36}N_2O_7$; Calculated (%): C 66.39; H 6.92; N 5.34; O 21.35; Found (%): C 66.33; H 6.90; N 5.36; O 21.41.

EXAMPLE 86

6-ethoxycarbonyl-3-butoxy-4-hydroxy-1-methyl-2 (1H)-quinolinone (compound 80)

In accordance with EXAMPLE 20, ethyl 2-[N-methyl-N-(butoxyacetyl)amino]-5-thoxycarbonyl-benzoate was used instead of ethyl 2-[N-methyl-N-(octyloxyacetyl)amino]-4-[(3,5-dimethoxy-4-hydroxycinnamoyl)amino]-benzoate, the title compound (80) was obtained.

$^1$H-NMR ($d_6$-DMSO, δ-TMS); 10.68 (s, 1H), 7.88~7.55 (m, 3H), 4.22 (t, 2H, J=6.9 Hz), 3.84 (t, 2H, J=6.8 Hz), 3.62 (s, 3H), 1.78~1.34 (m, 4H), 1.22 (t, 3H, J=6.8 Hz), 0.96 (t, 3H, J=6.8 Hz); IR (KBr, cm$^{-1}$): 3550, 2940, 1715, 1610, 1250, 1100; Elemental analysis for: $C_{17}H_{21}N_1O_5$; Calculated (%): C 63.93; H 6.63; N 4.39; O 25.05; Found (%): C 63.70; H 6.58; N 4.45; O 25.27.

EXAMPLE 87

6-phenoxycarbonyl-3-butoxy-4-hydroxy-1-methyl-2 (1H)-quinolinone (compound 81)

In accordance with EXAMPLE 20, ethyl 2-[N-methyl-N-(butoxyacetyl)amino]5-phenoxycarbonyl-benzoate was used instead of ethyl 2-[N-methyl-N-(octyloxyacetyl) amino]-4-[(3,5-dimethoxy-4-hydroxycinnamoyl)amino]-benzoate, the title compound (81) was obtained.

$^1$H-NMR ($d_6$-DMSO, δ-TMS); 10.68 (s, 1H), 7.88~7.35 (m, 8H), 3.84 (t, 2H, J=6.8 Hz), 3.62 (s, 3H), 1.78~1.34 (m, 4H), 0.96 (t, 3H, J=6.8 Hz); IR (KBr, cm$^{-1}$): 3550, 2940, 1715, 1610, 1250, 1100; Elemental analysis for: $C_{20}H_{21}N_1O_5$; Calculated (%): C 67.59; H 5.96; N 3.94; O 22.51; Found (%): C 67.57; H 6.04; N 3.90; O 22.49.

EXAMPLE 88

8-ethoxycarbonyl-3-butoxy-4-hydroxy-1-methyl-2 (1H)-quinolinone (compound 82)

In accordance with EXAMPLE 20, ethyl 2-[N-methyl-N-(butoxyacetyl)amino]-3-ethoxycarbonyl-benzoate was used instead of ethyl 2-[N-methyl-N-(octyloxyacetyl)amino]-4-[(3,5-dimethoxy-4-hydroxycinnamoyl)amino]-benzoate, the title compound (82) was obtained.

$^1$H-NMR ($d_6$-DMSO, δ-TMS); 10.62 (s, 1H), 7.88~7.55 (m, 3H), 4.20 (t, 2H, J=6.9 Hz), 3.85 (t, 2H, J=6.8 Hz), 3.62 (s, 3H), 1.78~1.34 (m, 4H), 1.22 (t, 3H, J=6.8 Hz), 0.95 (t, 3H, J=6.8 Hz); IR (KBr, cm$^{-1}$): 3550, 2940, 1715, 1610, 1250, 1100; Elemental analysis for: $C_{17}H_{21}N_1O_5$; Calculated (%): C 63.93; H 6.63; N 4.39; O 25.05; Found (%): C 63.88; H 6.59; N 4.35; O 25.18.

EXAMPLE 89

8-phenoxycarbonyl-3-butoxy-4-hydroxy-1-methyl-2 (1H)-quinolinone (compound 83)

In accordance with EXAMPLE 20, ethyl 2-[N-methyl-N-(butoxyacetyl)amino]-3-phenoxycarbonyl-benzoate was used instead of ethyl 2-[N-methyl-N-(octyloxyacetyl) amino]-4-[(3,5-dimethoxy-4-hydroxycinnamoyl)amino]-benzoate, the title compound (83) was obtained.

$^1$H-NMR ($d_6$-DMSO, δ-TMS); 10.58 (s, 1H), 7.88~7.35 (m, 8H), 3.82 (t, 2H, J=6.8 Hz), 3.64 (s, 3H), 1.78~1.34 (m, 4H), 0.99 (t, 3H, J=6.8 Hz); IR (KBr, cm$^{-1}$): 3550, 2940, 1715, 1610, 1250, 1100; Elemental analysis for: $C_{20}H_{21}N_1O_5$; Calculated (%): C 67.59; H 5.96; N 3.94; O 22.51; Found (%): C 67.48; H 5.95; N 3.99; O 22.58.

EXAMPLE 90

5-octyloxy-3-methoxy-4-hydroxy-1-methyl-2(1H)-quinolinone (compound 84)

In accordance with EXAMPLE 21, ethyl 2-[N-methyl-N-(methoxyacetyl)amino]-6-octyloxybenzoate was used instead of ethyl 2-[N-methyl-N-(octyloxyacetyl)amino]-4-[(3,5-dimethoxy-4-hydroxycinnamoyl)amino]-benzoate, the title compound (84) was obtained.

H-NMR ($d_6$-DMSO, δ-TMS); 10.85 (s, 1H), 7.75~7.20 (m, 3H), 3.74 (s, 3H), 3.65 (s, 3H), 2.22 (d, 2H, J=7.0 Hz), 1.78~1.23 (m, 12H), 0.89 (t, 3H, J=7.0 Hz); IR (KBr, cm$^{-1}$): 3550, 2940, 1610, 1100; Elemental analysis for: $C_{19}H_{27}N_1O_4$; Calculated (%): C 68.44; H 8.16; N 4.20; O 19.20; Found (%): C 68.46; H 8.19; N 4.27; O 19.08.

EXAMPLE 91

3,8-dihexyloxy-4-hydroxy-1-methyl-2(1H)-quinolinone (compound 85)

In accordance with EXAMPLE 21, ethyl 2-[N-methyl-N-(hexyloxyacetyl)amino]-3-hexyloxybenzoate was used instead of ethyl 2-[N-methyl-N-(octyloxyacetyl)amino]-4-[(3,5-dimethoxy-4-hydroxycinnamoyl)amino]-benzoate, the title compound (85) was obtained.

$^1$H-NMR ($d_6$-DMSO, δ-TMS); 10.85 (s, 1H), 7.75~7.20) m, 3H), 3.65 (s, 3H), 2.22 (d, 2H, J=7.0 Hz), 2.00 (d, 2H, J=7.0 Hz), 1.78~1.23 (m, 16H), 0.89 (t, 3H, J=7.0 Hz), 0.83 (t, 3H, J=7.0 Hz); IR (KBr, cm$^{-1}$):3550,2940, 1610, 1100; Elemental analysis for: $C_{22}H_{33}N_1O_4$; Calculated (%): C 70.37; H 8.86; N 3.73; O 17.04; Found (%): C 70.39; H 8.92; N 3.71; O 16.98.

EXAMPLE 92

8-methylamino-3-octyloxy-4-hydroxy-1-methyl-2 (1H)-quinolinone (compound 86)

In accordance with EXAMPLE 19, ethyl 2-[N-methyl-N-(octyloxyacetyl)amino]-3-methylaminobenzoate was used instead of ethyl 2-[N-methyl-N-(octyloxyacetyl)amino]-4-[(3,5-dimethoxy-4-hydroxycinnamoyl)amino]-benzoate, the title compound (86) was obtained.

$^1$H-NMR ($d_6$-DMSO, δ-TMS); 11.23 (s, 1H), 7.85 (s, 1H), 7.76 (d, 1H, J=7.2 Hz), 7.50 (d, 1H, J=7.2 Hz), 4.23 (d, 2H, J=7.6 Hz), 3.54 (s, 3H), 3.34 (s, 3H), 1.86~1.45 (m, 12H), 0.97 (t, 3H, J=7.5 Hz); IR (KBr, cm$^{-1}$): 3550, 2940, 1550, 1515, 1240, 1100; Elemental analysis for: $C_{19}H_{28}N_2O_3$; Calculated (%): C 68.64; H 8.49; N 8.43; O 14.44; Found (%): C 68.61; H 8.50; N 8.49; O 14.40.

EXAMPLE 93

Methyl 2-[N-methyl-N-(octyloxyacetyl)amino]-4-aminobenzoate (compound 87)

In accordance with EXAMPLE 4, Methyl 2-[(octyloxyacetyl)amino]-4-aminobenzoate was used instead of ethyl 2-[(octyloxyacetyl)amino]-4-aminobenzoate, the title compound (87) was obtained.

$^1$H-NMR (CDCl$_3$, δ-TMS); 7.94 (d, 1H, J=8.0 Hz), 6.65 (d, 1H, J=8.0 Hz), 6.32 (d, 1H, J=1.6 Hz), 4.40 (s, 2H), 4.27

(m, 2H), 3.82 (s, 3H), 3.40 (m, 2H), 3.18 (s, 3H), 1.80~1.20 (m, 12H), 0.87 (t, 3H, J=6.8 Hz); IR (KBr, cm$^{-1}$): 3350, 2850, 1725; Elemental analysis for: $C_{19}H_{30}N_2O_4$; Calculated (%): C 65.11; H 8.63; N 7.99; O 18.26; Found (%): C 65.08; H 8.59; N 8.02; O 18.31.

EXAMPLE 94

Butyl 2-[N-methyl-N-(octyloxyacetyl)amino]-4-aminobenzoate (compound 88)

In accordance with EXAMPLE 4, butyl 2-[(octyloxyacetyl)amino]-4-aminobenzoate was used instead of ethyl 2-[(octyloxyacetyl)amino]-4-aminobenzoate, the title compound (88)was obtained.

$^1$H-NMR (CDCl$_3$, δ-TMS); 7.94 (d, 1H, J=8.0 Hz), 6.65 (d, 1H, J=8.0 Hz), 6.32 (d, 1H, J=1.6 Hz), 4.40 (s, 2H), 4.27 (m, 2H), 3.82 (s, 3H), 3.40 (m, 2H), 3.18 (s, 3H), 2.30~1.20 (m, 14H), 0.87 (m, 6H); IR (KBr, cm$^{-1}$): 3350, 2850, 1725; Elemental analysis for: $C_{22}H_{36}N_2O_4$; Calculated (%): C 67.31; H 9.24; N 7.14; O 16.30; Found (%): C 67.28; H 9.27; N 7.21; O 16.24.

EXAMPLE 95

Methyl 2-[N-methyl-N-(octyloxyacetyl)amino]-4-[(3,5-dimethoxy-4-hydroxycinnamoyl)amino]-benzoate (compound 89)

In accordance with EXAMPLE 5, Methyl 2-[N-methyl-N-(octyloxyacetyl)amino]-4-aminobenzoate was used instead of Ethyl 2-[N-methyl-N-(octyloxyacetyl)amino]-4-aminobenzoate, the title compound (89)was obtained.

$^1$H-NMR (d$_6$-DMSO, δ-TMS); 10.52 (s, 1H), 8.94 (s, 1H), 7.96 (d, 1H, J=8.8 Hz), 7.83 (d. 1H, J=2.0 Hz), 7.76 (d, 1H, J=8.8 Hz), 7.57 (d, 1H, J=15.6 Hz), 6.93 (s, 2H), 6.68 (d, 1H, J=15.6 Hz), 3.85 (s, 6H), 3.81 (s, 3H), 3.78 (s, 3H), 3.68 (m, 2H), 3.27 (m, 2H), 1.40~1.10 (m, 12H), 0.83 (m, 3H); IR (KBr, cm$^{-1}$): 3350, 1745, 1680, 1225; Elemental analysis for: $C_{30}H_{40}N_2O_8$; Calculated (%): C 64.73; H 7.24; N 5.03; O 23.00; Found (%): C 64.77; H 7.20; N 4.95; O 23.07.

EXAMPLE 96

7-[(3,5-dimethoxy-4-hydroxy-cinnamoyl)amino]-3-octyloxy-4-hydroxy-1-methyl-2(1H)-quinolinone (compound 18)

In accordance with EXAMPLE 19, methyl 2-[N-methyl-N-(octyloxyacetyl)amino]-4-[(3,5-dimethoxy-4-hydroxycinnamoyl)amino]-benzoate was used instead of ethyl 2-[N-methyl-N-(octyloxyacetyl)amino]-4-[(3,5-dimethoxy-4-hydroxycinnamoyl)amino]-benzoate, the title compound (18)was obtained.

EXAMPLE 97

7-[(3,5-dimethoxy-4-hydroxy-cinnamoyl)amino]-3-octyloxy-4-hydroxy-1-methyl-2(1H)-quinolinone (compound 18)

In accordance with EXAMPLE 19, butyl 2-[N-methyl-N-(octyloxyacetyl)amino]-4-[(3,5-dimethoxy-4-hydroxycinnamoyl)amino]-benzoate was used instead of ethyl 2-[N-methyl-N-(octyloxyacetyl)amino]-4-[(3,5-dimethoxy-4-hydroxycinnamoyl)amino]-benzoate, the title compound (18)was obtained.

Reference Example 1

Cyclization of ethyl 2-[(methoxyacetyl)amino]-7-nitro-benzoate

To a mixture of 0.58 g of sodium hydride (purity 60%, 14.49 mmol) in 9 ml of tetrahydrofuran was added a solution of 1.02 g of ethyl 2-[(methoxyacetyl)amino]-7-nitro-benzoate (3.62 mmol) in 6 ml of tetrahydrofuran at 0 to 10° C. After the mixture was stirred at 0 to 10° C. for 5 hours. No proceeding of cyclization was observed.

Test Example 1

Acute toxicity test in mice

We performed this test in order to confirm the low toxicity of the compounds of the present invention, quinolinone derivatives. In the following, the method of the acute toxicity test will be explained.

Method:Each of quinolinone derivatives (compound No. 18 to 69, 74 to 86) were orcibly administered orally at the doses of 1000 and 2000 mg/kg to male ICR mice (body weight is 20 to 25 g, 5 mice per one (1) group), using an esophageal sound. After the administration, the animals were kept in cages for 7 days, to observed general symptoms and to count dead animals. Lethal dose (LD$_{50}$:mg/kg) was extrapolated from the mortality at 7th day after administration.

In result, the LD$_{50}$ of all compounds were over 1000 mg/kg, and therefore it was clearly shown that the compounds of the present invention, quinolinone derivatives, have extremely low toxicity.

Test Example 2

Effect on homologous passive cutaneous anaphylaxis (PCA) reaction in rats

We performed this pharmacological test by PCA reaction, which was well known screening test for anti-allergic agents in order to demonstrate that the compounds of the present invention, quinolinone derivatives, possess anti-allergic activity. This experimental animal model is caused by immediate type allergic reaction, namely, antigen-antibody reaction. In the following, the method of this pharmacological test will be explained.

Method:Male wistar rats (9 weeks old) were intradermally administered 0.05 ml of anti-serum against dinitrophenylated ascaris (DNP-As) into two sites on the shaved dorsal skin. 48 hours later, quinolinone derivatives (test compounds) suspended in 0.5% methylcellulose (MC) were given orally at a dose of 100 mg/kg to the animals. 1 hour after administration of Test compounds, the animals were induced anaphylaxis by injection of saline (1 ml) dissolving 1 mg of trinitrophenylated ascaris (TNP-As) and 5 mg of Evans Blue into the tail vein of the animals. 30 minutes after induction of anaphylaxis, animals were anesthetized by ether and killed by bleeding, and were flayed dorsal skin. The leakage of dye was assessed by measuring the diameter (mean of shortest and longest diameter) of the blue spot on the inside surface of dorsal skin. As vehicle control group, only 0.5% MC solution was administered orally, and as positive control group, Tranilast suspended in 0.5% MC were administered orally at a dose of 200 mg/kg to the animals with the same method as the test compounds groups. The inhibition (%) of PCA reaction was calculated according to equation 1 and the result was shown in table 1. Each experimental group consisted of 5 rats. In the conditions of this experiment, it was considered that the compound, which inhibited PCA reaction by over forty (40) percent against that in vehicle control group, was evidently effective for immediate type allergy.

Inhibition (%)=(A—B)/A×100    Equation 1

In equation 1:

A: leakage of dye in vehicle control group
B leakage of dye in test compound group or positive control group

TABLE 1

| Compound No. | Inhibition (%) | Compound No. | Inhibition (%) |
|---|---|---|---|
| 23 | 40 | 61 | 42 |
| 24 | 42 | 68 | 49 |
| 26 | 39 | 76 | 51 |
| 34 | 37 | 77 | 55 |
| 36 | 45 | 78 | 50 |
| 38 | 45 | 79 | 49 |
| 44 | 42 | 80 | 41 |
| 45 | 46 | 83 | 42 |
| 49 | 50 | 84 | 49 |
| 52 | 49 | 85 | 50 |
| 53 | 45 | 86 | 53 |
| 54 | 50 | Tranilast | 52 |

Formulation Example 1

| (5% powders) | |
|---|---|
| the compound of the present invention | 50 mg |
| lactos | 950 mg |
| | 1000 mg |

In the following, the procedure for powders of compound 22, 24 and 45 will be shown. Crystals of the compound of the present invention were pulverized in amortar and thoroughly mixed with lactose. Secondly the mixture was pulverized with a pestle and 5% powders of compound 22, 24 and 45 were obtained.

Formulation Example 2

| (10% powders) | |
|---|---|
| the compound of the present invention | 100 mg |
| lactos | 900 mg |
| | 1000 mg |

In the following, the procedure for powders of compound 34, 52, 53 and 61 will be shown. The procedure of FORMULATION EXAMPLE 1 was repeated to obtain 10% powders of compound 34, 52, 53 and 61.

Formulation Example 3

| (10% granules) | |
|---|---|
| the compound of the present invention | 300 mg |
| lactose | 2000 mg |

| (10% granules) | |
|---|---|
| starch | 670 mg |
| gelatin | 30 mg |
| | 3000 mg |

In the following, the procedure for granules of compound 38, 44, 49 and 68 will be shown. The compound of the present invention was mixed with the equivalent amount of starch and pulverized in a mortar. This was further mixed with lactose and the remaining portion of starch. Separately from this, 30 mg of gelatin was mixed with 1 ml of purified water, solubilized by heating, cooled and then, with stirring, mixed with 1 ml of ethanol to prepare a gelatin solution. Thereafter, the mixture prepared above was mixed with the gelatin solution, and the resulting mixture was kneaded, granulated and then dried to obtain granules of compound 38, 44, 49 and 68.

Formulation Example 4

| (5 mg tablets) | |
|---|---|
| the compound of the present invention | 5 mg |
| lactose | 62 mg |
| starch | 30 mg |
| talc | 2 mg |
| magnesium stearate | 1 mg |
| | 100 mg/tablet |

In the following, the procedure for tablets of compound 76 to 80 will be shown. A 20 times larger portion of the above composition was used to prepare tablets each of which containing 5 mg of the active ingredient. That is, 100 mg of the compound of the present invention in a crystal form was pulverized in a mortar and mixed with lactose and starch. The thus prepared formulation was mixed with 10% starch paste, and the mixture was kneaded and then subjected to granulation. After drying, the resulting granules were mixed with talc and magnesium stearate and subjected to tablet making in usual way. With the above procedure, tablets of compound 76 to 80 were prepared.

Formulation Example 5

| (20 mg tablets) | |
|---|---|
| the compound of the present invention | 20 mg |
| 6% hydroxypropylcellulose/lactose | 75 mg |
| stearate/talc | 2 mg |
| potato starch | 3 mg |
| | 100 mg/tablet |

In the following, the procedure for tablets of compound 76 to 80 will be shown. A 10 times larger portion of the above composition was used to prepare tablets each of which containing 20 mg of the active ingredient. That is, 6 g of hydroxypropylcellulose was dissolved in an appropriate volume of ethanol and mixed with 94 g of lactose, followed by kneading. After drying to a degree, the mixture was passed through a No. 60 mesh, and the thus graded granules were used as 6% hydroxypropylcellulose/lactose. Separately from this, magnesium stearate and talc were mixed at a ratio of 1:4 and used as stearate/talc. Thereafter, the compound of the present invention, 6% hydroxypropylcellulose/lactose, stearate/talc and potato starch were thoroughly mixed and subjected to tablet making in usual way. With the above procedure, tablets of compound 76 to 80 were prepared.

Formulation Example 6

| (25 mg tablets) | |
| --- | --- |
| the compound of the present invention | 25 mg |
| lactose | 122 mg |
| carboxymethylstarch | 50 mg |
| talc | 2 mg |
| magnesium stearate | 1 mg |
| | 200 mg/tablet |

In the following, the procedures for tablets of compound 44, 54, 76 to 80, 85 and 86 will be shown. A 10 times larger portion of the above composition was used to prepare tablets each of which containing 25 mg of the active ingredient. That is, 250 mg of the compound of the present invention in a crystal form was pulverized in a mortar and thoroughly mixed with lactose. An appropriate volume of purified water was added to carboxymethylstarch, which was subsequently added to the above mixture, and the resulting mixture was kneaded and then subjected to granulation. After drying, the thus prepared granules were mixed with talc and magnesium stearate and subjected to tablet making in usual way. With the above procedure, tablets of compound 44, 54, 76 to 80, 85 and 86 were prepared.

Formulation Example 7

| (10 mg capsules) | |
| --- | --- |
| the compound of the present invention | 300 mg |
| lactose | 2000 mg |
| starch | 670 mg |
| gelatin | 30 mg |
| | 3000 mg/tablet |

In the following, the procedures for tablets of compound 44, 54, 76 to 80, 85 and 86 will be shown. Granules were prepared in accordance with the procedure described in Formulation EXAMPLE 3 and packed in capsules in 100 mg portions. With the above procedure, capsules of compound 44, 54, 76 to 80, 85 and 86 were prepared.

Formulation Example 8

| (0.5% ointment) | |
| --- | --- |
| the compound of the present invention | 5 mg |
| liquid paraffin | 80 mg |
| petrolatum album | 915 mg |
| | 1000 mg |

In the following, the procedures for tablets of compound 44, 54, 76 to 80, 85 and 86 will be shown. A 10 times larger portion of the above composition was used to prepare ointment each of which containing 5% of the active ingredient. This is, the compound of the present invention and a little liquid paraffin were sufficiently mixed and pulverized in a mortar, and used as dispersive solution. Separately from this, petrolatum album was mixed with liquid paraffin by heating to prepare bases. The above dispersive solution was by degrees added to the bases, and thoroughly kneaded to homogenize. With the above procedure, ointment of 44, 54, 76 to 80, 85 and 86 were prepared.

Industrial manufacturing method of quinolinone derivative and a novel amide derivatives as a intermediate to use this method Thus, it is apparent that there has been provided, in accordance with the present invention, a industrial manufacturing method of quinolinone derivative and a novel amide derivatives as a intermediate to use this method. Also provided quinolinone derivative and its physiologically acceptable salt are excellent antiallergic agents which have low toxicity and are useful for the treatment or prevention of immediate type and delayed type allergic diseases, particularly an excellent antiallergic agent which is highly effective on delayed type allergy that cannot be treated effectively with the prior art antiallergic agents.

While the invention has been described in detail and with reference to specific embodiments thereof, it will be apparent to one skilled in the art that various changes and modifications can be made therein without departing from the spirit and scope thereof.

What is claimed is:

1. A method for preparing a quinolinone compound represented by formula (II), wherein an amide compound represented by formula (I) is reacted with a basic agent, followed by intramolecular ring formation:

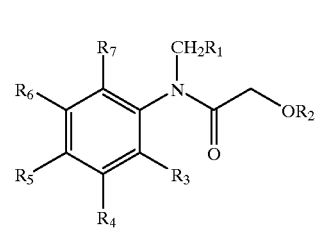

(I)

wherein $R_1$ represents a hydrogen atom, an alkyl group, an alkyl group containing a hydroxyl group, an alkenyl group, or an aryl group;

$R_2$ represents an alkyl group, an alkenyl group, an aryl group, or an aralkyl group;

$R_3$ represents a reactive carboxyl group; and $R_4$ to $R_7$ represent, respectively and independently, a hydrogen atom; a hydroxyl group; an alkyl group; an alkoxy group; an alkenyl group; an alkenyloxy group; an aryl group; an aryloxy group; an aralkyloxy group; a $R_8R_9N$ group wherein $R_8$ and $R_9$ represent, respectively and independently, a hydrogen atom, an alkyl group, an alkenyl group, an aralkyl group, or an acyl group; a nitro group; or a $R_{10}OOC$ group wherein $R_{10}$ represents a hydrogen atom, an alkyl group, an alkenyl group, an aryl group, or an aralkyl group;

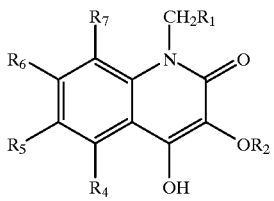

wherein $R_1$, $R_2$ and $R_4$ to $R_7$ represent, respectively, the same groups as described in formula (I).

2. A method for preparing a quinolinone compound according to claim 1, wherein $R_1$ is selected from the group consisting of a hydrogen atom, a straight-chain or branched-chain alkyl group having 1 to 9 carbon atoms, a straight-chain or branched-chain alkyl group containing a hydroxyl group and having 1 to 5 carbon atoms, a straight-chain or branched-chain alkenyl group having 2 to 9 carbon atoms, and an aryl group having 5 to 8 carbon atoms; $R_2$ is selected from the group consisting of a straight-chain or branched-chain alkyl group having 1 to 10 carbon atoms, a straight-chain or branched-chain alkenyl group having 2 to 10 carbon atoms, an aryl group having 5 to 8 carbon atoms, and an aralkyl group having 7 to 9 carbon atoms; $R_4$, $R_5$ and $R_7$ each represents a hydrogen atom; and $R_6$ represents a $R_8R_9N$ group wherein $R_8$ and $R_9$ represent, respectively and independently, a hydrogen atom, an alkyl group having 1 to 10 carbon atoms, an alkenyl group having 2 to 10 carbon atoms, an aralkyl group having 7 to 9 carbon atoms, or an acyl group having 2 to 12 carbon atoms.

3. A method for preparing a quinolinone compound according to claim 1, wherein $R_1$ represents a hydrogen atom; $R_2$ is selected from the group consisting of a straight-chain or branched-chain alkyl group having 1 to 10 carbon atoms, a straight-chain or branched-chain alkenyl group having 2 to 10 carbon atoms, an aryl group having 5 to 8 carbon atoms, and an aralkyl group having 7 to 9 carbon atoms; $R_4$, $R_5$ and $R_7$ each represents a hydrogen atom; and $R_6$ represents a $R_8R_9N$ group wherein $R_8$ and $R_9$ represent, respectively and independently, a hydrogen atom, an alkyl group having 1 to 10 carbon atoms, an alkenyl group having 2 to 10 carbon atoms, an aralkyl group having 7 to 9 carbon atoms, or an acyl group having 2 to 12 carbon atoms.

4. A method for preparing a quinolinone compound according to claim 1, wherein $R_1$ is selected from the group consisting of a hydrogen atom, a straight-chain or branched-chain alkyl group having 1 to 9 carbon atoms, a straight-chain or branched-chain alkyl group containing a hydroxyl group and having 1 to 5 carbon atoms, a straight-chain or branched-chain alkenyl group having 2 to 9 carbon atoms, and an aryl group having 5 to 8 carbon atoms; $R_2$ is selected from the group consisting of a straight-chain or branched-chain alkyl group having 1 to 10 carbon atoms, a straight-chain or branched-chain alkenyl group having 2 to 10 carbon atoms, an aryl group having 5 to 8 carbon atoms, and an aralkyl group having 7 to 9 carbon atoms; $R_4$, $R_5$ and $R_7$ each represents a hydrogen atom; and $R_6$ represents a nitro group.

5. A method for preparing a quinolinone compound according to claim 1, wherein $R_1$ represents a hydrogen atom; $R_2$ is selected from the group consisting of a straight-chain or branched-chain alkyl group having 1 to 10 carbon atoms, a straight-chain or branched-chain alkenyl group having 2 to 10 carbon atoms, an aryl group having 5 to 8 carbon atoms, and an aralkyl group having 7 to 9 carbon atoms; $R_4$, $R_5$ and $R_7$ each represents a hydrogen atom; and $R_6$ represents a nitro group.

6. A method for preparing a quinolinone compound according to claim 1, wherein $R_1$ is selected from the group consisting of a hydrogen atom, a straight-chain or branched-chain alkyl group having 1 to 9 carbon atoms, a straight-chain or branched-chain alkyl group containing a hydroxyl group and having 1 to 5 carbon atoms, a straight-chain or branched-chain alkenyl group having 2 to 9 carbon atoms, and an aryl group having 5 to 8 carbon atoms; $R_2$ is selected from the group consisting of a straight-chain or branched-chain alkyl group having 1 to 10 carbon atoms, a straight-chain or branched-chain alkenyl group having 2 to 10 carbon atoms, an aryl group having 5 to 8 carbon atoms, and an aralkyl group having 7 to 9 carbon atoms; $R_4$, $R_5$ and $R_7$ each represents a hydrogen atom; and $R_6$ is selected from the group consisting of a hydroxyl group, a straight-chain or branched-chain alkyloxy group having 1 to 10 carbon atoms, a straight-chain or branched-chain alkenyloxy group having 2 to 10 carbon atoms, and an aralkyloxy group having 7 to 9 carbon atoms.

7. A method for preparing a quinolinone compound according to any one of claims 1 to 6, wherein said basic agent is an alkali metal alkoxide.

8. A method for preparing a quinolinone compound according to any one of claims 1 to 6, wherein said basic agent is an alkali metal amide.

9. A quinolinone compound represented by formula (II) or its salt

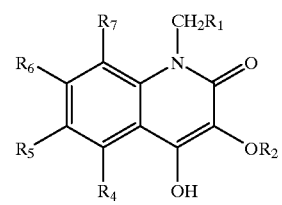

wherein
$R_1$ represents a hydrogen atom, an alkyl group, an alkyl group containing a hydroxyl group, an alkenyl group, or an aryl group;
$R_2$ represents an alkyl group, an alkenyl group, an aryl group, or an aralkyl group; and
$R_4$ to $R_7$ represent, respectively and independently, a hydrogen atom; a hydroxyl group; an alkyl group; an alkoxy group; an alkenyl group; an alkenyloxy group; an aryl group; an aryloxy group; an aralkyloxy group; a $R_8R_9N$ group wherein $R_8$ and $R_9$ represent, respectively and independently, a hydrogen atom, an alkyl group, an alkenyl group, an aralkyl group or an acyl group; a nitro group; or a $R_{10}OOC$ group wherein $R_{10}$ represents a hydrogen atom, an alkyl group, an alkenyl group, an aryl group, or an aralkyl group;
with the exception that the following two types of compounds are not included: (i) a compound in which $R_4$, $R_5$ and $R_7$ are respectively hydrogen atoms, and $R_6$ is selected from the group comprising a hydrogen atom; a hydroxyl group; an alkoxy group; an alkenyloxy group; an aralkyloxy group; a $R_8R_9N$ group wherein $R_8$ and $R_9$ represent, respectively and independently, a hydrogen atom, an alkyl group, an alkenyl group, an aralkyl group, or an acyl group; and a nitro group; and (ii) a compound in which $R_4$, $R_5$ and $R_6$ are respectively hydrogen atoms, and $R_7$ is a methoxy group.

10. A quinolinone compound or its salt according to claim 9, wherein $R_1$ is selected from the group consisting of a hydrogen atom, a straight-chain or branched-chain alkyl group having 1 to 9 carbon atoms, a straight-chain or branched-chain alkyl group containing a hydroxyl group and having 1 to 5 carbon atoms, a straight-chain or branched-chain alkenyl group having 2 to 9 carbon atoms, and an aryl group having 5 to 8 carbon atoms; $R_2$ is selected from the group consisting of a straight-chain or branched-chain alkyl group having 1 to 10 carbon atoms, a straight-chain or branched-chain alkenyl group having 2 to 10 carbon atoms, an aryl group having 5 to 8 carbon atoms, and an aralkyl group having 7 to 9 carbon atoms; $R_4$ to $R_7$ represent, respectively and independently, a hydrogen atom, a hydroxyl group, a straight-chain or branched-chain alkyl group having 1 to 10 carbon atoms, a straight-chain or branched-chain alkoxy group having 1 to 10 carbon atoms, a straight-chain or branched-chain alkenyl group having 2 to 10 carbon atoms, a straight-chain or branched-chain alkenyloxy group having 2 to 10 carbon atoms, an aryl group having 5 to 8 carbon atoms, an aryloxy group having 5 to 8 carbon atoms, and an aralkyloxy group having 7 to 9 carbon atoms; $R_8$ and $R_9$ represent, respectively and independently, a hydrogen atom, an alkyl group having 1 to 10 carbon atoms, an alkenyl group having 2 to 10 carbon atoms, an aralkyl group having 7 to 9 carbon atoms, or an acyl group having 2 to 12 carbon atoms; and $R_{10}$ is selected from the group consisting of a straight-chain or branched-chain alkyl group having 1 to 10 carbon atoms, a straight-chain or branched-chain alkenyl group having 2 to 10 carbon atoms, an aryl group having 5 to 8 carbon atoms, and an aralkyl group having 7 to 9 carbon atoms.

11. A quinolinone compound or its salt according to claim 9, wherein $R_1$ represents a hydrogen atom; $R_2$ represents a straight-chain or branched-chain alkyl group having 1 to 10 carbon atoms, a straight-chain or branched-chain alkenyl group having 2 to 10 carbon atoms, an aryl group having 5 to 8 carbon atoms, or an aralkyl group having 7 to 9 carbon atoms; $R_4$ to $R_7$ represent, respectively and independently, a hydrogen atom, a hydroxyl group, a straight-chain or branched-chain alkyl group having 1 to 10 carbon atoms, a straight-chain or branched-chain alkoxy group having 1 to 10 carbon atoms, a straight-chain or branched-chain alkenyl group having 2 to 10 carbon atoms, a straight-chain or branched-chain alkenyloxy group having 2 to 10 carbon atoms, an aryl group having 5 to 8 carbon atoms, an aryloxy group having 5 to 8 carbon atoms, or an aralkyloxy group having 7 to 9 carbon atoms; $R_8$ and $R_9$ represent, respectively and independently, a hydrogen atom, an alkyl group having 1 to 10 carbon atoms, an alkenyl group having 2 to 10 carbon atoms, an aralkyl group having 7 to 9 carbon atoms, or an acyl group having 2 to 12 carbon atoms; and $R_{10}$ is selected from the group consisting of a straight-chain or branched-chain alkyl group having 1 to 10 carbon atoms, a straight-chain or branched-chain alkenyl group having 2 to 10 carbon atoms, an aryl group having 5 to 8 carbon atoms, and an aralkyl group having 7 to 9 carbon atoms.

12. A quinolinone compound or its salt according to claim 9, wherein $R_1$ is selected from the group consisting of a hydrogen atom and a straight-chain or branched-chain alkyl group having 1 to 9 atoms; and $R_2$ is selected from the group consisting of a straight-chain or branched-chain alkyl group having 1 to 10 carbon atoms, a straight-chain or branched-chain alkenyl group having 2 to 10 carbon atoms, an aryl group having 5 to 8 carbon atoms, and an aralkyl group having 7 to 9 carbon atoms.

13. A pharmaceutical composition comprising as active ingredient a quinolinone compound or its salt according to any one of claims 9 to 12.

14. An anti-allergic pharmaceutical composition comprising as active ingredient a quinolinone compound or its salt according to any one of claims 9 to 12.

15. A method of treating allergic diseases of mammals, comprising administering a therapeutically effective amount of the quinolinone compound or salt thereof as claimed in any one of claims 9 to 12.

* * * * *